(12) United States Patent
Masci et al.

(10) Patent No.: US 7,745,192 B2
(45) Date of Patent: Jun. 29, 2010

(54) PROTHROMBIN ACTIVATING PROTEIN

(75) Inventors: Paul Pantaleone Masci, Brisbane (AU); John De Jersey, Brisbane (AU); Martin Lavin, Brisbane (AU)

(73) Assignee: Venomics PTY Limited (AU)

( * ) Notice: Subject to any disclaimer, the term of this patent is extended or adjusted under 35 U.S.C. 154(b) by 0 days.

(21) Appl. No.: 10/406,031

(22) Filed: Apr. 2, 2003

(65) Prior Publication Data

US 2004/0043017 A1 Mar. 4, 2004

(51) Int. Cl.
C12N 9/64 (2006.01)

(52) U.S. Cl. ...................................... 435/226

(58) Field of Classification Search .................. 435/212
See application file for complete search history.

(56) References Cited

U.S. PATENT DOCUMENTS 4,363,319 A * 12/1982 Altshuler ..................... 604/304
5,102,360 A * 4/1992 Eycleshimer ................ 441/80

FOREIGN PATENT DOCUMENTS

| WO | WO 99/58569 | 11/1999 |
|---|---|---|
| WO | WO 99/59647 | 11/1999 |

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
Masci et al Purification and characterization of a prothrombin activator from the venom of the Australian brown snake, *Pseudonaja textilis* textilis. Biochem Int. Nov. 1988;17(5):825-35.*
Masci et al Brown snakes (*Pseudonaja* genus): Venom yields, prothrombin activator neutralization and implications affecting antivenom usage. Anaesthesia and Intensive Care. Jun. 1998. vol. 26, Iss. 3; p. 276-281.*
Joseph et al Amino acid sequence of trocarin, a prothrombin activator from *Tropidechis carinatus* venom: its structural similarity to coagulation factor Xa. Blood. Jul. 15, 1999;94(2):621-631.*
DataBase UniProt_03 Accession No. FA10_TROCA/P81428 May 30, 2000 from Joseph et al Blood. Jul. 15, 1999;94(2):621-631. Alignment with SEQ ID No. 2.*
Shea et al, The distribution and identification of dangerously venomous Australian terrestrial snakes. Aust Vet J. Dec. 1999;77(12):791-8. Review.*
Carey, A systematic and general proteolytic method for defining structural and functional domains of proteins. Methods Enzymol. 2000;328:499-514.*
Guo et al, Protein tolerance to random amino acid change. Proc Natl Acad Sci U S A. Jun. 22, 2004;101(25):9205-9210. Epub Jun. 14, 2004.*

Guo et al, Protein tolerance to random amino acid change. Proc Natl Acad Sci U S A. Jun. 22, 2004;101(25):9205-9210. Epub Jun. 14, 2004.*
USPTO in house calculations for the genus of recited variants, Nov. 19, 2009. Based on Guo et al, 2004.*
UniProt database Accession No. P81428 May 30, 2000 from Joseph et al, Amino acid sequence of trocarin, a prothrombin activator from *Tropidechis carinatus* venom: its structural similarity to coagulation factor Xa. Blood. Jul. 15, 1999;94(2):621-31. Alignment with SEQ ID No. 2.*
Joseph et al, Amino acid sequence of trocarin, a prothrombin activator from *Tropidechis carinatus* venom: its structural similarity to coagulation factor Xa. Blood. Jul. 15, 1999;94(2):621-31.*
Joseph et al., "Snake Venom Prothrombin Activators Homologous to Blood Coagulation Factor Xa", *Haemostasis* 31:234-240 (2001).
Kini et al., "Scientific and Standardization Committee Communications: Classification and Nomenclature of Prothrombin Activators Isolated from Snake Venoms", (online) Jan. 26, 2001, http://www.med.unc.edu/isth/snake.htm.
Rosing et al., "Structural and Functional Properties of Snake Venom Prothrombin Activators", *Toxicon* 30(12):1515-1527 (1992).
Joseph J.S. et a l., 1999, *Blood*, 94 (2): 621-631.
Rao V.S. and Kini R. M., 2002, *Thrombosis and Haemostasis*, 88 (4): 611-619.
Rao V.S. et al., 2001, *Thrombosis and Haemostasis*, 2 (611).
Weinstein S.A. et al., 2001, *Toxicon*, 39 (12): 1937-1939.
Williams V., "The procoagulant from *Pseudonaja* species. Isolation and biochemical characterisation and comments on venom variability," *University of Adelaide*, 1999.
Masci P.P., et al., 1998, *Biochemistry International* Nov. 1988, 17 (5): 825-835.
Speijer H. et al., 1986, *Journal of Biological Chemistry*, 261 (28): 13258-13267.
Tans G. et al., 1985, *Journal of Biological Chemistry*, 260 (16): 9366-9372.
Kini R.M. et al., 2001, *Haemostasis*, 31 3-6): 218-224.
Chester A. and Crawford G.P.M., 1982, *ToxiconI*, 20 (2): 501-504.
Rao V.S. et al., 2003, *The Biochemical Journal*, 369 (3): 635-642.
St. Pierre L. et al., 2005, *Molecular Biology and Evolution*, 22 (9): 1853-1864.
Filippovich I. et al., 2005, *British Journal of Haemotolog*, 131 (2): 237-246.

* cited by examiner

*Primary Examiner*—Sheridan Swope
(74) *Attorney, Agent, or Firm*—King & Spalding

(57) ABSTRACT

The invention relates to snake venom protease polypeptides and nucleic acid sequences encoding same. This invention also relates to methods of making and using the snake venom proteases, e.g., to promote haemostasis and prevent blood loss such as during surgery or for treatment of wounds resulting from accidents and other types of injury or trauma.

27 Claims, 47 Drawing Sheets

Figure 1:
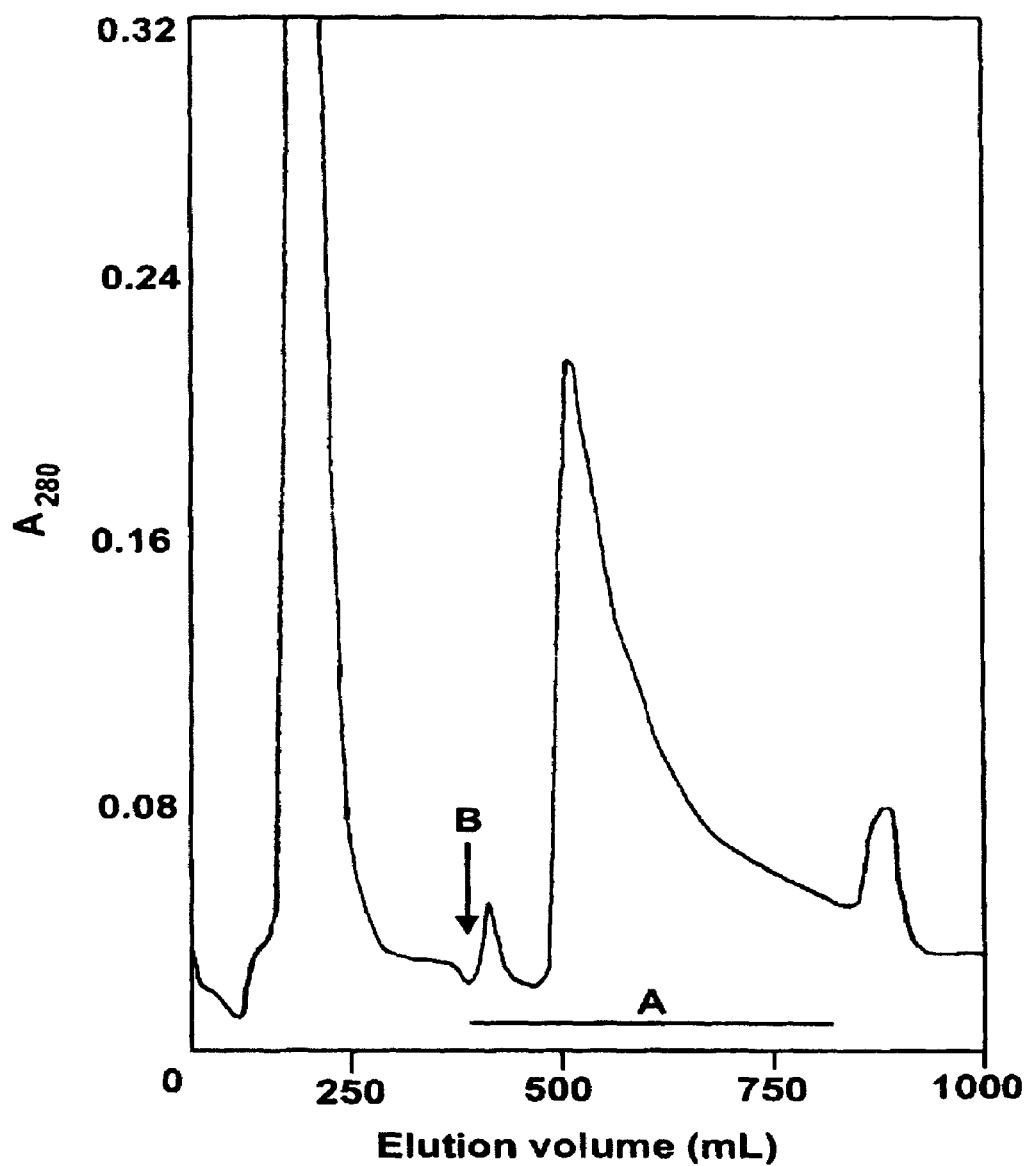

```
Brown SVP:        38   LTAAHC 43
Trocarin:         38   LTAAHC 43
Human factor Xa:  38   LTAAHC 43
```

FIG. 15

```
Brown SVP:   1   IVNGMDCKLGE 11
                 IVNGMDCKLGE
Trocarin:    1   IVNGMDCKLGE 11
```

FIG. 16

```
Brown SVP:         1   IVNGMDCKLGE 10
                       IV G  CK GE
Human factor Xa:   1   IVGGQECKDGE 10
```

FIG. 17

```
Brown SVP:   1   ANSLVEEFKSGNI 13
                   NSL EE   GNI
Trocarin:    1   SNSLFEEIRPGNI 13
```

FIG. 18

```
Brown SVP:       1    ANSLVEEFKSGN 12
                      ANS  EEFK GN
Mouse factor X:  41   ANSFFEEFKKGN 52
```

FIG. 19 atggctcctcaactactcctctgtctgatcctcacttttctgtggtctcccagagagctgaaagtaatgtattcttaaaagattt
cgcaaagaacaaaacgagctaattcactggttgaggaattaaatctggaaacattgaaaaggaatgcattgagggagatgttcaaaagaagaagc
caggaggtatttgaagatgaacgagaaaactgagacagaaaactgagaccttctggaatgttatgtagagatggggatcagtgttcatcaaaccctgtcattatcgcgg
gatatggaaagatggcactgtggtagctctgtacctgctgtctgcctatgaaggtaaacgtgaacgtgtcttatataagtctgcagagtggac
aatggtaactgtgtggcactctgcaaatctgttcaaaaacgatattcatgtcgctgaaggttaccttttgtgagagaggatgggcactcttgtgttgct
gggaggtaactttttcatgtggtagaaatatcaaaacaaggaagaagcaagtctgcctgacttgtgcagtccataatgcaactttgctgaaa
aaatctgataatccaagcccgatatcagaattgtaacgaatggactgcaaactgggtgaatgtccgtggcagcagtctgtagtgtgtgatgacaagaa
aggtgtgttttgtggaggaacaattttgagtccafctacgtgcttactgcagccactgcagcgagacgagacgattfcagttgttgtaggagaat
tagacagatcaagagcagaaaccgagaccttcttctgtggataagtatatgtgcataaaaattgttcctcccaaaaaagccaggaattcatgaa
aagtttgatcttgtcagctagctatgatagccatcaatgaagaccctatccagttctctgaaaatgtggttcctgcctgcctccacagct
gattttgccaaccaagtcctcatgaaacaagattttggcatcgttagtggttttcgaaagaggaaccgaactctaaaacacttaagtcctt
aaggtfcctatgtggacaggcacacctgcatgcttccaacactgcatccaactagtttctgctatgatactctgcctcaagatgcat
gccaaggagacagcggggggggcccacatcactgcatacagagataccccactttattactggattgtcagctgcagtgtgcacgaaa
ggcagatatggtatttacacacaaaattgtccaaaattcgtcaaaagtcgtcaaaagctacccagtacagagtcaagcactggtcgg
cctaa

FIG. 20A

MAPQLLLCLILTFLWSLPEAESNVFLKSRVANRFSQRTKRANSLVEEFKSGNIERECIEGR
CSKEEAREVFEDDEKTETFWNVYVDGDQCSSNPCHYRGIWKDGIGSYTCTCLSGYEGKN
CERVLYKSCRVDNGNCWHFCKSVQNDIQCSCAEGYLLGEDGHSCVAGGNFSCGRNIKT
RNKREASLPDFVQSHNATLLKKSDNPSPDIRIVNGMDCKLGECPWQAALVDDKKGVFCG
GTILSPIYVLTAAHCINETETISVVVGEIDRSRAETGPLLSVDKVYVHKFVPPKKSQEFYE
KFDLVSYDYDIAIIQMKTPIQFSENVVPACLPTADFANQVLMKQDFGIVSGFGGIFERGPN
SKTLKVLKVPYVDRHTCMLSSNFPITPTMFCAGYDTLPQDACQGDSGGPHITAYRDTHFI
TGIVSWGEGCARKGRYGIYTKLSKFIPWIKRIMRQKLPSTESSTGRL*

FIG. 20B

```
Brown      1    MAPQLLLCLILTFLWSLPEAESNVFLKSKVANRFLQRTKRANSLVEEFKSGNIERECIEE   60
Taipan     1    MAPQLLLCLILTFLWSLPEAESNVFLKSKVANRFLQRTKRANSLYEEFRSSNIEEECIEE   60
Red Belly  1    MAPQLLLCLILTFLWSLPEAESNVFLKSKVANRFLQRTKRSNSLEEEFRPGNIEECIEE   60
Tiger      1    MAPQLLLCLILTFLWSLPEAESNVFLKSKVANRFLQRTKRSNLEEIFPGNIEECIEE    60
Rough Scale 1   MAPQLLLCLILTFLWSLPEAESNVFLKSKVANRFLQRTKRSNLEEIFPCNIEECIEE    60
Trocarin   1    ----------------------------------------SNSIFEEIFPCNIEECIEE   20

Brown      61   RCSKEEAREVFEDDEKTETFWNVYYVDGDQCSSNPCHYRGICDGIGSYTCTCLSGYECHN  120
Taipan     61   RCSKEEAREVFEDDEKTETFWNVYYVDGDQCSSNPCHYRGICDGIGSYTCTCLSGYECHN  120
Red Belly  61   KCSKEEAREIFKDNEKTETFWNVYAYVDGDQCSSNPCHYCGCTCRDGIGSYTCTCLPNYECHN 120
Tiger      61   KCSKEEAREIFKDNEKTETFWNVYAYVDGDQCSSNPCHYCGCTCRDGIGSYTCTCLPNYECHN 120
Rough Scale 61  KCSKEEAREVFEDNEKTETFWNVYYVDGDQCSSNPCHYRGTCRDGIGSYTCTCLPNYECHN 120
Trocarin   21   KCSHEKAREVFFDNFKTETFWNVYYVDGDQCSSNPCHYPTCKDGICSYTCTCLPNYECHN  80

Brown      121  CERVLYKSCRVDNGNCWHFCKSVQNDIQCSCAEGYLLSEDGHSCVAGGNFSCGRNIKTRN  180
Taipan     121  CERVLYKSCRVDNGNCWHFCKPVQNDIQCSCAEGYLLGEDGHSCVAGGNFSCGRNIKTRN  180
Red Belly  121  CEHLFKSCRFFNGNCWHFCKPVQNDTQCSCAEGYLLGDDGHSCVAEDFSCGRNIKARN   180
Tiger      121  CEKVLFKSCRAFNGNCWHFCKRVQSETQCSCAEGYLLGDDGHSCVAEDFSCGRNIKARN  180
Rough Scale 121 CEKVLYQSCFVDNGNCWHFCKRVQSETQCSCAEGYRLGVDGHSCVAEDFSCGRNIARRN  180
Trocarin   81   CEKVLYQSCFVDNGNCWHFCKRVQSETQCSCAEGYRLGVDGHSCVAEDFSCGRNIARRN  140
```

FIG. 21A

FIG. 21B

```
Brown       361 SKTLKVLKVPYVDRHTCMLSSNFPITPTMFCAGYDTLPQDACQGDSGGPHITAYPDTHFI 420
Taipan      361 SKTLKVLKVPYVDPHTCMLSSNFSESPITPTMFCAGYDTLPRDACQGDSGGPHITAYPDTHFI 420
Red Belly   348 SNILKVIIVPYVDPHTCMLSDFRITPNMFCAGYDTLPQDACQGDSGGPHITAYPDTHFI 407
Tiger       358 SNILKVIIVPYVDPHTCMLSSNFRITQNMFCAGYDTLPQDACQGDSGGPHITAYPDTHFI 417
Rough Scale 360 SNILKVIIVPYVDPHTCMLSSDFRITQNMFCAGYDTLPQDACQGDSGGPHIAGIHFV 419
Trocarin    281 SNILKVIIVPYVDPHTCMLSSDFRITQNMFCAGYDTLPQDACQGDSGGPHITAYPDTHFI 340

Brown       421 TGIVSWGEGCARKGRYCIYTHLSKFIPWIRRIFRQALPSTESTGRL 467
Taipan      421 TGIVSWGEGCAQTGKYGVITKVSKFILMKRHMRQ-LPSTESTGRL 467
Red Belly   408 TGIISWGEGCARKGKYGVYTKVSNFIPWIPAV-RKHQPSTESTGRL 454
Tiger       418 TGIISWGEGCARKGKYGVYTKVSNFIPWINKIMSLR--------- 453
Rough Scale 420 TGIISWGEGCARKGKYGVYTKVSKFIPWIFKIMSLR--------- 455
Trocarin    341 TGIISWGEGCARKGKYGVYTKVSKFIPWINKIMSLR--------- 376
```

FIG. 21C

FIG. 22A

| | | | | | |
|---|---|---|---|---|---|
| Brown | 181 | KR------EASLPDFVQSH--NATLLKKSDNP-------------------SPD----IPIVNCMD | 215 |
| Taipan | 181 | KR------EASLPDFVQSQ--NAILLKKSDNP-------------------SPD----IPIVNCMD | 215 |
| Red Belly | 181 | KR------EASLPDFVQSQ--NATLLKKSDNP-------------------SPD----IPIVNCMD | 215 |
| Tiger | 181 | KR------EASLPDFVQSQ--KATVLKKSDNP-------------------SPD----IPIVNCMD | 215 |
| Rough Scale | 181 | KR------EASLPDFVQSQ--KATLLKKSDNP-------------------SPD----LRIVNCMD | 215 |
| Human FactorX | 181 | FRSVAQATSSSGEAPDSITWKPYDAADLDPTENPFDLLDFNQTQPERGDNNLTRIVGGQE | 240 |

| | | | | | |
|---|---|---|---|---|---|
| Brown | 216 | CKLGECPWQAALVDDKKGVFCGGTILSPIYVLTAAHCINETETISVVGEIDRSRAETG- | 274 |
| Taipan | 216 | CKLGECPWQAVLVDEKEDAFCGGTILSPIYVLTAAHCINQTMISVVGEINIGRKNPG- | 274 |
| Red Belly | 216 | CKLGECPWQAVLDKEGDVFCGGTILSPIYVLTAAHCITQSKHISVVGEIDISPKETR- | 274 |
| Tiger | 216 | CKLGECPWQAVLINEKGEVFCGGTILSPIHVLTAAHCINQTKSVIVCEIDISRKETR- | 274 |
| Rough Scale | 216 | CKLGECPWQAVLINEKGEVFCGGTILSPIHVLTAAHCINQTKSVIVCEIDISBKETR- | 274 |
| Human FactorX | 241 | CMDCECPWQALLINEENEGFCGGTILSEFYILTAAHCLYQAKRFKVRVQDRNTEQEEGGE | 300 |

| | | | | | |
|---|---|---|---|---|---|
| Brown | 275 | PLLSVDRVYVHKFVPPKKSQEFYEKFDLVSYDYDIAIIQMKTPIQFSENVVPACLPTAD | 334 |
| Taipan | 275 | RLLSVDKIYVHQKFVPPKKGYEFYEKFDLVSYDYDIALQMKTPIQFSENVVPACLPTAD | 334 |
| Red Belly | 275 | HLLSVDRAYVHKFVLAT--------YDYDIAIIQLKTPIQFSENVVPACLPTAD | 321 |
| Tig r | 275 | RLLSVDKIYVHKKFVPPNSYY-----QNIDRFAYDYDIAIIRMKTPIQFSENVVPACLPTAD | 331 |
| Rough Scale | 275 | RLLSVDKIYVHTKFVPPNYYY--VHQNFDRVAYDYDIAIIRMKTPIQFSENVVPACLPTAD | 333 |
| Human FactorX | 301 | AVHEVEVVIKHNRFTKET---------YDFDIAVLRLKTPITFRMNVAPACLPERD | 347 |

```
Brown           361 SKTLKVLKVPYVDRHTCGLLSNFPITPTMFCAGYLPGSGKDACQGDSGGPLICNGQFQGIVSWGGNPCGQPRKPGIYTRVTHYLPWIRQITGV 420
Coastal Taipan  361 SKTLKVLKVPYVDRHTCGLLSESPITPTMFCAGYLPGSGKDACQGDSGGPLICNGQFQGIVSWGGHPCGQPRKPGIYTRVTHYLPWIRQITGV 420
Inland Taipan   361 SNILKVTLK...........SESPITPTMYCAGYLEGSGKDTCQGDSGGPLICNGQFQGIVSWGEGCAQPNKPGVYTKVFDYLPWIRKHLKKT 420
Red Belly Black 348 SNILKVTI............SDFRITPTMFCAGYIEGGKDTCQGDSGGPLICNGQIQGIVSWGDGCAQKNKPGVYTKVFDYNPWIQAVIPHQPSTESSTGRL 454
Tiger           358 GNIVI...............QNFRIT...............GAGQGDSGGPLICNGQLHGVITSNGAEGCAQPGKPGIYTKVFDYLDWIKIHL 418
Rough Scale     360 GNIVI...............QDFRI..................GAGQGDSGGPLHCNGQLQGIVSWGEGCAQPRQFGVYTRVSKFIDWIEKSL 420

PROTHROMBIN ACTIVATING PROTEIN

This application claims the benefit of a previously filed Australian Provisional Application Nos. PS1483, filed Apr. 3, 2002, and 2003901033, filed Mar. 7, 2003, the contents of which are incorporated in their entirety.

FIELD OF THE INVENTION

The invention relates to novel snake venom protease polypeptides and nucleic acid sequences encoding same. This invention also relates to methods of making and using the snake venom proteases, e.g., to promote haemostasis and prevent blood loss such as during surgery or for treatment of wounds resulting from accidents and other types of injury or trauma.

BACKGROUND OF THE INVENTION

Haemostasis, commonly referred to as blood coagulation or blood clotting, is a key biological response to wounding or injury that prevents excessive blood loss. The biochemical cascade that controls haemostasis in mammals is well understood. A crucial step in this pathway is the activation of prothrombin by a prothrombinase complex to produce thrombin, which in turn activates Factor XIIIa, which cross-links fibrin to form a stable clot (Stubbs & Bode, 1994, Curr. Opin. Struct. Biol. 4 823-32).

In mammals, the prothrombin activator complex in vivo typically consists of a serine proteinase factor Xa and a cofactor Va formed on phospholipid membranes in the presence of calcium ions (Suttie & Jackson, 1977, Physiol. Rev. 57 1). The mammalian prothrombinase complex consists of a cofactor, Factor Va, and a serine protease, Factor Xa. Factor Xa alone activates prothrombin very slowly, however, in the presence of accessory proteins including the nonenzymatic cofactor Factor Va, calcium ions ($Ca^{2+}$) and phospholipid, prothrombin activation is enhanced many fold. In vivo, Factor Xa binds the phospholipid membrane of blood platelets by gamma-carboxyglutamic acid residues and has preferential cleavage for Arg274-Thr275 followed by Arg323-Ile324 bonds in prothrombin to form thrombin.

Given the importance of controlling blood loss during surgery or following injury or trauma, the identification of regulators that either promote blood clotting or inhibit the dissolution of clots (such as by the fibrinolytic plasmin/plasminogen pathway; Royston et al., 1990, Blood Coagul. Fibrinol. 1 53; Orchard et al., 1993, Br. J. Haematol. 85 596) has become an area of intense interest.

In particular, snake venoms have become useful sources of proteins that can either prevent fibrinolysis or promote blood clotting, as a result of blood loss during surgery, trauma in mammals.

For example, inhibitors of fibrinolysis have been isolated from venom of the Australian common brown snake *Pseudonaja textilis* (International Publication WO 99/58569). With regard to snake venom-derived prothrombin activators, reference is also made to Chinese Patent 1298017 which discloses prothrombin activators isolated from venom of the Taipan snake *Oxyuranus scutellatus*: prothrombin activating enzyme (designated Os-II) and activated factor Xa. The Chinese group proposed that to promote haemostasis such as in the case of a bleeding wound, Os-II is optimally added one hour before addition of factor Xa to thereby activate prothrombin. They proposed that the simultaneous action of the two can activate prothrombin and raise the yield of thrombin.

Reference is also made to Joseph et al., 1999, Blood 94 621 which discloses a factor Xa-like prothrombin activator (trocarin) isolated from the venom of the Australian rough-scaled snake *Tropidechis carinatus*. Trocarin forms a prothrombin activator complex that catalyzes formation of thrombin from prothrombin in vitro in the presence of phospholipid, factor Va and calcium ions.

Current haemostatic agents use bovine or human derived blood product components to replace various factors to prevent fibrinolysis or promote blood clotting, as a result of blood loss during surgery, trauma in mammals. The use of bovine or human derived blood product components may potentially expose patients to viral contamination or other adverse events.

SUMMARY OF THE INVENTION

The invention is based, in part, on the discovery of prothrombin activating polypeptides, referred to herein as "snake venom proteases or SVP's," which are factor independent. The snake venom proteases share certain amino acid sequences similarity to the amino acid sequences of factor Xa and trocarin which are prothrombin activators that require calcium, phospholipids and factor Va for activation. However, the snake venom proteases of the invention are complete or partially complete prothrombin activators and thus do not have the cofactor requirements of human factor Xa or trocarin. In other words, they can process prothrombin to thrombin in the absence of cofactors such as calcium, phospholipids and/or factor Va. For example, snake venom proteases from brown, coastal taipan and inland taipan venom are complete prothrombin factors in that they can process prothrombin to thrombin in the absence of calcium, phospholipids and factor Va. These SVP's appear to include an internal domain, residues 292-305 of FIG. 23, which makes them independent of host supplied Factor Va. Snake venom proteases from, for example, red belly, tiger and rough scale snake venom are partially complete prothrombin activators in that they can process prothrombin in the absence of calcium and phospholipids but require the presence of factor Va. In addition, preferred SVP's of the invention can cleave descarboxy prothrombin, which is a poor substrate for human factor X.

Accordingly, in one aspect, the invention features snake venom protease polypeptides, and biologically active or antigenic fragments thereof, that are complete or partially complete prothrombin activators and that are useful, e.g., as reagents to increase coagulation. In another embodiment, the invention provides snake venom protease polypeptides having prothrombin activating activity.

In one embodiment, the snake venom protease includes one or more of a light chain and a heavy chain or biologically active fragments thereof. Preferred light and heavy chain proteins are the same or very similar (differing, e.g., by 1 or 2 residues) in length as naturally occurring species. In another embodiment, the snake venom proteases include a propeptide, a light chain, an activation peptide and a heavy chain. All processing intermediates, whether or not present in nature, are within the invention. Thus, in yet another embodiment, the snake venom protease polypeptides of the invention include a light chain, an activation peptide and a heavy chain. The preferred embodiment includes a light chain and heavy chain from which the propeptide domain and activation peptide or peptides have been cleaved. Purified preparations can include or have the cleaved propeptide domains and cleavage fragments purified away.

In a preferred embodiment, the complete or partially complete prothrombin activating SVP includes one or more and in some cases all of the following domains (the numbering refers to the consensus numbering in FIG. 23):

a first or propeptide domain which corresponds to residues 1-40 of FIG. 23. In preferred embodiments, this domain can have at least 31, 40, 80, 90, 95, or 98% sequence similarity with, or differ at no more than 1, 2, 3, 5, or 10 amino acid residues from, the corresponding domain of any of the 5sequences presented in FIG. 29, and in particular to the corresponding domain of one of the complete SVP's, namely the Brown, Coastal Taipan, or Inland Taipan sequence, or one of the partially complete SVP's, namely the Red Belly Black, Tiger, or Rough Scale. Preferred active products will of course lack the propeptide domain. It may in some cases be desirable to modify the snake propeptide domain to make it more similar to the propeptide domain of human factor X, or to replace the snake propeptide domain with a human propeptide domain. The propeptide domains are 100% conserved in all 6 snakes with the exception of a single amino acid change V→E in the Red Bellied Black. Comparison with the corresponding human sequence reveals 12/40 identical residues (30% identity). The majority of the conserved residues are hydrophobic;

a light chain cleavage site between residues 40 and 41 of FIG. 23;

a domain which corresponds to residues 41-85 of FIG. 23. This domain may be functionally analogous to the GLA (gamma carboxy glutamic acid) domain of human factor X. In preferred embodiments, this domain can have at least 71, 75, 80, 85, 90, 95 or 98% sequence similarity with, or differ at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In some embodiments, it may be desirable to conserve one or more of the 11 glutamic acid residues in this region. Ten of these are conserved between the human factor X sequence and all 6 of the snake sequences including residues 46/47, 54, 56, 59/60 65/66, 69, 72. Note that 79 is also gamma-carboxylated in human and there are 2 other potential sites in all 6 snake sequences of FIG. 23 at residues 76 and 78. In many embodiments, the initial residue of this domain is the initial residue of the light chain of the product. In a preferred embodiment, this domain shares at least 85% sequence identity with the corresponding domain of one of the six snake venom proteases disclosed herein;

a domain which corresponds to residues 86-122 of FIG. 23. This domain may be functionally analogous to the first EGF domain of human factor X. In preferred embodiments, this domain can have at least 71, 75, 80, 90, 95 or 98% sequence similarity with, or differ at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. Identity with snake consensus is 25/37. The domain has 70% identity with the human sequence. In a preferred embodiment, this domain shares at least 70% sequence identity with the corresponding domain of one of the six snake venom proteases disclosed herein;

a domain which corresponds to residues 123-165 from any of the 6 snake sequences of FIG. 23. This domain may be functionally analogous to the second EGF domain of human factor X. In preferred embodiments, this domain can have at least 36, 50, 75, 80, 90, 95 or 98% sequence similarity with, or differ at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. Identity with snake consensus is 15/43. The domain as 35% identity with the human sequence. In a preferred embodiment, this domain shares at least 50% sequence identity with the corresponding domain of one of the six snake venom proteases disclosed herein;

a domain which corresponds to residues 166-179 from among the 6 snake sequences of FIG. 23. In preferred embodiments, this domain can have at least 75, 80, 90, 95 or 98% sequence similarity with, or differ at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 70% sequence identity with the corresponding domain of one of the six snake venom proteases disclosed herein;

a domain which corresponds to residues 180-182 of FIG. 23. In preferred embodiments, this domain can have at least 1, 2, or 3 resides which are the same as seen in any of the 6 sequences presented in FIG. 23. This domain is preferably absent in an active product;

a domain which corresponds to residues 183-209 of FIG. 23. This domain may be functionally analogous to the activation peptide in human factor X. In preferred embodiments, this domain can have at least 17, 50, 75, 80, 90, 95 or 98% sequence similarity with, or differ at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. Identity with snake consensus sequences is 8/51. There is 16% identity with the human sequence. This is the region that is cleaved out when processing the light and heavy chains of the protease, and is preferably not present in active products. The sequence is 51 amino acids for human factor X and 27 for each of the snakes. In a preferred embodiment, this domain shares at least 50% sequence identity with the corresponding domain of one of the six snake venom proteases disclosed herein;

a heavy chain which corresponds to residues 210-467 (in the case of the Brown, Coastal Taipan, Inland Taipan, or Red Belly Black sequence) or 456 (in the case of the Tiger and Rough Scale sequence) of FIG. 23. This domain may be functionally analogous to the heavy chain in human factor X. In preferred embodiments, this domain can have at least 50, 75, 80, 90, 95 or 98% sequence similarity with, or differs at no more than 1, 2, 3, 5, or 10 amino acid residues from, the corresponding domain of any of the 6 sequences presented in FIG. 23, and in particular to the corresponding domain of one of the complete SVP's of, namely the Brown, Coastal Taipan, or Inland Taipan sequence, or one of the partially complete SVP's, namely the Red Belly Black, Tiger, or Rough Scale. Identity with snake consensus sequences is 135/268 giving a 50% identity with the human sequence. The catalytic domain of human factor X contains an essential active site triad $H_{236}$, $D_{282}$ and $S_{379}$. These 3 residues are conserved in all 6 snakes as $H_{251}$, $D_{309}$ and $S_{406}$ in FIG. 23 and are conserved in preferred embodiments of the SVP's of the invention. Amino acids 292-305 appear to contribute factor Va like activity and the sequence, or one having differing by no more than 1, 2, 3, 4, or 5 residues from a sequence of 292-305 should be present in complete SVP's. In a preferred embodiment, this domain shares at least 75% sequence identity with the corresponding domain of one of the six snake venom proteases disclosed herein.

As is alluded to above, a preferred embodiment will include a dimeric molecule of a fully processed light chain and heavy chain, which have been cleaved from the propeptide domain and activation or cleavage domains. In preferred embodiments the light chain includes intra chain Cys-Cys linkages between 57 and 62, 90 and 101, 95 and 110, 112 and 121, 129 and 140, and/or 151 and 164 of the light chain, intra chain Cys-Cys linkages between 216 and 221, 236 and 252, 377 and 391, and/or 402 and 430 of the heavy chain, and inter chain Cys-Cys linkages between 172 of the light chain and 329 of the heavy chain. In preferred embodiments, the SVP is a complete or partially complete prothrombin activator in that it shows significantly greater activity in the absence of cofactors than does an incomplete activator, e.g., human factor X or trocarin. Preferably, the activity of the complete or partially complete prothrombin activator is at least 1.5, 2, 4, 10, 15, 20, 50, or 100 fold (two orders of magnitude) higher than that of an incomplete activator, e.g., human factor Xa, or trocarin, alone. This comparison is made between a snake venom protease and an incomplete activator measured under the same or similar conditions, e.g., in the absence of Ca and phospholipids. In preferred embodiments, the % of activity (i.e., the activity of the complete or partially complete activator in the absence of Ca and phospholipid as a % of that seen with the same activator in the presence of Ca and phospholipids) of a complete or partially complete is at least 1.5, 2, 4, 10, 15, 20, 50, 100, 1000 or 4000 fold greater than the same % shown by an incomplete activator, e.g., human factor X or trocarin. Preferred complete or partially complete activators will clot citrated plasma at concentration of about $10^{-10}$ to $10^{-06}$ M, e.g., at $10^{-8}$ or $10^{-7}$ M, giving clotting times of about 50 to 15 seconds, demonstrating $Ca^{2+}$ and phospholipid independence. Accordingly, the prothrombin activator shows kinetic properties of cofactor independence (calcium ions and/or phospholipid) in the concentration range of about $10^{-10}$ to $10^{-06}$ M concentration range being a suitable working range to reduce blood loss.

In a preferred embodiment, the complete or partially complete prothrombin activating SVP includes one or more and in some cases all of the following domains (the numbering refers to the numbering in FIG. 22):

a first or propeptide domain which corresponds to residues 1-40 from among the five snake sequences of FIG. 22 (or the corresponding sequence of Inland Taipan). In preferred embodiments this domain can have at least 31, 40, 80, 90, 95, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. Preferred active products will of course lack the propeptide domain;

a domain which corresponds to residues 41-120 from the five snake sequences of FIG. 22 (or the corresponding sequence of Inland Taipan) having at least 67, 90, 95, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 90% sequence identity with the corresponding domain of one of the six snake venom proteases disclosed herein;

a domain which corresponds to residues 121-132 from among the five snake sequences of FIG. 22 (or the corresponding sequence of Inland Taipan) having at least 43, 60, 65 80, 85, 90, 96, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 60% sequence identity with the corresponding domain of one of the six snake venom proteases disclosed herein;

a domain which corresponds to residues 133-182 from among the five snake sequences of FIG. 22 (or the corresponding sequence of Inland Taipan) having at least 80, 85, 90, 96, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 80% sequence identity with the corresponding domain of one of the six snake venom proteases disclosed herein;

a domain which corresponds to residues 183-233 from among the snake sequence of FIG. 22 (or the corresponding sequence of Inland Taipan) having at least 17, 30, 50, 95, 96, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale; Preferred active products will of course lack the activation domains. In a preferred embodiment, this domain shares at least 90% sequence identity with the corresponding domain of one of the six snake venom proteases disclosed herein;

a domain which corresponds to residues 234-378 from among the five snake sequences of FIG. 22 (or the corresponding sequence of Inland Taipan) having at least 80, 85, 90, 96, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 80% sequence identity with the corresponding domain of one of the six snake venom proteases disclosed herein;

a domain which corresponds to residues 379-394 from among the five snake sequences of FIG. 22 (or the corresponding sequence of Inland Taipan) having at least 39, 30, 50, 80, 85, 90, 96, or 98% sequence similarity with, or differ at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 50% sequence identity with the corresponding domain of one of the six snake venom proteases disclosed herein;

a domain which corresponds to residues 395-456 from among the five snake sequences of FIG. 22 (or the corresponding sequence of Inland Taipan) having at least 80, 85, 90, 96, or 98% sequence similarity with, or differs at no more than 1, 2, 3, 5, or 10 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 80% sequence identity with the corresponding domain of one of the six snake venom proteases disclosed herein;

a domain which corresponds to residues 457-467 from among the five snake sequences of FIG. 22 (or the corresponding sequence of Inland Taipan) which can be absent, or if present, has at least 90, 96, or 98% sequence similarity with, or differs at no more than 1, 2, 3, or 5 amino acid residues from, the corresponding domain of any of the 5 sequences presented in FIG. 22 (or the corresponding sequence of Inland Taipan), and in particular to the corresponding domain of one of the complete SVP's of, namely the Brown, Coastal Taipan, or Inland Taipan sequence, or one of the partially complete SVP's, namely the Red Belly Black, Tiger, or Rough Scale. In a preferred embodiment, this domain shares at least 90% sequence identity with the corresponding domain of one of the six snake venom proteases disclosed herein;

As is alluded to above, a preferred embodiment will include a dimeric molecule of a fully processed light chain and heavy chain, which have been cleaved from the propeptide domain and activation or cleavage domains. In preferred embodiments the light chain includes intra chain Cys-Cys linkages between 57 and 62, 90 and 101, 95 and 110, 112 and 121, 129 and 140, and/or 151 and 164 of the light chain, intra chain Cys-Cys linkages between 216 and 221, 236 and 252, 377 and 391, and/or 402 and 430 of the heavy chain, and inter chain Cys-Cys linkages between 172 of the light chain and 329 of the heavy chain. In preferred embodiments, the dimeric SVP is a complete prothrombin activator. In others, it is a partially complete prothrombin activator. In preferred embodiments, the SVP is a complete or partially complete prothrombin activator in that it shows significantly greater activity in the absence of cofactors than does an incomplete activator, e.g., human factor X or trocarin. Preferably, the activity of the complete or partially complete prothrombin activator is at least 1.5, 2, 4, 10, 15, 20, 50, 100, 1000, or 4000 fold (two to four orders of magnitude) higher than that of an incomplete activator, e.g., human factor Xa, or trocarin, alone. This comparison is made between a snake venom protease and an incomplete activator measured under the same or similar conditions, e.g., in the absence of Ca and phospholipids. In preferred embodiments, the % of activity (i.e., the activity of the complete or partially complete activator in the absence of Ca and phospholipid as a % of that seen with the same activator in the presence of Ca and phospholipids) of a complete or partially complete is at least 1.5, 2, 4, 10, 15, 20, 50, 100, 1000, or 4000 fold greater than the same % shown by an incomplete activator, e.g., human factor X or trocarin. Preferred complete or partially complete activators will clot citrated plasma at concentration of about $10^{-10}$ to $10^{-06}$ M, e.g., at $10^{-8}$ or $10^{-7}$ M, giving clotting times of about 50 to 15 seconds, demonstrating $Ca^{2+}$ and phospholipid independence. Accordingly, the prothrombin activator shows kinetic properties of cofactor independence (calcium ions and/or phospholipid) in the concentration range of about $10^{-10}$ to $10^{-06}$ M concentration range being a suitable working range to reduce blood loss.

The SVP's of the invention do not include trocarin, shown for example in FIG. 21. In preferred embodiments, the processed light chain of a complete SVP will differ from the processed light chain of trocarin by at least 1, 3, 5, 10, 15 or 20 residues. In preferred embodiments, the processed heavy chain of a complete SVP will differ from the processed heavy chain of trocarin by at least 5, 10, 15, 20 or 30 residues. (differ means differ in identity or by insertion or deletion, unless otherwise indicated).

In preferred embodiments, the sequence of a complete SVP of the invention will have one or more of the following properties, it will be other than serine at residue 41 (all references are to the numbering of FIG. 21), isoleucine at residue 48, proline at residue 50, asparginine at residue 74, proline at residue 104, asparginine at residue 105, lysine at residue 123, glutamine at residue 127, arginine at residue 142, serine, glutamic acid, threonine at residues 145-7, serine at residue 154, arginine at residue 156, valine at residue 159, glutamic acid at residue 167, aspartic acid at residue 169, alanine at residue 178; will include at least one residue from the sequence 181-208 any of the Brown, Taipan, Red Belly, Tiger, Rough Scale sequences of FIG. 21 (or a corresponding residue from Taipan Inland); will be other than isoleucine at residue 228, asparginine at residue 229, glycine at residue 233, glutamic acid at residue 232, histidine at residue 245, serine, valine at residues 258-9; will include at least one residue from the sequence 260-270 any of the Brown, Taipan, Red Belly, Tiger, Rough Scale sequences of FIG. 21 (or a corresponding residue from Taipan Inland); will be other than arginine at residue 274, threonine at residue 286, asparganine-tyrosine-tyrosine-tyrosine-valine-histidine-glutamine-asparganine at residues 292-300, arginine at residue 303, alanine at residue 305, arginine at residue 314, glutamic acid at residue 338, serine at residue 345, RIQFKQPT at residues 353-360, isoleucine at residue 367, threonine at residue 368, aspartic acid at residues 382, arginine at residue 384, glutamine at residue 387, asparginine at residues 389, isoleucine at residue 424, arginine at residue 342, lysine at residues 451, serine, leucine at residue 454-455; or will include at least one residue from the sequence 457-467 of any of the Brown, Taipan, Red Belly, Tiger, Rough Scale sequences of FIG. 21 (or a corresponding residue from Taipan Inland);

In preferred embodiments, the processed light chain of a partially complete SVP will differ from the processed light chain of trocarin by at least 1, 3, 5, 10, or 15 residues. In preferred embodiments, the processed heavy chain of a complete SVP will differ from the processed heavy chain of trocarin by at least 5, 10, 15, 20 or 30 residues. In preferred embodiments, the sequence of a partially complete SVP of the invention will include at least one residue from the sequence 181-208 any of the Brown, Taipan, Red Belly, Tiger, Rough Scale sequences of FIG. 21 (or a corresponding residue from Taipan Inland); or will include at least one residue from the sequence 260-270 any of the Brown, Taipan, Red Belly, Tiger, Rough Scale sequences of FIG. 21 (or a corresponding residue from Taipan Inland).

In a preferred embodiment, the SVP is a complete prothrombin activator and includes one or both of a light chain having at least 87, 89 or 90% sequence identity with, or differs at not more than 16, 14, or 13 residues from: the consensus sequence of FIG. 24 or a heavy chain that has at least 82, 85 and 84% identity or differs at not more than 45, 39, or 40 residues from the consensus sequence of FIG. 24.

In preferred embodiments, the complete SVP includes one or both light and heavy chain which is identical with or has at least 84, 86 or 86% sequence identity with, or differs at no more than 61 or 53 residues from, the sequence of Brown, Coastal Taipan, or Inland Taipan SVP sequence shown in FIG. 24.

In a preferred embodiment the SVP is a partially complete prothrombin activator and includes one or both of a light and heavy chain having at least 84% sequence identity with, or differs at not more than 61 or 53 residues from: the sequence of FIG. 24

In preferred embodiments the partially complete SVP includes one or both of a light and heavy chain which is identical with or has at least 84, 80 or 82% sequence identity with, or differs at no more than 61, 76, 68 residues from, the sequence of Red Belly Black, Tiger, or Rough Scale SVP sequence shown in FIG. 24.

In other embodiments, the invention provides snake venom protease polypeptides, e.g., a polypeptide: having the amino acid sequence shown in SEQ ID NOs:2, 5, 8, 11, 14 or 17, or the amino acid sequence encoded by the nucleic acid of SEQ ID Nos: 1, 3, 4, 6, 7, 9, 10, 12, 13, 15, 16, or 18; an amino acid sequence that is substantially identical to the amino acid sequence shown in SEQ ID NOs:2, 5, 8, 11, 14 or 17, or the amino acid sequence encoded by the nucleic acid of SEQ ID Nos: 1, 3, 4, 6, 7, 9, 10, 12, 13, 15, 16, or 18; or a sequence which has at least 85, 90, 95, 98 or 99% sequence identity with, or which differs at no more than 1, 2, 5, 10, 15, or 20 residues from, one of the recited amino acid sequences.

In other embodiments, the invention provides snake venom protease light chain polypeptides, e.g., a polypeptide: having the amino acid residues 41 to 179 (the numbering refers to the numbering in FIG. 23) of any of the amino acid sequences shown in SEQ ID NOs:2, 5, 8, 11, 14 or 17, or the amino acid residues 41 to 179 of the amino acid sequence encoded by the nucleic acid of SEQ ID Nos: 1, 3, 4, 6, 7, 9, 10, 12, 13, 15, 16, or 18; an amino acid sequence which is substantially identical to amino acid residues 41 to 179 of the amino acid sequence shown in SEQ ID NOs:2, 5, 8, 11, 14 or 17, or the amino acid sequence encoded by the nucleic acid of SEQ ID Nos: 1, 3, 4, 6, 7, 9, 10, 12, 13, 15, 16, or 18; or a sequence which has at least 85, 90, 95, 98 or 99% sequence identity with, or which differs at no more than 1, 2, 5, 10, 15, or 20 residues from, one of the recited amino acid sequences.

In other embodiments, the invention provides snake venom protease heavy chain polypeptides of the amino acid sequence shown in SEQ ID NOs:2, 5, 8, 11, 14 or 17, or encoded by SEQ ID Nos: 1, 3, 4, 6, 7, 9, 10, 12, 13, 15, 16, or 18; an amino acid sequence which is substantially identical to amino acid residues of said heavy chains in SEQ ID NOs:2, 5, 8, 11, 14 or 17, or the amino acid sequence encoded by the nucleic acid of SEQ ID Nos: 1, 3, 4, 6, 7, 9, 10, 12, 13, 15, 16, or 18; or a sequence which is at least 85, 90, 95, 98 or 99% sequence identity with, or which differs at no more than 1, 2, 5, 10, 15, or 20 residues from, one of the recited amino acid sequences.

In a related aspect, the invention further provides nucleic acid constructs which include a snake venom protease nucleic acid molecule described herein.

In a related aspect, the invention provides snake venom protease polypeptides or fragments operatively linked to non-snake venom protease polypeptides to form fusion proteins. In one embodiment, the sequence encoding one or more or the light chain of a snake venom protease, an activator polypeptide, and a heavy chain venom protease can be linked to a sequence encoding a propeptide of a non-snake venom prothrombin activating polypeptide, e.g., a human factor Xa propeptide encoding sequence. In another embodiment, the sequence encoding the light chain of a snake venom protease and the sequence encoding the heavy chain of a snake venom protease can be linked to each other by a nucleic acid sequence encoding an activator peptide of a non-snake venom prothrombin activating polypeptide, e.g., a human factor Xa activator peptide encoding sequence. In other embodiments, an SVP sequence can be fused to a sequence, preferably easily cleavable, which allows isolation, e.g., fused to a GST moiety or to an epitope tag.

In another aspect, the invention features an isolated protein comprising an amino acid sequence selected from any or all of the group consisting of:

| | |
|---|---|
| KREASLPDFVQS; | [SEQ ID NO: 19] |
| LKKSDNPSPDR; and | [SEQ ID NO: 20] |
| SV$X_1$VGEI$X_2$$X_3$SR. | [SEQ ID NO: 21] |

$X_1$, $X_2$ and $X_3$ may be any amino acid.

Preferably, $X_1$ is either valine or isoleucine, $X_2$ is either asparginine or aspartic acid and $X_3$ is either arginine, lysine or isoleucine.

In one embodiment, the isolated protein further comprises an amino acid sequence selected from the group consisting of:

| | |
|---|---|
| MAPQLLLCLILTFLWSLPEAESNVFLKSK and | [SEQ ID NO: 22] |
| ANRFLQRTKR | [SEQ ID NO: 23] |

In a particular embodiment, said prothrombin activating protein of the invention is isolated from snake venom. Preferably, said prothrombin activating protein of the invention is obtainable from venom of an Australian snake selected from the non limiting group consisting of: taipan (*Oxyuranus scutellatus*), mainland tiger (*Notechis scutatus*), rough scaled (*Tropidechis carinatus*), red-belly black snake (*Pseudechis porphyriacus*), and any brown snake of the genus *Pseudonaja*, wherein any brown snake includes the common brown snake (*Pseudonaja textilis*). Throughout the present application, the term "Brown" (capital letter "B") with reference to a snake venom refers to snake venom from the common brown snake, also known as *P. textilis*. When reference is being made to "any brown snake", the genus *Pseudonaja* is indicated.

In another aspect, the invention features an isolated nucleic acid that encodes a snake venom protease polypeptide or biologically active fragment thereof as described herein. In a preferred embodiment, the isolated nucleic acid molecule encodes a polypeptide having the amino acid sequence of SEQ ID NOs:2, 5, 8, 11, 14 or 17. In other embodiments, the invention provides isolated nucleic acid molecules having the nucleotide sequence shown in SEQ ID NOs:1, 3, 4, 6, 7, 9, 10, 12, 13, 15, 16 or 18, or a full complement of SEQ ID NOs:1, 3, 4, 6, 7, 9, 10, 12, 13, 15, 16 or 18. In still other embodiments, the invention provides nucleic acid molecules that are substantially identical (e.g., naturally occurring allelic variants) to the nucleotide sequence shown in SEQ ID NOs:1, 3, 4, 6, 7, 9, 10, 12, 13, 15, 16 or 18. In other embodiments, the invention provides a nucleic acid molecule which hybridizes under a stringency condition described herein to a nucleic acid molecule comprising the nucleotide sequence of SEQ ID NOs:1, 3, 4, 6, 7, 9, 10, 12, 13, 15, 16 or 18, wherein the nucleic acid encodes a full length snake venom protease polypeptide or an active fragment thereof.

In a related aspect, the invention further provides nucleic acid constructs that include a nucleic acid molecule encoding a snake venom protease or portion thereof, e.g., as described herein. In certain embodiments, the nucleic acid molecules of the invention are operatively linked to native or heterologous regulatory sequences. In other embodiments, the nucleic acid molecule includes a nucleic acid encoding a propeptide, a nucleic acid sequence encoding a light chain of a snake venom protease, a nucleic acid sequence encoding an activator peptide, a nucleic acid sequence encoding a heavy chain of a snake venom protease, wherein one or more of the sequence encoding the propeptide and the sequence encoding the activator peptide is not from a snake venom protease. For example, one or more of the sequence encoding the propeptide and activator peptide can be from a mammalian prothrombin activator, e.g., a human prothrombin activator, e.g., human factor Xa. Also included, are vectors and host cells containing the nucleic acid molecules of the invention e.g., vectors and host cells suitable for producing snake venom protease nucleic acid molecules and polypeptides.

In another related aspect, the invention provides nucleic acid fragments suitable as primers or hybridization probes for the detection or amplification of snake venom protease-encoding nucleic acids. For example, the invention includes primers spaced apart to amplify: a full-length snake venom protease, e.g., a snake venom protease described herein, or any domain or region of a snake venom protease described herein.

In still another related aspect, isolated nucleic acid molecules that are antisense to a snake venom protease-encoding nucleic acid molecule are provided.

The invention also contemplates biologically active fragments, variants, derivatives and homologs of the aforementioned isolated proteins and nucleic acids of the invention.

In another aspect, the invention features an antibody that binds an isolated snake venom protease polypeptide, e.g., a snake venom protease polypeptide described herein. In one embodiment, the antibody can bind to: the propeptide of a snake venom protease polypeptide or fragments thereof described herein, a light chain of a snake venom protease polypeptide or fragment thereof described herein, an activator polypeptide of a snake venom protease polypeptides or fragments thereof described herein, or a heavy chain of a snake venom protease polypeptide or fragment thereof described herein. In another embodiment, the antibody can bind a portion of a snake venom protease which includes both the light and heavy chains of a snake venom protease polypeptide described herein. Antibodies can be used, e.g., to isolate snake venom proteases from a sample.

In another aspect, the invention features a pharmaceutical composition which includes an isolated snake venom protease polypeptide or biologically active fragment thereof, e.g., an isolated snake venom protease polypeptide described herein, and a pharmaceutically acceptable carrier, diluent or excipient. In one embodiment, the composition, e.g., pharmaceutical composition, has a pH of about 5 to 9, preferably about 6.5 to 7. The composition, e.g., pharmaceutical composition, can further include, e.g., a stabilizer, such as a polyol. In such embodiments, the composition, e.g., pharmaceutical composition can include about 5%, 10%, 20% or more of a polyol (or polyols). An example of a polyol which can be used in the composition is glycerol. In some embodiments, the composition, e.g., pharmaceutical composition, does not include a co-factor. In another embodiment, the composition, e.g., pharmaceutical composition can include one or more co-factors, e.g., one or more of calcium, phospholipid and factor Va.

In another aspect, the invention provides methods of screening for agents, e.g., compounds such as co-factors, that modulate the activity of the snake venom polypeptides, e.g., compounds that modulate blood coagulation response and/or processing of prothrombin to thrombin. In one embodiment, the method can include providing a reaction mixture of prothrombin and a snake venom protease, e.g., a snake venom protease described herein, and contacting the reaction mixture with one or more co-factors (e.g., one or more of calcium, a phospholipid, factor Va and a vitamin, e.g., vitamin K). The reaction mixture can further include, e.g., fibrinogen. The method can further include comparing the activity of the snake venom protease on prothrombin processing in the absence and presence of the agent, e.g., the co-factor. In another embodiment, the method includes providing a sample (e.g., a blood sample) and contacting the sample with a snake venom protease in the absence and presence of an agent, e.g., a co-factor, and comparing the effect of the co-factor on coagulation by the snake venom protease. In yet another embodiment, the method can include contacting platelets with a snake venom protease in the absence and presence of an agent, e.g., a co-factor, to determine the effect of the agent on platelet activation.

In one embodiment, the invention features a method of measuring the level of activity by Citrate anticoagulated whole blood or its plasma fraction that can be used to measure the activity of the snake venom polypeptide (protease) by determining the time for a solid clot to form. The measurement can be carried out manually or by any of the automated coagulation measuring devices. Furthermore, the activity of the protease can also be measured by using tetrapeptides with a linked p-nitroanilide (chromogenic substrates) which resemble specific domains of its substrate (prothrombin). This assay is a simple calorimetric measurement of rate of formation of p-nitroaniline in solution in a substrate independent mixture.

In another aspect, the invention features a method of treating a subject, e.g., by inducing haemostasis. The method includes administering a snake venom protease of the invention to a subject, thereby treating the subject, e.g., by inducing haemostasis.

In a preferred embodiment, the subject is treated to inhibit bleeding from a site on or in the subject's body. The treatment can be used to inhibit bleeding which can occur in connection with medical treatment, e.g., surgery. In other embodiments a wound, trauma or other event is treated.

In some embodiments, the subject has a deficiency in the ability to form or maintain a blood clot. This deficiency can be due to a genetic defect or can be the result of medical treatment, e.g., the administration of a drug which reduced the ability of the subject to form or maintain a blood clot, e.g., coumadine or Warfarin.

In one embodiment, the snake venom protease is administered by a person other than the subject, while in other embodiments the snake venom protease is self-administered. The person other than the subject can be a health car provider but in some cases will not be a health care provider. For example, in some embodiments, the product will be used to treat battlefield trauma and will be administered by a person other than a health care provider.

In some embodiments, the snake venom protease is provided to the subject in advance of a need to use it, e.g., in the case of subject has a deficiency in the ability to form or maintain a blood clot or in the case of an individual who is believed to be at risk for a traumatic wound, e.g., military personnel, persons working with dangerous machinery, or generally those working in hazardous occupations, such as farming or mining. The snake venom protease can be supplied with written, recorded audio or video, or oral instructions on its use.

In some embodiments the snake venom protease will be provided in a form which allows the user (the subject or one who administers it to the subject) to administer a measured dose. Thus, the snake venom protease can be disposed in dispensing device, e.g., a device which dispenses liquid, droplets, aerosols, dry powder and the like, preferably in a metered dosage.

In another aspect, the invention provides a method of activating prothrombin. The method includes contacting prothrombin with a snake venom protease of the invention, to thereby activate said prothrombin. The prothrombin can be activated in vitro or in vivo. In one embodiment, the prothrombin can include descarboxyprothrombin.

In particular embodiments, the pharmaceutical compositions and methods of inducing haemostasis and/or prothrombin activation can be used to prevent of blood loss from a wound. One such embodiment, the composition may be that of a tissue sealant and/or a fibrin glue. It is also contemplated that antifibrinolytic agents may form part of such an embodiment. Anti fibrinolytic agents may be selected from a non-limiting group including textilinin (International Publication WO 99/58569), aprotinin and EACA, any of which may be added to prevent lysis of the blood clot through the inhibition of the action of plasmin or activators of plasmin.

In another aspect, the invention features a method of obtaining a protein, nucleic acid, or library, or nucleic acid or protein sequence information, e.g., as described herein. For example obtaining a snake protein, e.g., an SVP, e.g., an SVP described herein, or nucleic acid encoding a snake protein, e.g., a nucleic acid encoding an SVP, e.g., an SVP described herein or any of the libraries described herein. These are referred to herein as "collection-based methods." The method includes: collecting an Australian snake selected from the non-limiting group consisting of a *Pseudonaja textilis, Pseudonaja nuchalis, Pseudonaja affinis, Pseudonaja inframacula, Oxyuranus scutellatus, Oxyuranus microlepidotus, Notechis scutatus, Notechis ater niger, Notechis ater serventyi, Hoplocephalus stephansii, Pseudechis porphiracus, Australaps surperba, Tropedechis carinatus* (or collecting tissue from or produced by such a snake, e.g., eggs, or discarded tissue such as a molted skin) and obtaining a protein, nucleic acid, or library from the snake or from the progeny of the snake, or obtaining sequence data from a protein or nucleic acid from the snake, or from the progeny of the snake.

The method can include collecting a dead Australian snake or capturing a live Australian snake or a live damaged Australian snake. In one embodiment, the method further includes obtaining a sample from the snake, e.g., obtaining a venom sample from the snake, and obtaining the protein, or library of proteins, from the sample, e.g., from the venom sample. Other embodiments include obtaining a sample for the snake and obtaining a nucleic acid, or library of nucleic acids, from the sample, e.g., from a venom gland.

The method can further include determining a nucleic acid or protein sequence from material taken form the snake or progeny thereof.

The method can further include making a protein or nucleic acid library from the collected snake or from progeny thereof.

The method can further include obtaining a polypeptide for use, e.g., in animal, human or plant health, inductrial processing or diagnostics.

In another embodiment, the method also includes collecting the snake or sample and sending the snake or sample to a second party, e.g., a party in another country to perform a subsequent step of the method.

In another aspect the invention features a protein, nucleic acid, or library, or nucleic acid or protein sequence information, e.g., as described herein, which is made or produced by a method described herein, e.g., one of the collection methods described herein. In preferred embodiments the invention features a snake protein, e.g., an SVP, e.g., an SVP described herein, or nucleic acid encoding a snake protein, e.g., a nucleic acid encoding an SVP, e.g., an SVP described herein or any of the libraries described herein or the sequence information of any nucleic acid or protein described herein made or produced by a method described herein, e.g., a the collection methods described herein.

In one aspect, the invention features isolated polypeptides comprising the sequence [SEQ ID NO: 28]: MAPQLLLCLILTFLWSLPEAESNVFLKSKX$_1$ANRFLQR TKRX$_2$NSLX$_3$EEX$_4$X$_5$X$_6$GNIERECIEEX$_7$CSKEEAREX$_8$ FX$_9$DX$_{10}$EKTEX$_{11}$FWNVYVDGDQCSSNPCHYX$_{12}$GX$_{13}$ CKDGIGSYTC TCLX$_{14}$X$_{15}$YEGKNCEX$_{16}$X$_{17}$LX$_{18}$X$_{19}$ SCRX$_{20}$X$_{21}$NGNCWHFCKX$_{22}$VQX$_{23}$X$_{24}$X$_{25}$QCSCAE X$_{26}$YX$_{27}$LGX$_{28}$DGHSCVAX$_{29}$GX$_{30}$FSCGRNIKX$_{31}$RNKR EASLPDFVQSX$_{32}$X$_{33}$AX$_{34}$X$_{35}$KKSDNPSPDIRIX$_{36}$NG MDCKLGECPWQAX$_{37}$LX$_{38}$X$_{39}$X$_{40}$X$_{41}$X$_{42}$X$_{43}$X$_{44}$FCGG TILSPIX$_{45}$VLTAAHCIX$_{46}$X$_{47}$X$_{48}$X$_{49}$X$_{50}$X$_{51}$SVX$_{52}$VGEI X$_{53}$X$_{54}$SRX$_{55}$X$_{56}$X$_{57}$X$_{58}$X$_{59}$LLSVDK$_{60}$YVHX$_{61}$KFVX$_{62}$ X$_{63}$X$_{64}$X$_{65}$X$_{66}$X$_{67}$X$_{68}$X$_{69}$X$_{70}$X$_{71}$X$_{72}$X$_{73}$X$_{74}$X$_{75}$X$_{76}$X$_{77}$YD YDIAIX$_{78}$X$_{79}$X$_{80}$KTPIQFSENVVPACLPTADFAX$_{81}$X$_{82}$ VLMKQDX$_{83}$GIX$_{84}$SGFGX$_{85}$X$_{86}$X$_{87}$X$_{88}$X$_{89}$X$_{90}$X$_{91}$X$_{92}$ SX$_{93}$X$_{94}$LKX$_{95}$X$_{96}$X$_{97}$VPYVDR HTCMX$_{98}$SSX$_{99}$X$_{100}$ X$_{101}$ITX$_{102}$X$_{103}$MFCAGYDTLPX$_{104}$DACQGDSGGPHIT AYX$_{105}$DTHFX$_{106}$TGIX$_{107}$SWGEGCAX$_{108}$X$_{109}$GX$_{110}$ YGX$_{111}$ YTKX$_{112}$SX$_{113}$FIX$_{114}$WIKX$_{115}$X$_{116}$MX$_{117}$X$_{118}$ X$_{119}$Z, wherein X$_1$, X$_{10}$, X$_{12-13}$, X$_{15-16}$, X$_{19-23}$, X$_{25}$, X$_{27-30}$, X$_{33-34}$, X$_{37}$, X$_{39}$, X$_{42-47}$, X$_{50}$, X$_{53-56}$, X$_{58-62}$, X$_{64}$, X$_{79}$, X$_{81-83}$, X$_{85-94}$, X$_{96}$, X$_{99-105}$, X$_{108-109}$, X$_{113-115}$ and X$_{117-119}$ are each independently selected from any amino acid residue;

each of X$_2$, X$_6$, X$_{11}$, X$_{14}$, X$_{26}$, X$_{31}$, X$_{48}$ X$_{57}$ and X$_{63}$ is a small amino acid residue;

each of X$_3$, X$_4$, X$_8$, X$_{17}$, X$_{18}$, X$_{35-36}$, X$_{38}$, X$_{51-52}$, X$_{78}$, X$_{80}$, X$_{84}$, X$_{95}$, X$_{98}$, X$_{106-107}$, X$_{111-112}$ and X$_{116}$ is a hydrophobic amino acid residue;

each of X$_5$, X$_7$, and X$_{110}$ is a basic amino acid residue;

each of X$_9$, X$_{40-41}$ and X$_{49}$ is a charged amino acid residue;

X$_{24}$ is an acidic amino acid residue;

X$_{32}$ is a neutral/polar amino acid residue;

X$_{65-67}$, X$_{70-72}$ and X$_{75}$ are each independently absent or selected from any amino acid residue;

X$_{68}$ and X$_{74}$ are each independently absent or selected from acidic amino acid residues;

X$_{69}$, X$_{73}$ and X$_{76}$ are each independently absent or selected from hydrophobic amino acid residues;

X$_{77}$ is absent or is a small amino acid residue; and

Z is absent or is a peptide of from 1-20 amino acids

In some embodiments, $X_1$ is selected from a hydrophobic or acidic amino acid residue, e.g., Val or a modified form thereof, or Glu or a modified form thereof. In some embodiments, $X_2$ is selected from Ala or Ser or a modified form thereof. In some embodiments, $X_3$ is selected from Tyr or Phe or a modified form thereof. In some embodiments, $X_4$ is selected from Phe or Ile or modified form thereof. In some embodiments, $X_5$ is selected from Lys or Arg or modified form thereof. In some embodiments, $X_6$ is selected from Pro or Ser or modified form thereof. In some embodiments, $X_7$ is selected from Arg or Lys or modified form thereof In some embodiments, $X_8$ is selected from Val or Ile or modified form thereof In some embodiments, $X_9$ is selected from Glu or Lys or modified form thereof.

In some embodiments, $X_{10}$ is a neutral/polar or acidic amino acid residue, e.g., $X_{10}$ is selected from Asp or Asn or modified form thereof. In some embodiments, $X_{11}$ is selected from Thr or Ala or modified form thereof. In some embodiments, $X_{12}$ is a small or basic amino acid residue or modified form thereof, e.g., $X_{12}$ is selected from Gly or Arg or modified form thereof. In some embodiments, $X_{13}$ is a hydrophobic or small amino acid residue or modified form thereof, e.g., $X_{13}$ is selected from Ile or Thr or modified form thereof. In some embodiments, $X_{14}$ is selected from Pro or Ser or modified form thereof. In some embodiments, $X_{15}$ is a small or neutral/polar amino acid residue, e.g., $X_{15}$ is selected from Gly or Asn or modified form thereof. In some embodiments, $X_{16}$ is a basic or neutral/polar amino acid residue, e.g., $X_{16}$ is selected from Arg, His or Lys or modified form thereof. In some embodiments, $X_{17}$ is selected from Val or Leu or modified form thereof. In some embodiments, $X_{18}$ is selected from Tyr or Phe or Leu or modified form thereof. In some embodiments, $X_{19}$ is a basic or neural/polar amino acid residue, e.g., $X_{19}$ is selected from Lys or Gln or modified form thereof.

In some embodiments, $X_{20}$ is a hydrophobic or small amino acid residue, e.g., $X_{20}$ is selected from Val, Phe or Ala or modified form thereof. In some embodiments, $X_{21}$ is an acidic or hydrophobic amino acid residue, e.g., $X_{21}$ is selected from Asp or Phe or modified form thereof. In some embodiments, $X_{22}$ is a small or basic amino acid residue, e.g., $X_{22}$ is selected from Pro, Asp or Phe or modified form thereof. In some embodiments, $X_{23}$ is a neutral/polar or small amino acid residue, e.g., $X_{23}$ is selected from Asn or Ser or modified form thereof. In some embodiments, $X_{24}$ is selected from Asp or Glu or modified form thereof. In some embodiments, $X_{25}$ is a hydrophobic or small amino acid residue, e.g., $X_{25}$ is selected from Ile or Thr or modified form thereof. In some embodiments, $X_{26}$ is selected from Gly or Ser or modified form thereof. In some embodiments, $X_{27}$ is a hydrophobic or basic amino acid residue, e.g., $X_{27}$ is selected from Leu or Arg or modified form thereof. In some embodiments, $X_{28}$ is an acidic or hydrophobic amino acid residue, e.g., $X_{28}$ is selected from Glu, Asp or Val or modified form thereof. In some embodiments, $X_{29}$ is a small or acidic amino acid residue, e.g., $X_{29}$ is selected from Gly or Glu or modified form thereof.

In some embodiments, $X_{30}$ is a neutral/polar or acidic amino acid residue, e.g., $X_{30}$ is selected from Asn or Asp or modified form thereof. In some embodiments, $X_{31}$ is selected from Thr or Ala or modified form thereof. In some embodiments, $X_{32}$ is selected from His or Gln or modified form thereof. In some embodiments, $X_{33}$ is a neutral/polar or basic amino acid residue, e.g., $X_{33}$ is selected from Asn or Lys or modified form thereof. In some embodiments, $X_{34}$ is a small or hydrophobic amino acid residue, e.g., $X_{34}$ is selected from Thr or Ile or modified form thereof. In some embodiments, $X_{35}$ is selected from Leu or Val or modified form thereof. In some embodiments, $X_{36}$ is selected from Val or Ile or modified form thereof. In some embodiments, $X_{37}$ is a small or hydrophobic amino acid residue, e.g., $X_{37}$ is selected from Ala or Val or modified form thereof. In some embodiments, $X_{38}$ is selected from Val, Leu or Ile or modified form thereof. In some embodiments, $X_{39}$ is an acidic or neutral/polar amino acid residue, e.g., $X_{39}$ is selected from Asp or Asn or modified form thereof.

In some embodiments, $X_{40}$ is selected from Asp, Glu or Lys or modified form thereof. In some embodiments, $X_{41}$ is selected from Lys or Glu or modified form thereof. In some embodiments, $X_{42}$ is a charged or small amino acid residue, e.g., $X_{42}$ is selected from Lys, Glu or Gly or modified form thereof. In some embodiments, $X_{43}$ is a small or acidic amino acid residue, e.g., $X_{43}$ is selected from Gly, Asp or Glu or modified form thereof. In some embodiments, $X_{44}$ is a small or hydrophobic amino acid residue, e.g., $X_{44}$ is selected from Ala or Val or modified form thereof. In some embodiments, $X_{45}$ is a hydrophobic or neutral/polar amino acid residue, e.g., $X_{45}$ is selected from Tyr or His or modified form thereof. In some embodiments, $X_{46}$ is a small or neutral/polar amino acid residue, e.g., $X_{46}$ is selected from Thr or Asn or modified form thereof. In some embodiments, $X_{47}$ is an acidic or neutral/polar amino acid residue, e.g., $X_{47}$ is selected from Glu or Gln or modified form thereof. In some embodiments, $X_{48}$ is selected from Thr or Ser or modified form thereof. In some embodiments, $X_{49}$ is selected from Glu or Lys or modified form thereof.

In some embodiments, $X_{50}$ is a small, hydrophobic or neutral/polar amino acid residue, e.g., $X_{50}$ is selected from Thr, Met, His or Ser or modified form thereof. In some embodiments, $X_{51}$ is selected from Ile or Val or modified form thereof. In some embodiments, $X_{52}$ is selected from Val or Ile or modified form thereof. In some embodiments, $X_{53}$ is an acidic or neutral/polar amino acid residue, e.g., $X_{53}$ is selected from Asp or Asn or modified form thereof. In some embodiments, $X_{54}$ is a basic or hydrophobic amino acid residue, e.g., $X_{54}$ is selected from Arg or Ile or modified form thereof. In some embodiments, $X_{55}$ is a small or basic amino acid residue, e.g., $X_{55}$ is selected from Ala or Lys or modified form thereof. In some embodiments, $X_{56}$ is an acidic or neutral/polar amino acid residue, e.g., $X_{56}$ is selected from Glu or Asn or modified form thereof. In some embodiments, $X_{57}$ is selected from Pro or Thr or modified form thereof. In some embodiments, $X_{58}$ is a small or basic amino acid residue, e.g., $X_{58}$ is selected from Gly or Arg or modified form thereof. In some embodiments, $X_{59}$ is a small, basic or neutral/polar amino acid residue, e.g., $X_{59}$ is selected from Pro, Arg or His or modified form thereof.

In some embodiments, $X_{60}$ is a hydrophobic or small amino acid residue, e.g., $X_{60}$ is selected from Val, Ile or Ala or modified form thereof. In some embodiments, $X_{61}$ is a basic, neutral/polar or small amino acid residue, e.g., $X_{61}$ is selected from Lys, Gln or Thr or modified form thereof. In some embodiments, $X_{62}$ is a small or hydrophobic amino acid residue e.g., $X_{62}$ is selected from Pro or Leu or modified form thereof. In some embodiments, $X_{63}$ is selected from Pro or Ala or modified form thereof. In some embodiments, $X_{64}$ is a basic, small or neutral/polar amino acid residue e.g., $X_{64}$ is selected from Lys, Thr or Asn or modified form thereof. In some embodiments, $X_{65}$ when present is a basic, small or hydrophobic amino acid residue e.g., $X_{65}$ is selected from Lys, Ser or Tyr or modified form thereof. In some embodiments, $X_{66}$ when present is a small or hydrophobic amino acid residue, e.g., $X_{66}$ is selected from Ser, Gly or Tyr or modified form thereof. In some embodiments, $X_{67}$ when present is a neutral/polar or hydrophobic amino acid residue, e.g., $X_{67}$ is selected from Gln or Tyr or modified form thereof. In some embodiments, $X_{68}$ when present is Glu or modified form thereof. In some embodiments, $X_{69}$ when present is selected from Phe or Val or modified form thereof.

In some embodiments, $X_{70}$ when present is a hydrophobic or neutral/polar amino acid residue, e.g., $X_{70}$ is selected from Tyr or His or modified form thereof. In some embodiments, $X_{71}$ when present is an acidic or neutral/polar amino acid residue, e.g., $X_{71}$ is selected from Glu or Gln or modified form thereof. In some embodiments, $X_{72}$ when present is a basic or neutral/polar amino acid residue, e.g., $X_{72}$ is selected from Lys or Asn or modified form thereof. In some embodiments, $X_{73}$ when present is selected from Phe or Ile or modified form thereof. In some embodiments, $X_{74}$ when present is Asp or modified form thereof. In some embodiments, $X_{75}$ when present is a hydrophobic or basic amino acid residue, e.g., $X_{75}$ is selected from Leu or Arg or modified form thereof. In some embodiments, $X_{76}$ when present is selected from Val or Phe or modified form thereof. In some embodiments, $X_{77}$ when present is selected from Ser or Ala or modified form thereof. In some embodiments, $X_{78}$ is selected from Ile or Leu or modified form thereof. In some embodiments, $X_{79}$ is a neutral/polar or basic amino acid residue, e.g., $X_{79}$ is selected from Gln or Arg or modified form thereof.

In some embodiments, $X_{80}$ is selected from Met or Leu or modified form thereof. In some embodiments, $X_{81}$ is a neutral/polar or basic amino acid residue, e.g., $X_{81}$ is selected from Asn or Lys or modified form thereof. In some embodiments, $X_{82}$ is a neutral/polar or acidic amino acid residue, e.g., $X_{82}$ is selected from Gln or Glu or modified form thereof. In some embodiments, $X_{83}$ is a hydrophobic or small amino acid residue, e.g., $X_{83}$ is selected from Phe or Ser or modified form thereof. In some embodiments, $X_{84}$ is selected from Val or Ile or modified form thereof In some embodiments, $X_{85}$ is a small, basic or neutral/polar amino acid residue, e.g., $X_{85}$ is selected from Gly, Arg or His or modified form thereof. In some embodiments, $X_{86}$ is a hydrophobic or small amino acid residue e.g., $X_{86}$ is selected from Ile or Thr or modified form thereof. In some embodiments, $X_{87}$ is a hydrophobic, basic or neutral/polar amino acid residue, e.g., $X_{87}$ is selected from Phe, Arg or Gln or modified form thereof. In some embodiments, $X_{88}$ is an acidic, small or hydrophobic amino acid residue, e.g., $X_{88}$ is selected from Glu, Ser or Phe or modified form thereof. In some embodiments, wherein $X_{89}$ is a basic, small or hydrophobic amino acid residue, e.g., $X_{89}$ is selected from Arg, Lys, Gly, or Ile or modified form thereof.

In some embodiments, $X_{90}$ is a small or neutral/polar amino acid residue, e.g., $X_{90}$ is selected from Gly, or Gln or modified form thereof. In some embodiments, $X_{91}$ is a small, neutral/polar or hydrophobic amino acid residue, e.g., $X_{91}$ is selected from Pro, Gln or Tyr or modified form thereof. In some embodiments, $X_{92}$ is a neutral/polar or small amino acid residue, e.g., $X_{92}$ is selected from Asn, Gln or Thr or modified form thereof. In some embodiments, $X_{93}$ is a basic or neutral/polar amino acid residue, e.g., $X_{93}$ is selected from Lys or Asn or modified form thereof. In some embodiments, $X_{94}$ is a small or hydrophobic amino acid residue e.g., $X_{94}$ is selected from Thr or Ile or modified form thereof. In some embodiments, $X_{95}$ is selected from Leu, Val or Ile or modified form thereof. In some embodiments, $X_{96}$ is a basic or small amino acid residue, e.g., $X_{96}$ is selected from Lys or Thr or modified form thereof. In some embodiments, $X_{97}$ is selected from Val or Ile or modified form thereof. In some embodiments, $X_{98}$ is selected from Leu or Val or modified form thereof. In some embodiments, $X_{99}$ is a neutral/polar or acidic amino acid residue, e.g., $X_{99}$ is selected from Asn, Glu or Asp or modified form thereof.

In some embodiments, $X_{100}$ is a hydrophobic or small amino acid residue, e.g., $X_{100}$ is selected from Phe or Ser or modified form thereof. In some embodiments, $X_{101}$ is a small or basic amino acid residue, e.g., $X_{101}$ is selected from Pro or Arg or modified form thereof. In some embodiments, $X_{102}$ is a small or neutral/polar amino acid residue, e.g., $X_{102}$ is selected from Pro or Gln or modified form thereof. In some embodiments, $X_{103}$ is a small or neutral/polar amino acid residue, e.g., $X_{103}$ is selected from Thr or Asn or modified form thereof. In some embodiments, $X_{104}$ is a neutral/polar or basic amino acid residue, e.g., $X_{104}$ is selected from Gln or Arg or modified form thereof. In some embodiments, $X_{105}$ is a basic or small amino acid residue, e.g., $X_{105}$ is selected from Arg or Gly or modified form thereof. In some embodiments, $X_{106}$ is selected from Ile or Val or modified form thereof. In some embodiments, $X_{107}$ is selected from Val or Ile or modified form thereof. In some embodiments, $X_{108}$ is a basic or neutral/polar amino acid residue, e.g., $X_{108}$ is selected from Arg, Gln or Lys or modified form thereof. In some embodiments, $X_{109}$ is a basic or small amino acid residue, e.g., $X_{109}$ is selected from Lys or Thr or modified form thereof.

In some embodiments, $X_{110}$ is selected from Arg or Lys or modified form thereof. In some embodiments, $X_{111}$ is selected from Ile or Val or modified form thereof. In some embodiments, $X_{112}$ is selected from Leu or Val or modified form thereof. In some embodiments, $X_{113}$ is a basic or neutral/polar amino acid residue, e.g., $X_{113}$ is selected from Lys or Asn or modified form thereof. In some embodiments, $X_{114}$ is a small or hydrophobic amino acid residue, e.g., $X_{114}$ is selected from Pro or Leu or modified form thereof. In some embodiments, $X_{115}$ is a basic or small amino acid residue, e.g., $X_{115}$ is selected from Arg, Lys or Ala or modified form thereof. In some embodiments, $X_{116}$ is selected from Ile or Val or modified form thereof. In some embodiments, $X_{117}$ a basic or small amino acid residue, e.g., $X_{117}$ is selected from Arg or Ser or modified form thereof. In some embodiments, $X_{118}$ is a neutral/polar, basic or hydrophobic amino acid residue, e.g., $X_{118}$ is selected from Gln, Lys or Leu or modified form thereof. In some embodiments, $X_{119}$ is a basic or neutral/polar amino acid residue, e.g., $X_{119}$ is selected from Lys or His or modified form thereof.

In some embodiments, Z is present and comprises the sequence $X_{118}$PSTESSTGRL [SEQ ID NO: 29], wherein $X_{118}$ is any amino acid residue. In some embodiments, $X_{118}$ is a hydrophobic or neutral polar amino acid residue, e.g., $X_{118}$ is selected from Leu or Gln or modified form thereof.

In some embodiments, $X_{65-77}$ represents a sequence of n amino acids where n is from 0 to 13 amino acid residues, e.g., the sequence is selected from $KX_{119}X_{120}$EFYEKFDLVS [SEQ ID NO: 49], SYYQNIDRFA [SEQ ID NO: 50] or YYYVHQNFDRVA [SEQ ID NO: 51], wherein $X_{119}$ is a small amino acid residue, e.g., $X_{119}$ is selected from Ser or Gly or modified form thereof; and $X_{120}$ is any amino acid residue, e.g., $X_{120}$ is selected from Gln or Tyr or modified form thereof.

Other features and advantages of the invention will be apparent from the following detailed description, and from the claims.

BRIEF DESCRIPTION OF THE TABLES AND FIGURES

Table 1: Characterization of samples during purification of the Brown snake venom protease using Sephacryl S-300.

Table 2: Characterization of samples during purification of Brown snake venom protease using Superdex 200.

Table 3: Characterization of samples during purification of Brown snake venom protease, protocol 1.

Table 4: Characterization of samples during purification of Brown snake venom protease, protocol 2.

Table 5: Characterization of samples during purification of Brown snake venom protease, protocol 3.

Table 6: Characterization of samples during purification of Brown snake venom protease, protocol 4.

Table 7: Hydrolysis of S-2222 by Brown snake venom protease complex with and without accessory components (Brown snake venom protease complex alone, Brown snake venom protease complex with 10 mM $CaCl_2$ and Brown snake venom protease complex with 10 mM $CaCl_2$ and phospholipid).

Table 8: Clotting time of citrated plasma by Brown snake venom protease complex alone, Brown snake venom protease complex with 10 mM $CaCl_2$ and Brown snake venom protease complex with 10 mM $CaCl_2$ and phospholipid.

Table 9: Clotting time of citrated plasma clotting assays±$Ca^{2+}$, with added isolated snake venom protease derived from P. textilis (Brown snake).

Table 10: Clotting of citrated plasma by Brown snake venom protease.

Table 11: Initial rates of hydrolysis of S-2222 by isolated snake venom protease derived from P. textilis, with or without added 10 mM $Ca^{2+}$.

Table 12: Approximate clotting times of clots produced in human citrated plasma using Brown snake venom protease with and without 40 mM $CaCl_2$, and with 40 $CaCl_2$ alone.

Table 13: Determination of the molecular mass of Brown snake venom protease by various methods.

Table 14: Blood loss in a mouse tail-vein bleeding model treated with Brown snake venom protease.

Table 15: Blood loss from Brown snake venom protease (test) and saline (control) treated mice. Data for each individual test mouse can be seen and also average blood loss±standard deviation (SD).

Table 16: Clotting of citrated human plasma by various Australian and exotic snake venoms.

FIG. 1: Elution profile after chromatography of P. textilis venom (10 mL; 233 mg) on a column (2.5×16 cm) of ConA-Sepharose 4B in 0.05 M Tris-HCl, pH 7.4. A. Trace of chromatography pattern. The eluting buffer (0.02 M methyl α-D mannopyranoside in 0.05 M Tris-HCl) was applied to the column at arrow B. Fractions with S-2222 hydrolytic activity were pooled and concentrated (designated by the line at A).

Figure 2:
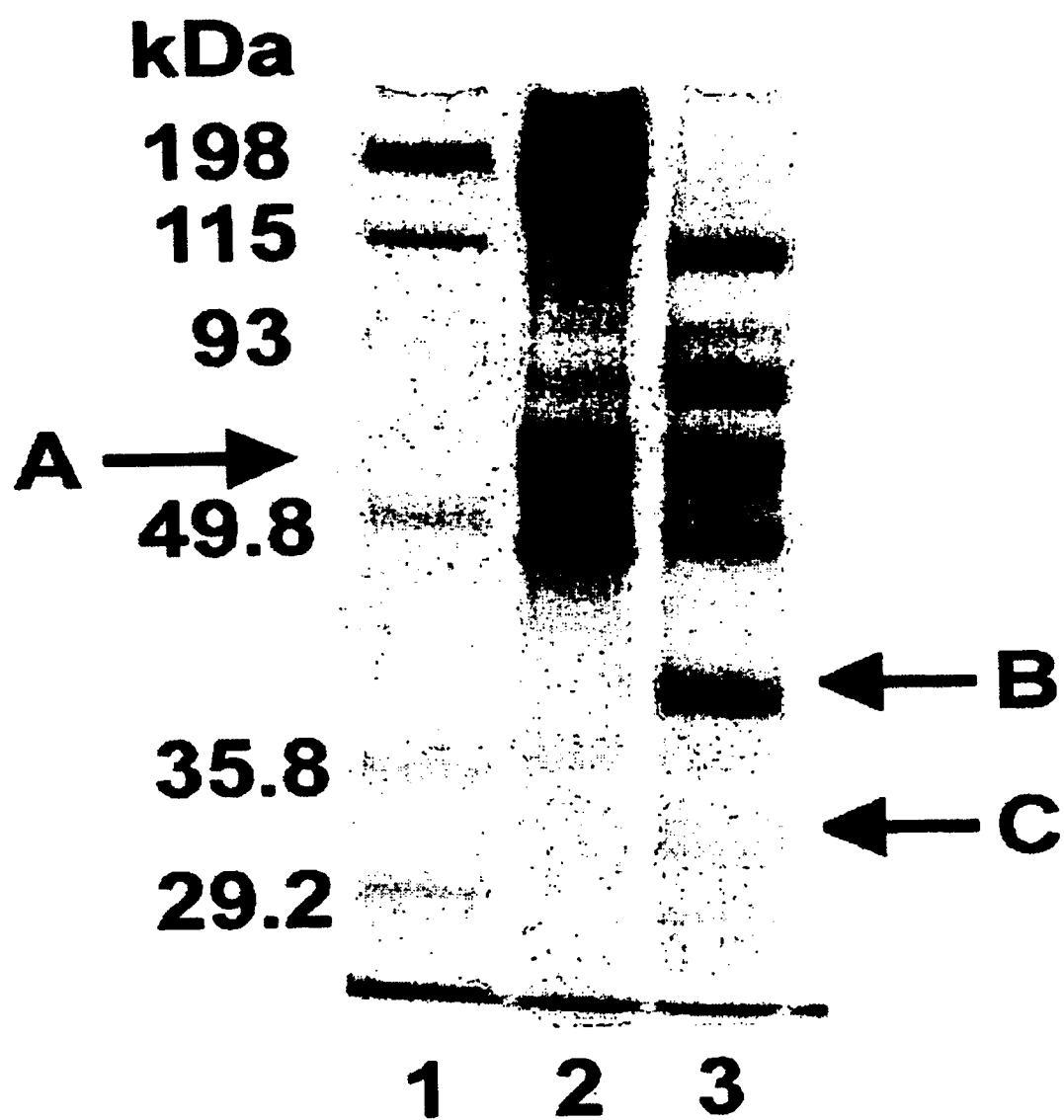

FIG. 2: SDS PAGE of pooled and concentrated peak from ConA-Sepharose 4B chromatography. Lane 1. Molecular weight markers (sizes are shown in kDa). Lane 2. Brown snake venom protease complex without β-mercaptoethanol. Lane 3. Brown snake venom protease complex with β-mercaptoethanol.

Figure 3:
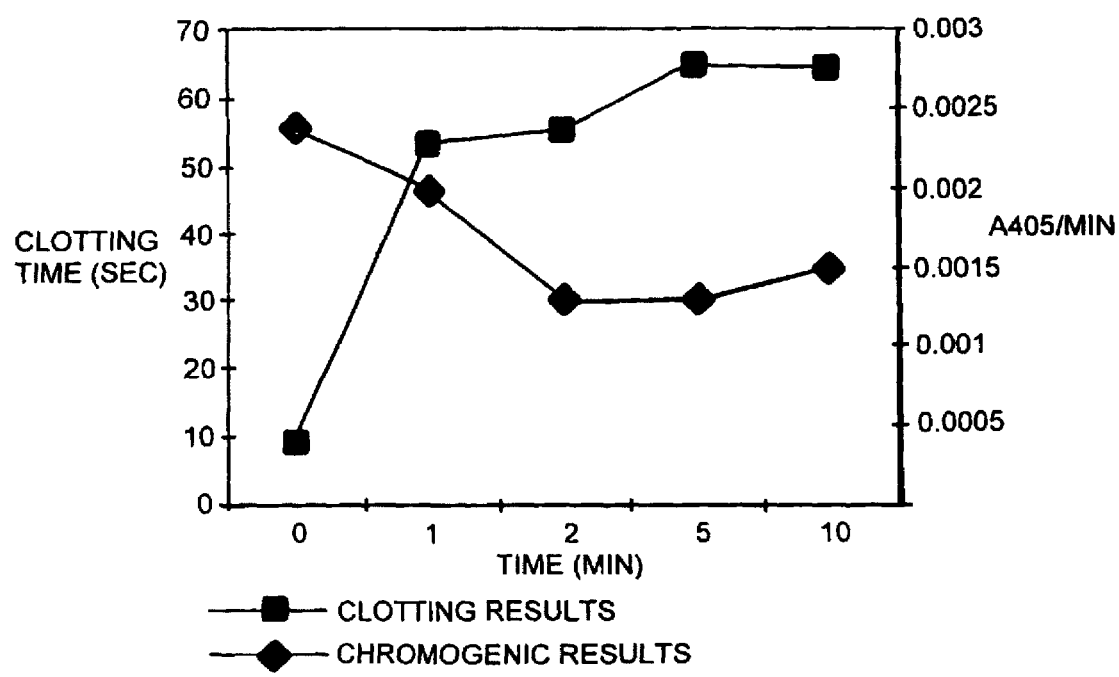

FIG. 3: The effect on citrated plasma clotting time and hydrolysis of S-2222 by snake venom protease complex derived from P. textilis treated with 0.8 M NaSCN.

Figure 4:
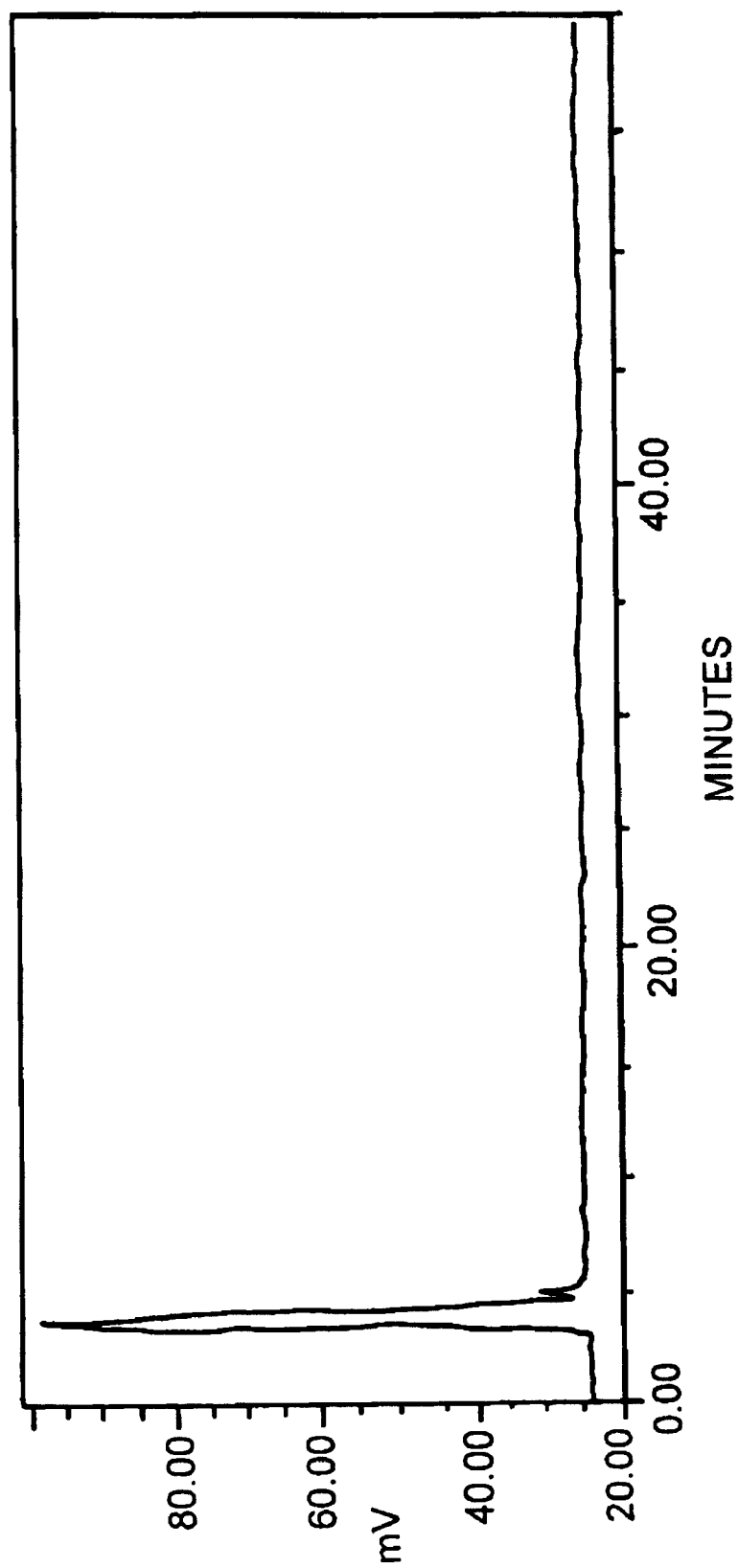

FIG. 4: HPLC data of Brown snake venom serine protease.

Figure 5:
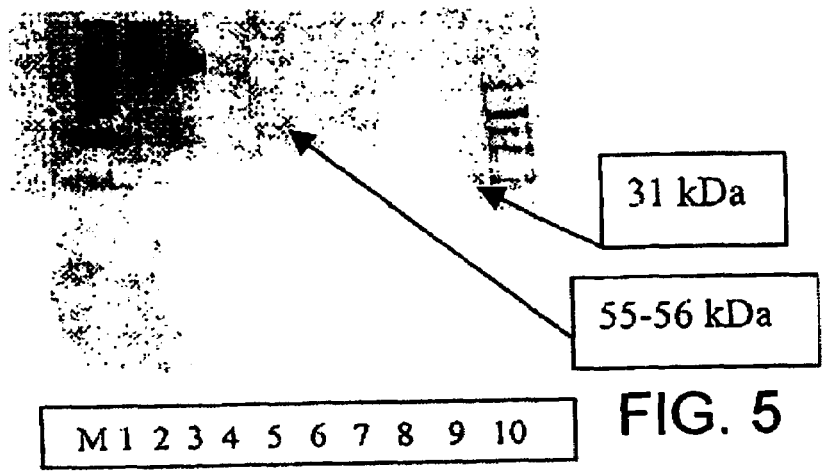

FIG. 5: SDS PAGE±β-Me. Lane M—10 µl BIO-RAD marker, Lane-1 —20 µl P. textilis venom, Lane 2—20 µl intact Pt-PA, Lane 3—20 µl Sephacryl S-300 (1) pooled fractions 30-43, Lane 4—20 µl Sephacryl S-300 (2) pooled fractions 25-29, Lane 5, 6 and 7—10 µl Sephacryl S-300 (3) pooled fractions 25-29, Lane 8 —20 µl Sephacryl S-300 (3) pooled fractions 25-29+β-Me and Lane 9—20 µl intact serum venom protease complex +β-Me, Lane 10—10 µBIO-Rad marker.

Figure 6:
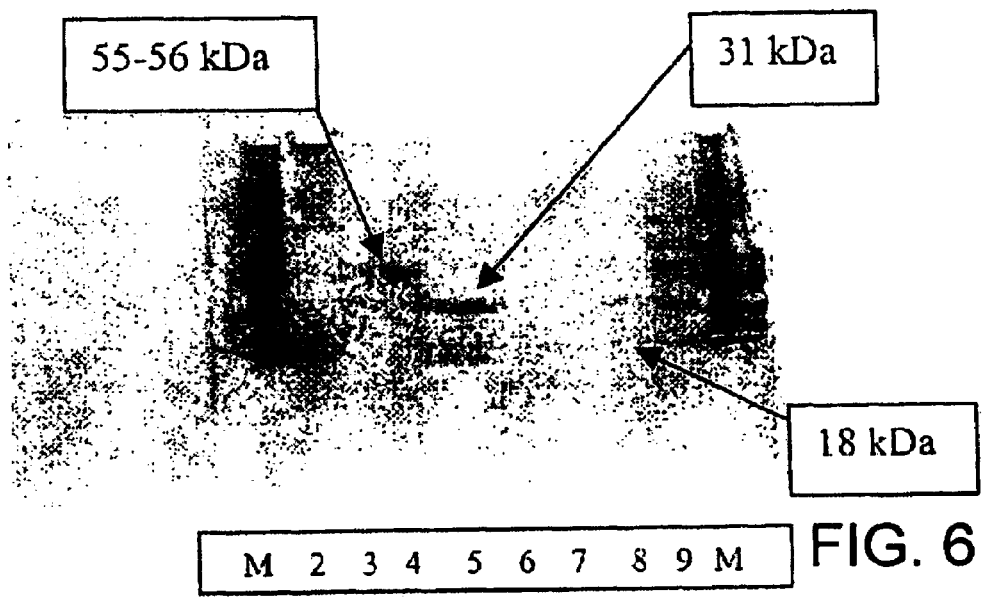

FIG. 6: SDS-PAGE of Brown snake venom serine protease, with or without β-Me. Lane M—BIO-RAD marker, Lane 2—whole P. textilis venom, Lane 3—Sephacryl S-300 (3) pooled fractions 30-43, Lane 4—Sephacryl S-300 (#3), Lane 5—S300 (#3)+β-Me, Lane 6—S300 (#3), Lane 7—Sephacryl S-300 (#3)+β-Me, Lane 8—Sephacryl S-300 (3) pooled fractions 30-43+β-Me, Lane 9—intact Brown snake venom protease complex+β-Me and Lane M—BIO-RAD marker. # represent the pooled and concentrated active peak from Sephacryl S-300 chromatographies of Brown snake venom protease complex as above. All samples consisted of 10 µl aliquots.

Figure 7A:
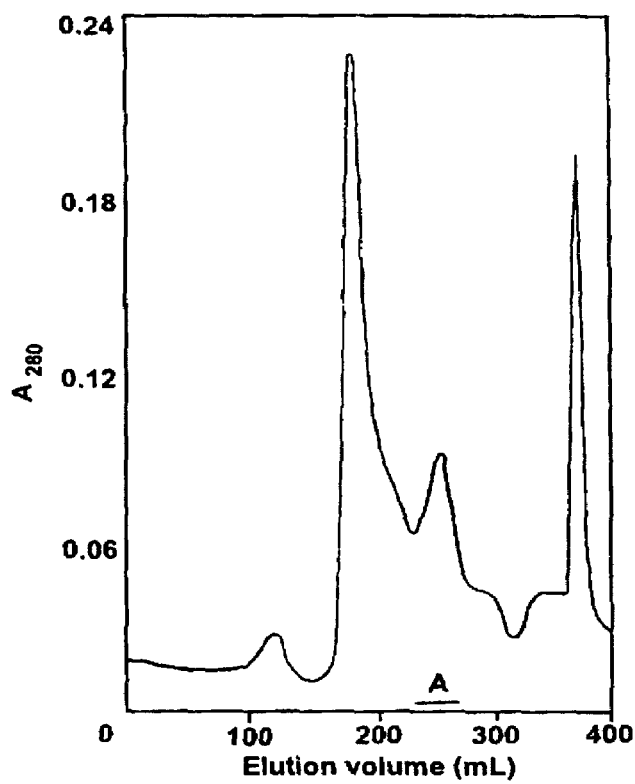

FIG. 7A: Elution profile after chromatography step 1 of Brown snake venom protease complex (18 mL; 50.4 mg) on a column (2.5×90 cm) of Superdex 200 in 0.05 M Tris-HCl, pH 7.4 with 0.8 M NaSCN. Fractions with S-2222 activity were pooled and concentrated, designated by the line at A.

Figure 7B:
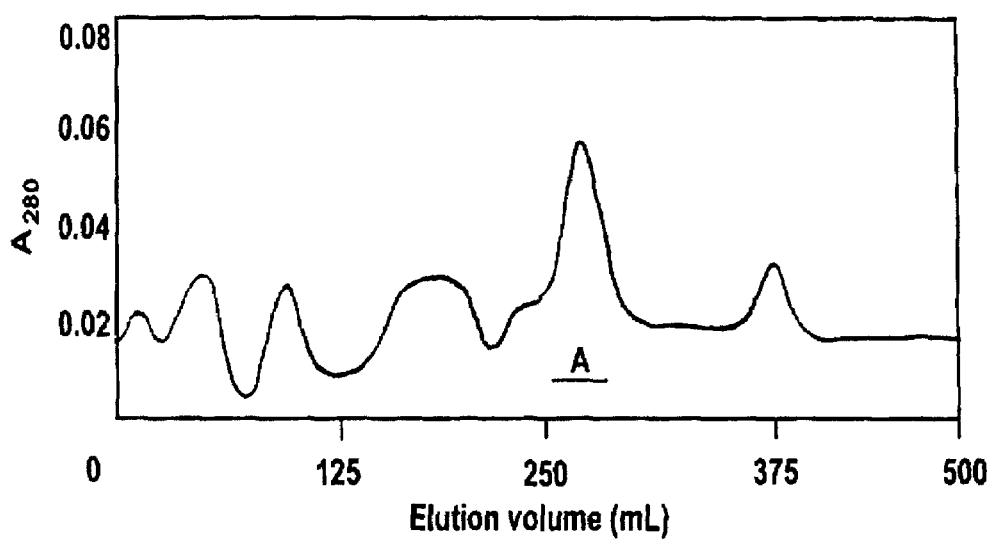

FIG. 7B: Chromatography step 2 as per conditions of FIG. 10A.

Figure 7C:
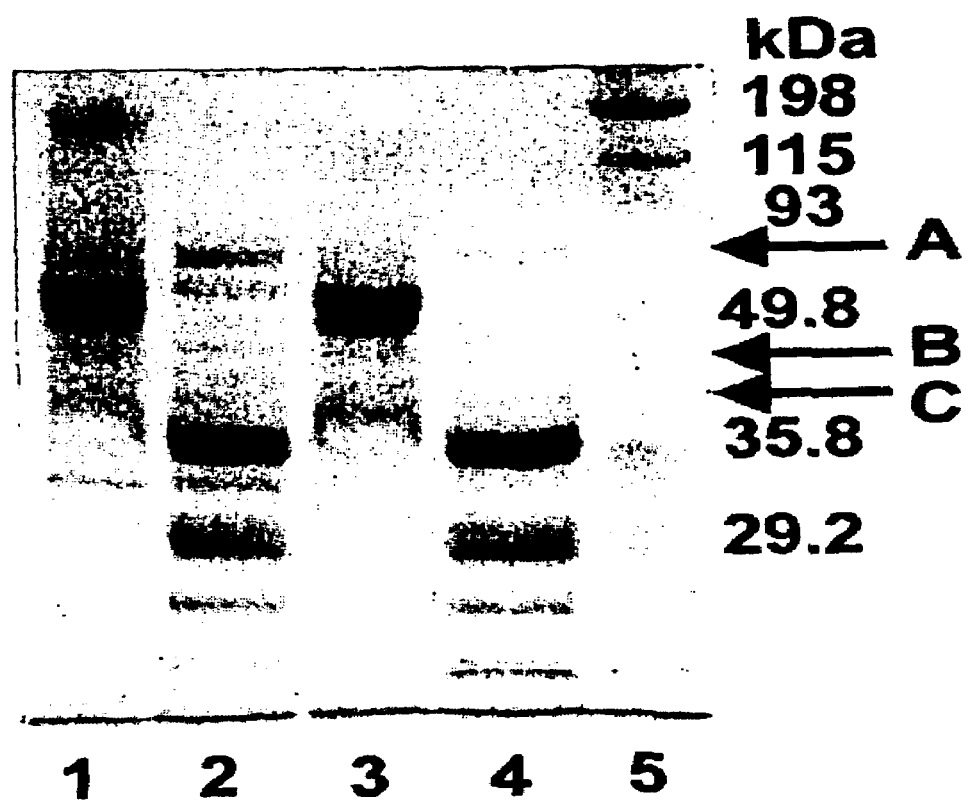

FIG. 7C: SDS PAGE of samples from purification of Brown snake venom protease with Superdex 200. Lanes 1 & 2. Pooled concentrate from chromatography step 1 with (2) and without (1) β-mercaptoethanol. Lanes 3 & 4. Pooled concentrate from chromatography step 2 with (3) and without (4) β-mercaptoethanol. Lane 5. Molecular weight markers (sizes are shown in kDa). Arrows A, B and C indicate impurities in lane 4.

Figure 8A:
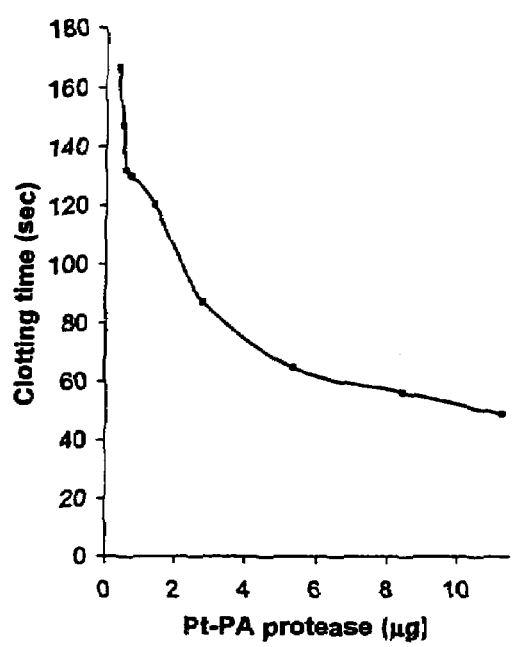

FIG. 8A: Clotting of citrated plasma by Brown snake venom protease (referred to as Pt-PA protease) without accessory components (data points are means of duplicate measurements).

Figure 8B:
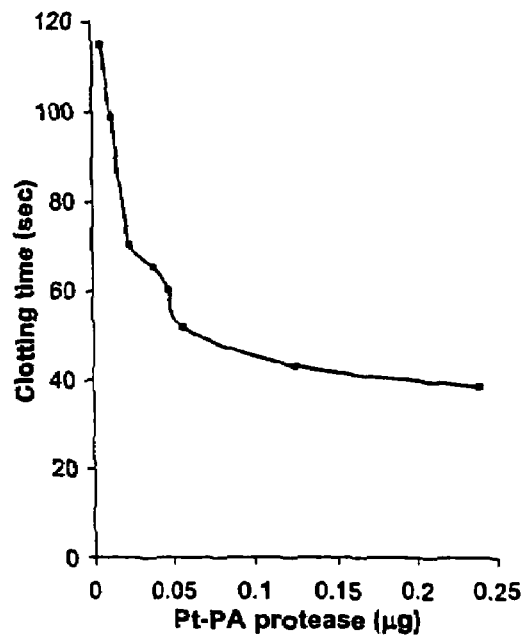

FIG. 8B: Clotting of citrated plasma by Brown snake venom ("Pt-PA") protease with 10 mM $CaCl_2$.

Figure 8C:
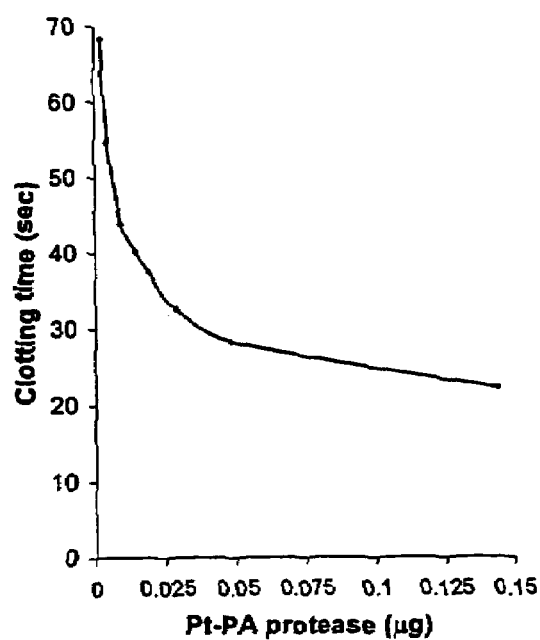

FIG. 8C: Clotting of citrated plasma by Brown snake venom ("Pt-PA") protease with 10 mM $CaCl_2$ and phospholipid.

Figure 9B:
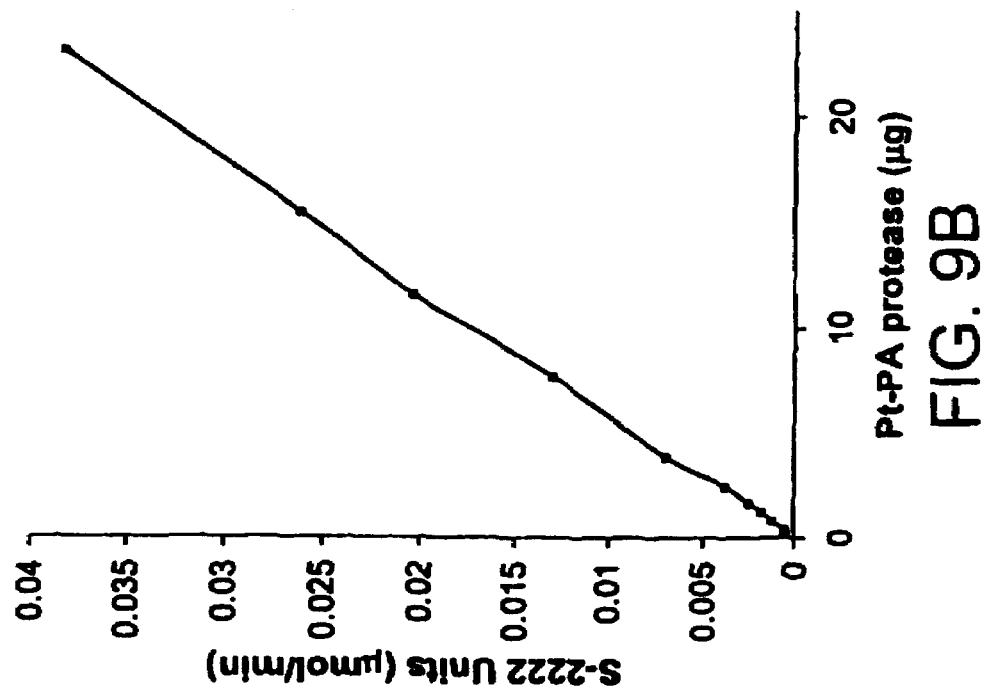
Figure 9A:
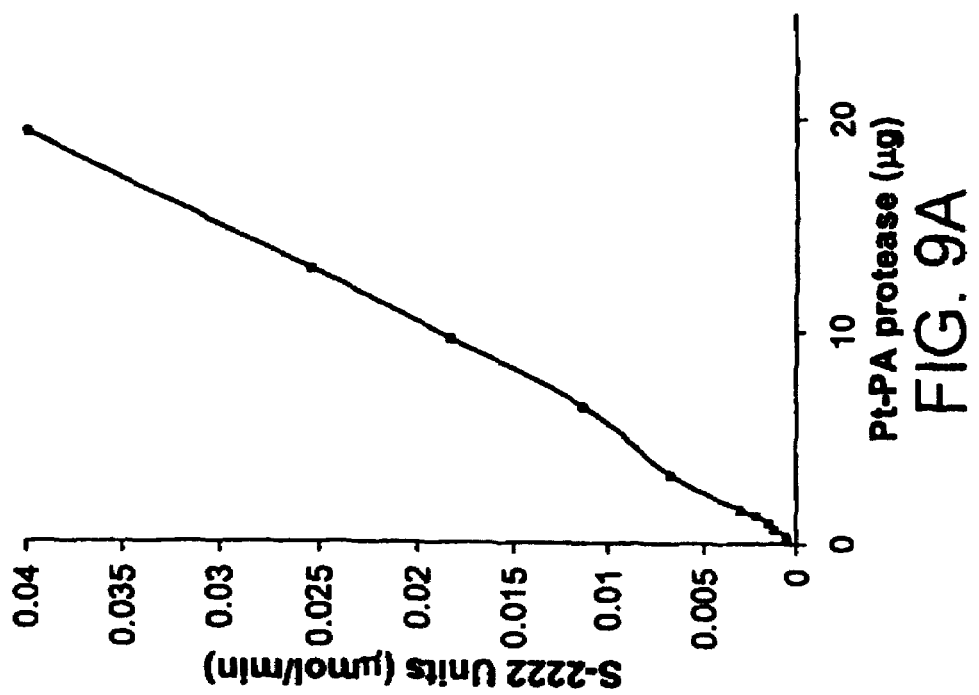

FIG. 9A: Hydrolysis of S-2222 by Brown snake venom protease (referred to as Pt-PA protease) without accessory components (data points are means of duplicate measurements).

FIG. 9B: Hydrolysis of S-2222 by Brown snake venom protease without accessory components (data points are means of duplicate measurements) with 10 mM $CaCl_2$.

Figures 9C, 9D:
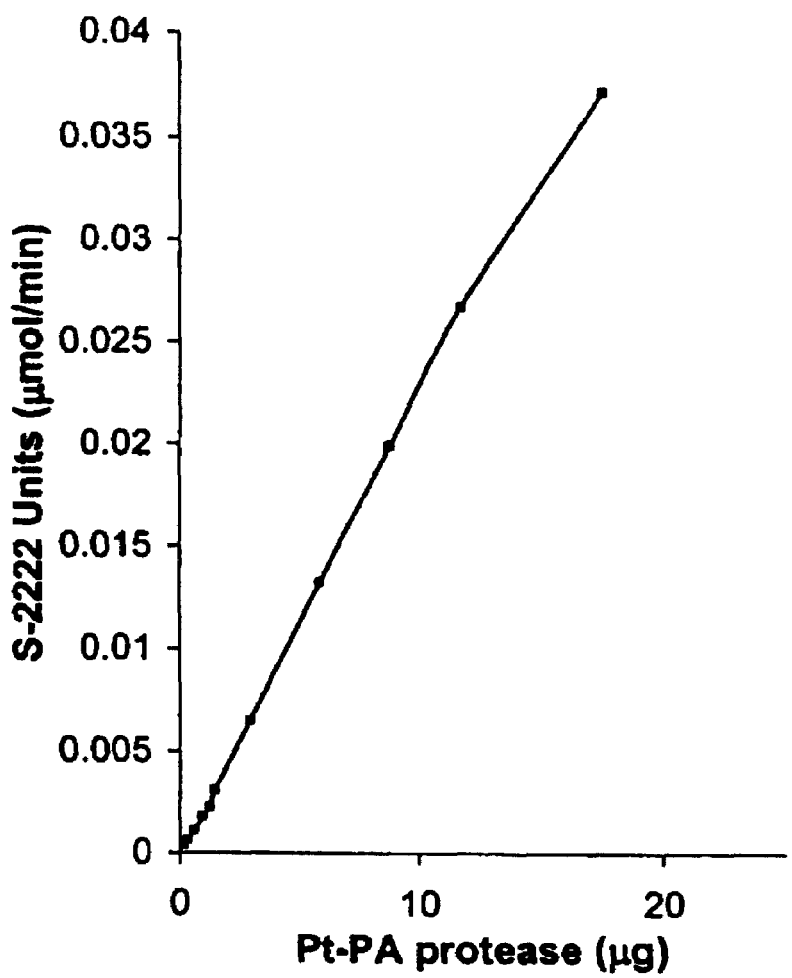

FIG. 9C: Hydrolysis of S-2222 by Brown snake venom protease without accessory components (data points are means of duplicate measurements) with 10 mM $CaCl_2$ and $P_L$.

FIG. 9D: Slope and $R_2$ value of respective plots in FIGS. 9A, 9B and 9C. The $R_2$ value is the correlation coefficient for a straight line.

Figure 10:
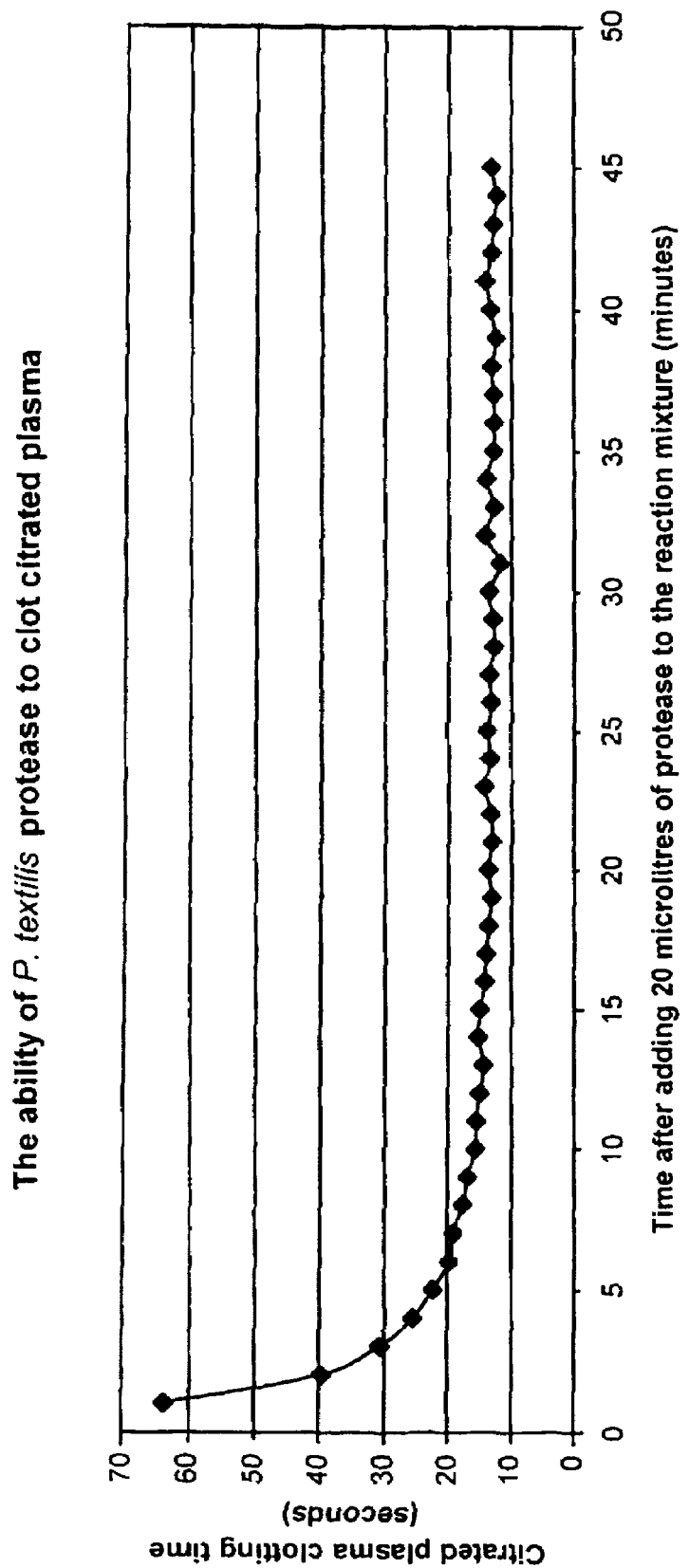

FIG. 10: Prothrombin activation by Brown snake venom protease. Prothrombin (100 µL of a 1.3 mg/mL preparation) was converted to thrombin by Brown snake venom protease (20 µL of a 1.3 mg/mL preparation) in a total volume of 500 µL for time periods indicated on the X-axis. An aliquot of each reaction was then added to a citrated plasma clotting assay and clotting times measured (Y-axis).

Figure 11A:
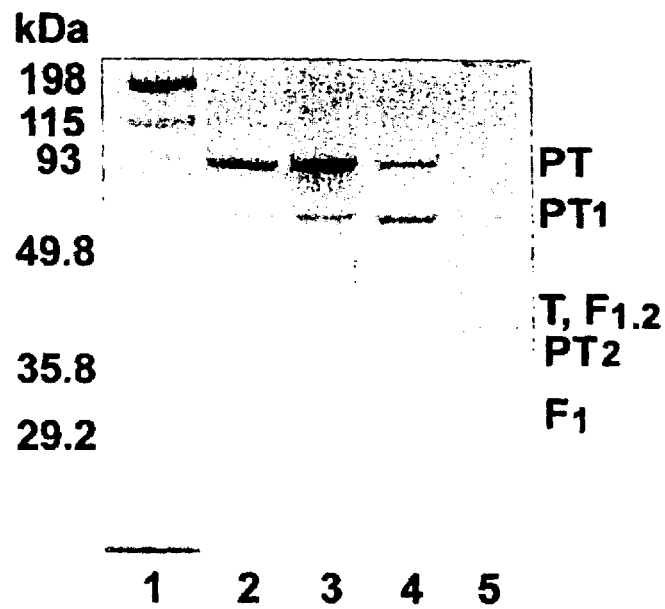

FIG. 11A: SDS PAGE without reduction of prothrombin after incubation with Brown snake venom protease. Brown snake venom protease was added to prothrombin at 0 min (time, t=0); Lane 1, molecular weight markers (sizes shown in kDa); Lane 2, t=0; Lane 3, t=6 min; Lane 4, t=24 h; Lane 5, t=48 h. PT, prothrombin; $PT_1$, prethrombin 1; T, thrombin; $F_{1.2}$, fragment 1.2; $PT_2$, prethrombin 2; $F_1$, fragment 1.

Figure 11B:
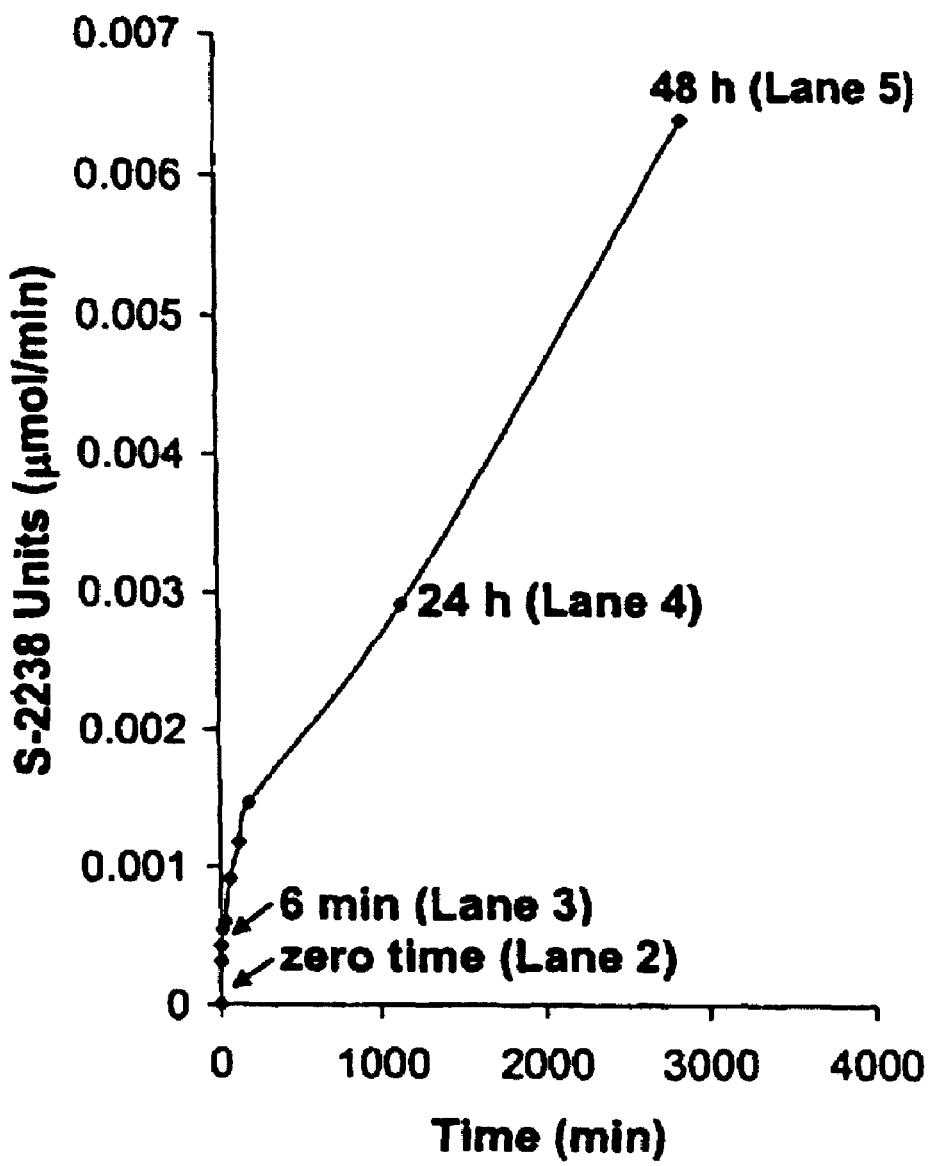

FIG. 11B: Hydrolysis of S-2238 by Brown snake venom protease-generated thrombin.

Figure 12:
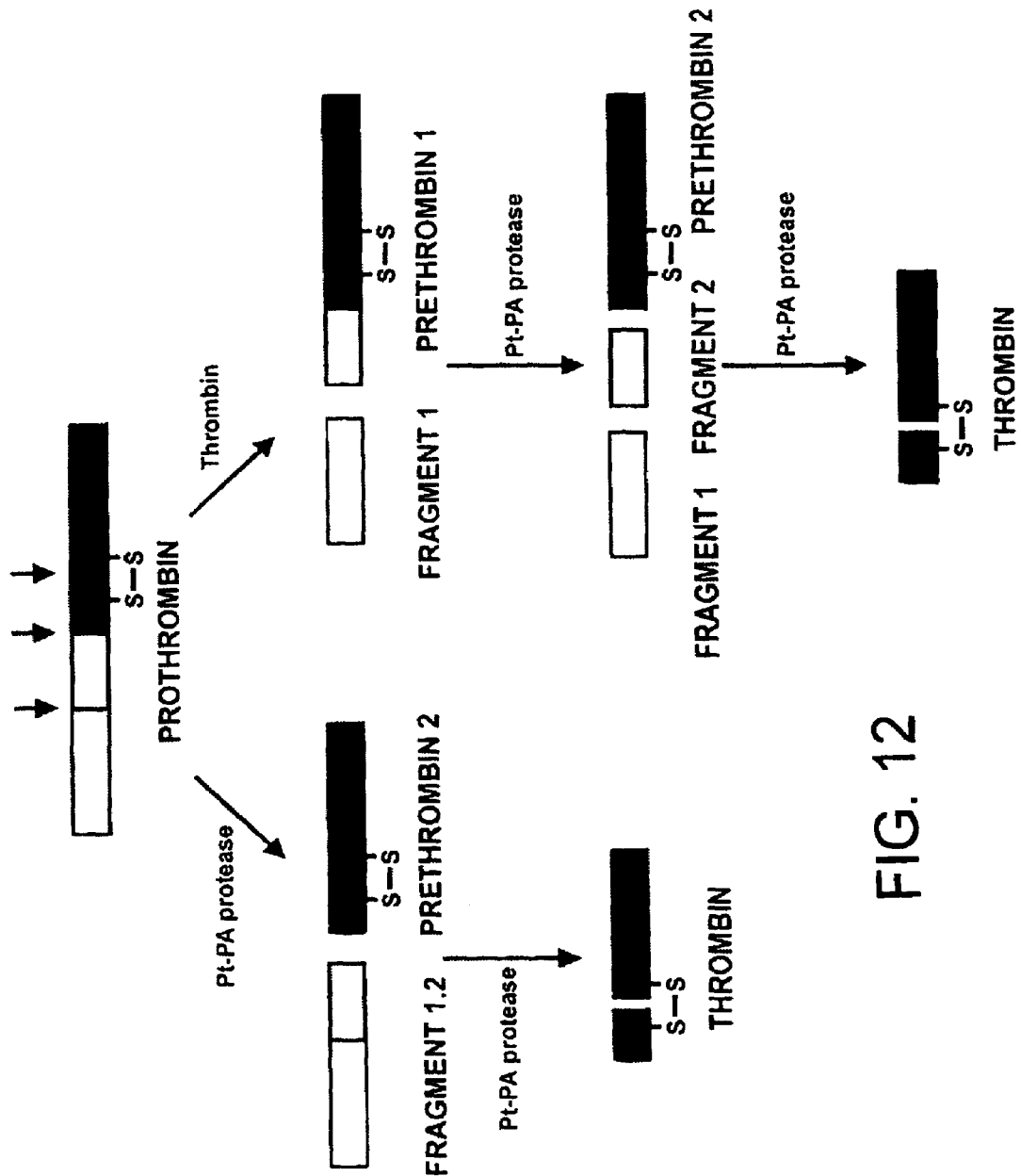

FIG. 12: Proposed model of prothrombin activation by Brown snake venom protease. Arrows indicate bonds that are cleaved by thrombin and Brown snake venom protease.

Figure 13:
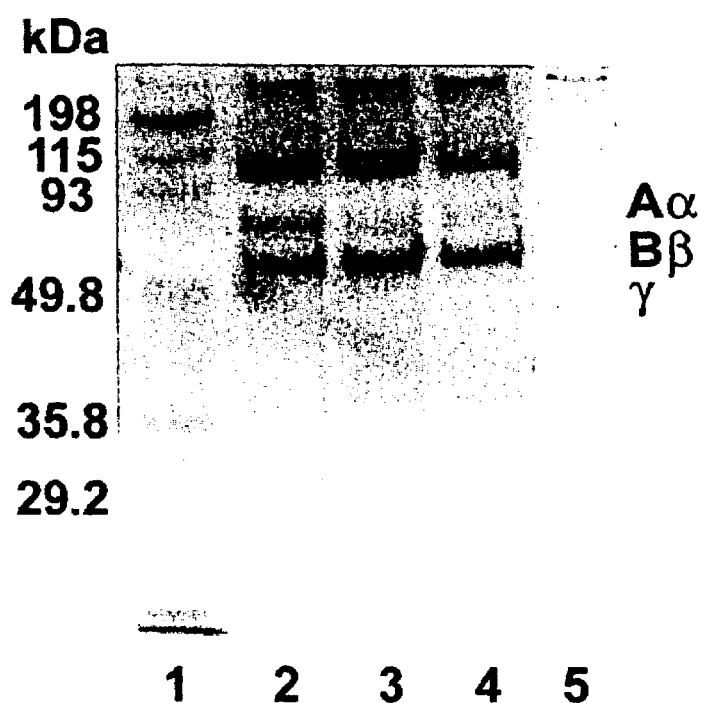

FIG. 13: SDS PAGE of fibrin clots in the presence of β-mercaptoethanol. Lane 1. Molecular weight markers (sizes are shown in kDa). Lane 2. Fibrin clot obtained by the action of 22 μg Brown snake venom protease alone on citrated plasma. Lane 3. Fibrin clot obtained by the action of 22 μg Brown snake venom protease with 40 mM $CaCl_2$ on citrated plasma. Lane 4. Fibrin clot produced with 40 mM $CaCl_2$. Lane 5. Human fibrinogen. The Greek symbols on the right hand side of the gel are indicative of the chains of human fibrinogen including Aα (α monomer and fibrinopeptide A), Bβ (β monomer with fibrinopeptide B) and γ chains.

Figure 14:
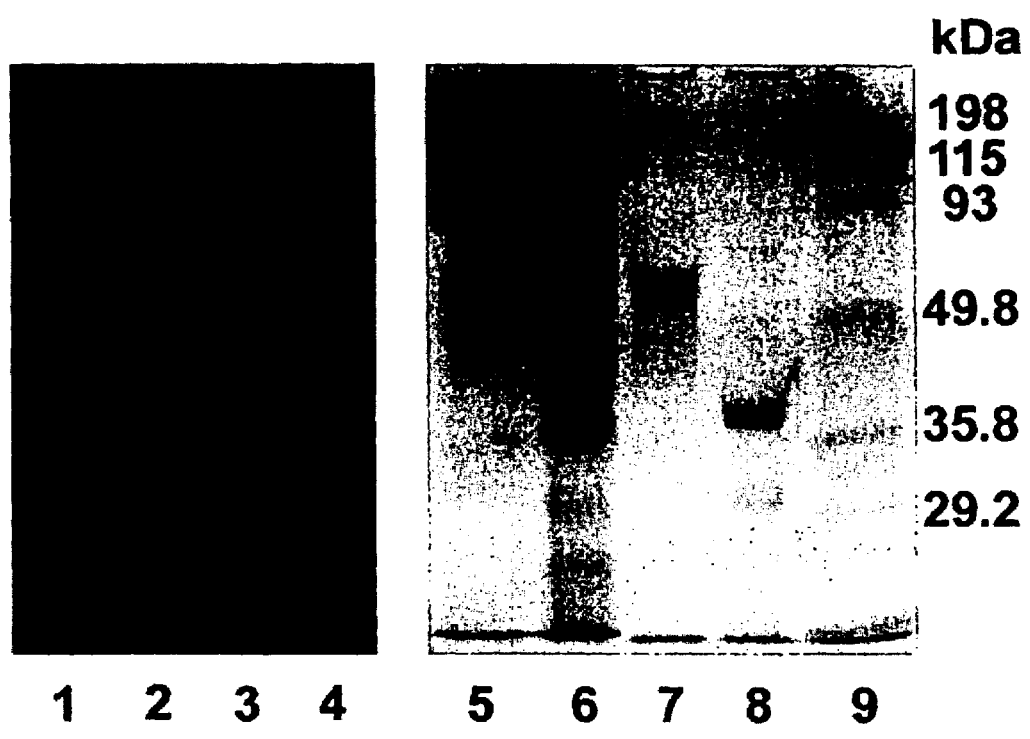

FIG. 14: Mapping of protease active site. SDS PAGE of purified Brown snake venom protease with and without DNS-GGACK treatment. Lanes 1 and 2. Brown snake venom protease complex inhibited with DNS-GGACK with (2) and without β-mercaptoethanol (1). Lanes 3 and 4. Brown snake venom protease inhibited with DNS-GGACK with (4) and without β-mercaptoethanol (3). Lanes 5-8 are a repeat of lanes 1-4 without DNS-GGACK and stained with Coomassie blue. Lane 9. Molecular weight markers (sizes are shown in kDa).

FIG. 15: Amino acid sequence alignment of a protein fragment of Brown snake venom protease [SEQ ID NO:52], trocarin [SEQ ID NO:53] and human factor Xa [SEQ ID NO:53] comprising a putative active site having proposed interacting histidines shown in bold.

FIG. 16: Amino acid sequence alignment of part of the predicted Brown snake venom protease heavy chain [SEQ ID NO:55] and Trocarin [SEQ ID NO:56]. An Expect (E) value is a parameter depicting the number of hits expected by chance when performing a search in the NCBI database. The closer the E value to zero, the more significant the sequence match. The E value decreases exponentially with Score given to a match between two sequences and also depends on the length of sequences compared. An Expect value of 1 means that within the database one match is expected a similar score by chance. Score=39.7, Expect=0.004; Identities=11/11 (100%), Positives=11/11 (100%).

FIG. 17: Amino acid sequence alignment of a part of the predicted Brown snake venom protease heavy chain [SEQ ID NO:55] and human factor Xa [SEQ ID NO:57].

FIG. 18: Amino acid sequence alignment of a part of the predicted Brown snake venom protease light chain [SEQ ID NO:58] and Trocarin [SEQ ID NO:59].

FIG. 19: Sequence alignment of a part of the predicted Brown snake venom protease light chain [SEQ ID NO:60] and mouse factor X [SEQ ID NO:61]. Score=24.8, Expect=116; Identities=9/12 (75%), Positives=9/12 (76%).

FIG. 20A: Nucleotide acid sequence [SEQ ID NO: 1] encoding snake venom protease of *P. textiles* (common brown snake).

FIG. 20B: Amino acid sequence [SEQ ID NO: 2] of snake venom protease of *P. textiles* (common brown snake).

FIG. 21. Amino acid sequence alignment between snake venom proteases isolated from venom glands of the following Australian snakes: *P. textilis* (brown) [SEQ ID NO: 2], *O. scutellatus* (coastal taipan) [SEQ ID NO: 5], *P. porphyriacus* (red-belly black) [SEQ ID NO: 11], *N. scutatus* (mainland tiger) [SEQ ID NO: 14], *T. carinatus* (rough scale) [SEQ ID NO: 17] and Trocarin [SEQ ID NO: 31].

FIG. 22. Amino acid sequence alignment of isolated snake venom proteases with human Xa [SEQ ID NO: 27]. Shown are amino acid sequences of snake venom proteases derived from the following snakes: brown [SEQ ID NO: 2], Coastal Taipan [SEQ ID NO: 5], Red Belly [SEQ ID NO: 11], Rough scale "Roughie" [SEQ ID NO: 14] and Mainland Tiger [SEQ ID NO: 17].

FIG. 23. Amino acid sequence alignment of isolated snake venom proteases with human Xa [SEQ ID NO: 27]. Shown are amino acid sequences of snake venom proteases derived from the following snakes: brown [SEQ ID NO: 2], Coastal Taipan [SEQ ID NO: 5], Red Belly [SEQ ID NO: 11], Rough scale "Roughie" [SEQ ID NO: 14], Mainland Tiger [SEQ ID NO: 17], and human factor X [SEQ ID NO: 27].

Figure 24C:
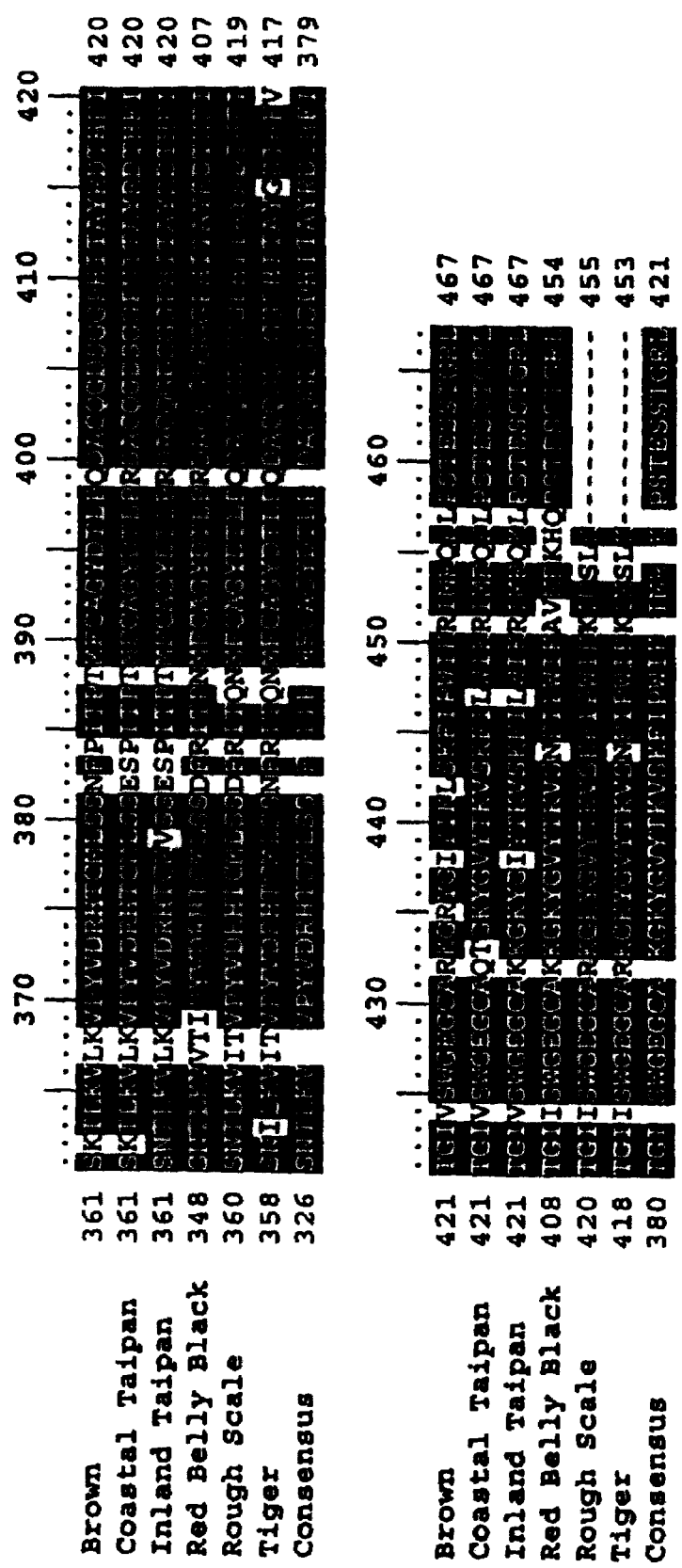

FIG. 24 Amino acid sequence alignment between snake venom proteases isolated from venom glands of the Australian snakes *P. textiles* (brown) [SEQ ID NO:2], *O. scutellatus* (coastal taipan) [SEQ ID NO: 5], *O. microepidotus* (inland taipan) [SEQ ID NO:8], *P. porphyriacus* (red-belly black) [SEQ ID NO:11], *N. scutatus* (mainland tiger) [SEQ ID NO:14], *T. carinatus* (rough scale) [SEQ ID NO:17] and consensus sequence [SEQ ID NO: 30].

FIG. 25. Nucleotide sequence alignment of nucleic acids encoding snake venom proteases derived from following Australian snakes: *P. textilis* (brown) [SEQ ID NO: 1], *O. scutellatus* (costal taipan) [SEQ ID NO: 4], *P. porphyriacus* (red-belly black) [SEQ ID NO: 10], *N. scutatus* (mainland tiger) [SEQ ID NO: 13], *T. carinatus* (rough scale) [SEQ ID NO: 16] and human Factor Xa [SEQ ID NO: 26].

FIG. 26. Nucleotide sequence alignment of nucleic acids encoding snake venom proteases derived from following Australian snakes: *P. textilis* (brown) [SEQ ID NO: 1], *O. scutellatus* (costal taipan) [SEQ ID NO: 4], *O. microlepidotus* (inland taipan) [SEO ID NO:7], *P. porphyriacus* (red-belly black) [SEQ ID NO: 10], *N. scutatus* (mainland tiger) [SEQ ID NO: 13], and *T. carinatus* (rough scale) [SEQ ID NO: 16].

Figure 27:
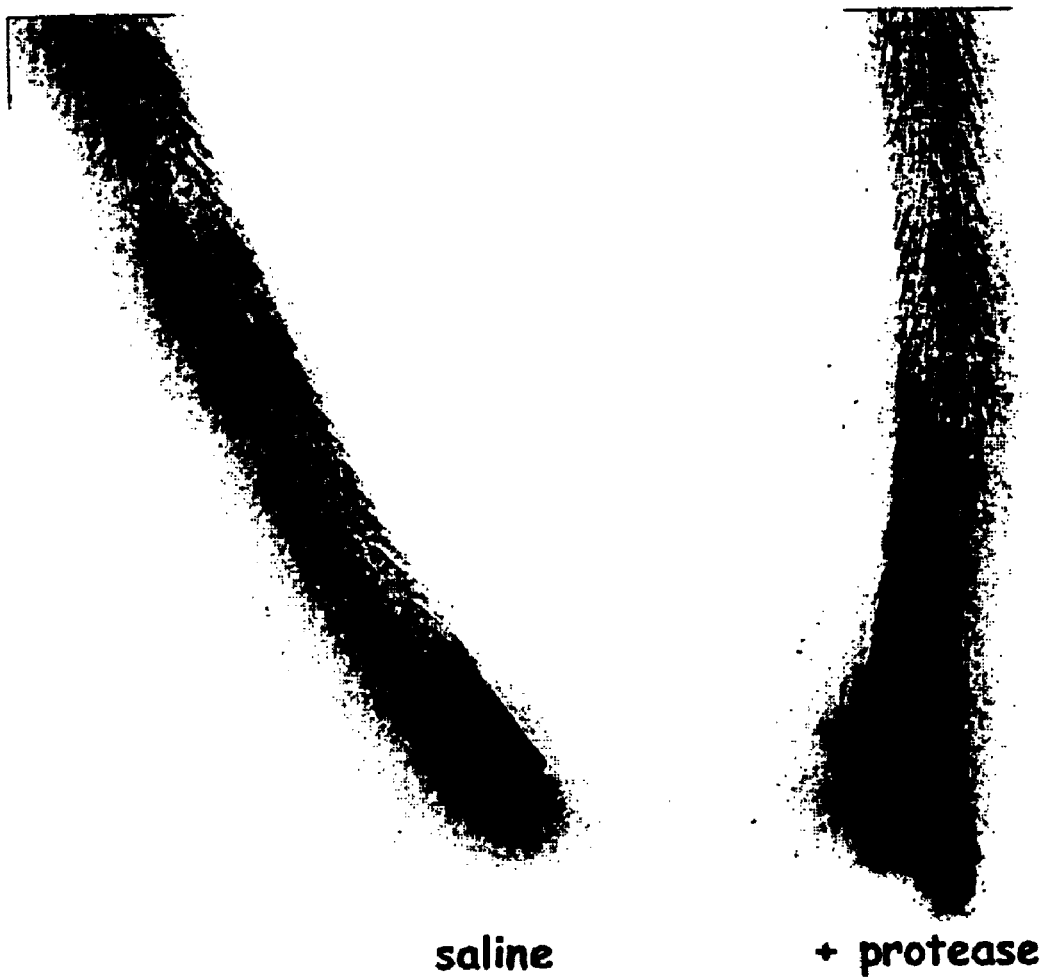

FIG. 27: Shows mouse tails with and without treatment with Brown snake venom protease (note the large clot formed with protease treatment).

Figure 28:
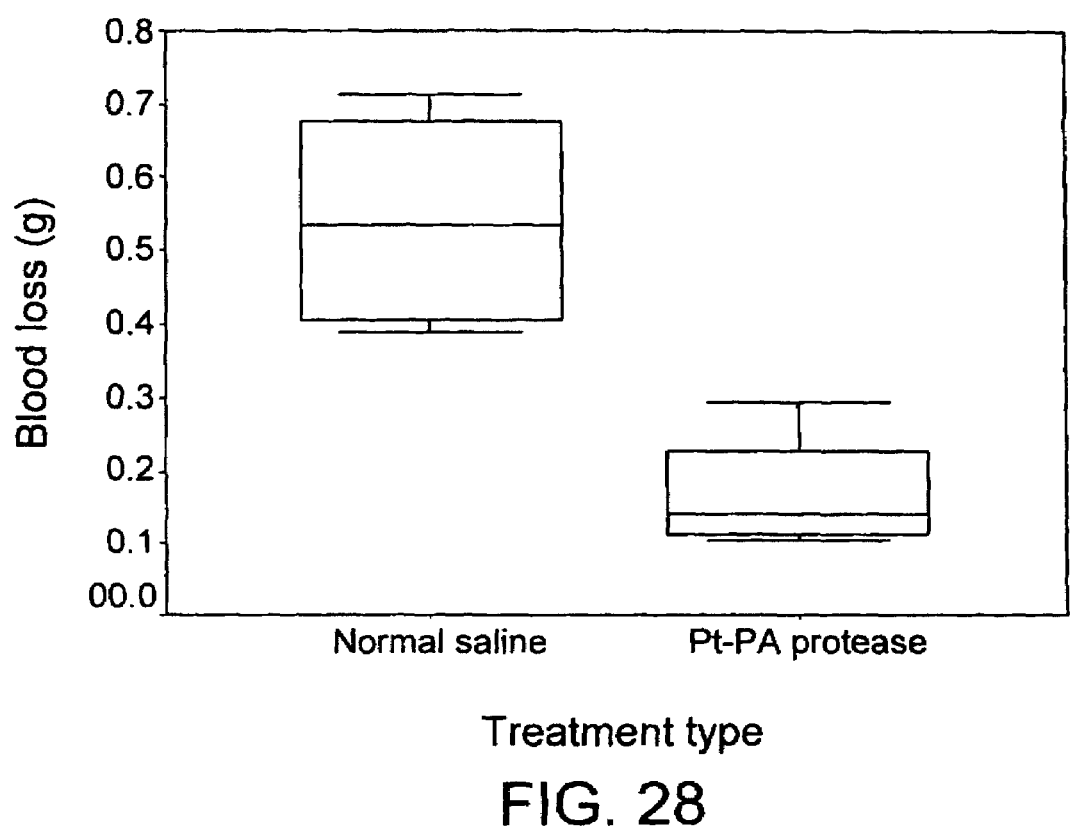

FIG. 28: Box plot of mouse bleeding results. Each box represents a range that comprises 50% of values. The whiskers are lines that extend from the box to the highest and lowest values. The line across the box indicates the median.

DETAILED DESCRIPTION OF THE INVENTION

Snake venoms are an abundant source of proteins and other constituents that affect the haemostatic mechanism of mammals via inhibition and/or activation of factors within the pathways of platelet aggregation, fibrinolysis and the coagulation cascade. Of particular note are the snake venom proteases unique to Australian elapid snake species. Normally, proteolytic cleavage of prothrombin to its active from thrombin, is catalysed by the prothrombinase complex in mammalian systems. The functional protease within prothrombinase is factor Xa. However, for optimal activity, the Xa enzyme requires factor Va as a cofactor in the presence of calcium ions and phospholipids.

The invention is based, in part, from the isolation of snake venom proteases from venom of Australian snakes. Examples of Australian snakes include coastal taipan (*Oxyuranus scutellatus*), inland taipan (*Oxyuranus microlepidotus*), mainland tiger (*Notechis scutatus*), rough scaled (*Tropidechis carinatus*), red-belly black snake (*Pseudechis porphyriacus*), other snakes from the family *Elapidae*, and any brown snake of the genus *Pseudonaja*, wherein any brown snake includes the common brown snake (*Pseudonaja textilis*). The snake venom proteases of the invention mimic the effect of factor Xa in vivo, cleaving prothrombin to thrombin, however they do so in the absence of cofactors, such as factor Va, phospholipid and calcium ions. Thus, the snake venom proteases described herein act as either complete or partially complete prothrombin activators. The term "complete prothrombin activator" as used herein refers to a snake venom protease which process prothrombin to thrombin in the absence of calcium, phospholipids and factor Va. Examples of snake venom proteases which act as complete prothrombin activators include snake venom proteases from the brown snake and the taipan snakes. The term "partially complete prothrombin activators" as used herein refers to snake venom proteases which process prothrombin to thrombin in the absence of calcium and phospholipids, but do require the presence of factor Va.

In one particular embodiment, the invention provides isolated snake venom proteases isolated from the venom of the common Australian brown snake (*P. textilis*), taipan (*Oxyuranus scutellatus*)-coastal or inland, mainland tiger (*Notechis scutatus*), rough scaled (*Tropidechis carinatus*) and red-belly black snake (*Pseudechis porphyriacus*).

A snake venom protease of the invention may be isolated from a prothrombinase complex referred to herein as a "Snake venom protease complex" The snake venom protease complex may comprise several proteins and/or cofactors. Snake venom proteases of the invention include, for example, those proteins shown in FIG. 23 and proteolytically digested sub-fragments thereof. FIG. 23 depicts the amino acid sequence of a snake venom protease from brown snake (SEQ ID NO:2); the amino acid sequence of a snake venom protease from coastal taipan snake (SEQ ID NO:5); the amino acid sequence of a snake venom protease from inland taipan snake (SEQ ID NO:8); the amino acid sequence of a snake venom protease from red belly black snake (SEQ ID NO:11); the amino acid sequence of a snake venom protease from tiger snake (SEQ ID NO: 14); and the amino acid sequence of a snake venom protease from rough scale snake (SEQ ID NO:17).

The snake venom proteases of the invention contain a significant number of structural characteristics in common with each other. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. Members of a family can also have common functional characteristics.

As used herein, a "snake venom protease activity", "biological activity of a snake venom protease" or "functional activity of a snake venom protease", refers to an activity exerted by a snake venom protease protein, polypeptide or nucleic acid molecule. For example, a snake venom protease activity can be one or more of: the ability to process prothrombin to thrombin (e.g., the ability to cleave prothrombin between the arginine residue 274 and the threonine residue 275 of prothrombin and between the arginine residue 323 and the isoleucine residue 324 of prothrombin, e.g., the ability to cleave prothrombin between the arginine residue 274 and the threonine residue 275 of prothrombin and between the arginine residue 323 and the isoleucine residue 324 of prothrombin but not to cleave prothrombin between the arginine residue 155 and the serine residue 156 and/or between the arginine residue 286 and the threonine residue 287); the ability to produce clotting in citrate-treated plasma; the ability to process prothrombin and/or produce clotting in the absence of calcium and phospholipid. The isolated snake venom proteases of the invention are characterized by having a prothrombinase activity largely independent of calcium as shown, for example, in Tables 8-12.

The invention features snake venom polypeptides and biologically active fragments thereof, that are complete or partially complete prothrombin activators. A complete or partial activator shows significantly greater activity in the absence of cofactors than does an incomplete activator, e.g., human factor X or trocarin. Embodiments of complete or partially complete activators of the invention have a level of activity that is about 0.4% of the activity of the complete prothrombin activator in combination with $Ca^{2+}$ and phospholipids. The activity of the complete or partially complete prothrombin activator alone in preferred embodiments is at least 1.5, 2, 4, 10, 15, 20, 50, 100, 1000, or 4000 fold (two to four orders of magnitude) higher than that of an incomplete activator, e.g., human factor Xa, or trocarin, alone. This comparison is made between a snake venom protease and an incomplete activator measured under the same or similar conditions, e.g., in the absence of Ca and phospholipids. In preferred embodiments, the % of activity (i.e., the activity of the complete or partially complete activator in the absence of Ca and phospholipid as a % of that seen with the same activator in the presence of Ca and phospholipids) of a complete or partially complete is at least 1.5, 2, 4, 10, 15, 20, 50, 100, 1000, or 4000 fold greater than the same % shown by an incomplete activator, e.g., human factor X or trocarin. Preferred complete or partially complete activators will clot citrated plasma at concentration of about $10^{-10}$ to $10^{-06}$ M, e.g., at $10^{-8}$ or $10^{-7}$ M, giving clotting times of about 50 to 15 seconds, demonstrating $Ca^{2+}$ and phospholipid independence. Accordingly, the prothrombin activator shows kinetic properties of cofactor independence (calcium ions and/or phospholipid) in the concentration range of about $10^{-10}$ to $10^{-06}$ M concentration range being a suitable working range to reduce blood loss.

The snake venom protease proteins, fragments thereof, and derivatives and other variants of the sequence in SEQ ID NO:2, 5, 8, 11, 14 and 17, are collectively referred to as "polypeptides or proteins of the invention" or "snake venom protease polypeptides or proteins". Nucleic acid molecules encoding such polypeptides or proteins are collectively referred to as "nucleic acids of the invention" or "snake venom protease-encoding nucleic acids." Snake venom protease molecules refer to snake venom protease nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA. FIG. 26 depicts a nucleic acid sequence encoding a snake venom protease from brown snake (SEQ ID NO:1, coding region SEQ ID NO:3); a nucleic acid sequence encoding a snake venom protease from coastal taipan snake (SEQ ID NO:4, coding region SEQ ID NO:6); a nucleic acid sequence encoding a snake venom protease from inland taipan snake (SEQ ID NO:7), coding region SEQ ID NO:9); a nucleic acid sequence encoding a snake venom protease from red belly black snake (SEQ ID NO:10, coding region SEQ ID NO:12); a nucleic acid sequence encoding a snake venom protease from tiger snake (SEQ ID NO: 13, coding region SEQ ID NO:15); and a nucleic acid sequence encoding a snake venom protease from rough scale snake (SEQ ID NO:16, coding region SEQ ID NO:18).

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID Nos: 1, 3, 4, 6, 7, 9, 10, 12, 13, 15, 16 or 18 corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a snake venom protease protein. The gene can optionally further include non-coding sequences, e.g., regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of a snake venom protease protein is at least 10% pure. In a preferred embodiment, the preparation of snake venom protease protein has less than about 30%, 20%, 10% and more preferably 5% (by dry weight), of non-snake venom protease protein (also referred to herein as a "contaminating protein"), or of chemical precursors or non-snake venom protease chemicals. When the snake venom protease protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of a snake venom protease without abolishing or substantially altering a snake venom protease activity. Preferably the alteration does not substantially alter the snake venom protease activity, e.g., the activity is at least 20%, 40%, 60%, 70% or 80% of wild-type. An "essential" amino acid residue is a residue that, when altered from the wild-type sequence of a snake venom protease, results in abolishing a snake venom protease activity such that less than 20% of the wild-type activity is present. For example, conserved amino acid residues in between the snake venom proteases, e.g., the snake venom proteases shown in FIG. 24 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a snake venom protease protein is preferably replaced with another amino acid residue from the same side chain family. Alternatively, in another embodiment, mutations can be introduced randomly along all or part of a snake venom protease coding sequence, such as by saturation mutagenesis, and the resultant mutants can be screened for snake venom protease biological activity to identify mutants that retain activity. Following mutagenesis of SEQ ID Nos: 1, 3, 4, 6, 7, 9, 10, 12, 13, 15, 16 or 18, the encoded protein can be expressed recombinantly and the activity of the protein can be determined.

Amino acid residues can be generally sub-classified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium.

Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington DC; and by Gonnet et al., 1992, Science 256(5062): 144301445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, sub-classification according to the foregoing scheme is presented in the following Table.

| Amino acid sub-classification | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, and is not, therefore, included in a group.

The "modified" amino acids that may be included in the SVPs are gene-encoded amino acids which have been processed after translation of the gene, e.g., by the addition of methyl groups or derivatization through covalent linkage to other substituents or oxidation or reduction or other covalent modification. The classification into which the resulting modified amino acid falls will be determined by the characteristics of the modified form. For example, if lysine were modified by acylating the ε-amino group, the modified form would not be classed as basic but as polar/large.

Certain commonly encountered amino acids, which are not encoded by the genetic code, include, for example, β-alanine (β-Ala), or other omega-amino acids, such as 3-aminopropionic, 2,3-diaminopropionic (2,3-diaP), 4-aminobutyric and so forth, α-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); .beta.-2-thienylalanine (Thi); methionine sulfoxide (MSO); and homoarginine (Har). These also fall conveniently into particular categories.

Based on the above definitions, Sar, beta-Ala and Aib are small; t-BuA, t-BuG, N-MeIle, Nle, Mvl, Cha, Phg, Nal, Thi and Tic are hydrophobic; 2,3-diaP, Orn and Har are basic; Cit, Acetyl Lys and MSO are neutral/polar/large. The various omega-amino acids are classified according to size as small (β-Ala and 3-aminopropionic) or as large and hydrophobic (all others).

Other amino acid substitutions for those encoded in the gene can also be included in SLEs within the scope of the invention and can be classified within this general scheme according to their structure.

In all of the SVPs of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogues which include these alternative-linking moieties: Spatola, A. F., Vega Data (March 1983), Vol. 1, Issue 3, "Peptide Backbone Modifications" (general review); Spatola, A. F., in "Chemistry and Biochemistry of Amino Acids Peptides and Proteins", B. Weinstein, eds., Marcel Dekker, New York, p. 267 (1983) (general review); Morley, J. S., *Trends Pharm Sci* (1980) pp. 463-468 (general review); Hudson, D., et al., *Int J Pept Prot Res* (1979) 14:177-185 (—CH$_2$NH—, —CH$_2$CH$_2$—); Spatola, A. F., et al., *Life Sci* (1986) 38:1243-1249 (—CH$_2$—S); Hann, M. M., *J Chem Soc Perkin Trans I* (1982) 307-314 (—CH—CH—, cis and trans); Almiquist, R. G., et al., *J Med Chem* (1980) 23:1392-1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401-4404 (—C(OH)CH$_2$—); and Hruby, V. J., *Life Sci* (1982) 31: 189-199 (—CH$_2$—S—).

As used herein, a "biologically active portion" of a snake venom protease protein includes a fragment of a snake venom protease protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a snake venom protease molecule and a non-snake venom protease molecule, e.g. prothrombin, or between a first snake venom protease molecule, e.g., a light chain of a snake venom protease and a second snake venom protease molecule (e.g., a dimerization interaction). Biologically active portions of a snake venom protease protein include peptides comprising amino acid sequences sufficiently homologous to or derived from the amino acid sequence of the snake venom protease protein, e.g., the amino acid sequences shown in SEQ ID NOs:2, 5, 8, 11, 14 or 17, which include less amino acids than the full length snake venom protease proteins, and exhibit at least one activity of a snake venom protease protein. Typically, biologically active portions comprise a domain or motif with at least one activity of the snake venom protease protein, e.g., the ability to process prothrombin to thrombin, e.g., in the absence of calcium and/or phospholipid. A biologically active portion of a snake venom protease protein can be a polypeptide which is, for example, 10, 25, 50, 100, 200 or more amino acids in length. Preferably, said fragment is a "biologically-active portion" having no less than 1%, preferably no less than 10%, more preferably no less than 25% and even more preferably no less than 50% of the prothrombin processing activity of the snake venom proteases described herein The invention contemplates a "fragment" of a snake venom protease of the invention. The term "fragment" includes within its scope heavy and light chain fragments of a snake venom protease. In one embodiment, the fragment is a peptide comprising an amino acid sequence as shown below (residue numbers as shown in FIG. 27):

```
KREASLPDFVQS                            (residues 181-192) [SEQ ID NO: 19]

LKKSDNPSPDIR                            (residues 198-209) [SEQ ID NO: 20]

SVXVGEIXXSR                             (residues 260-270) [SEQ ID NO: 21]

MAPQLLLCLILTFLWSLPEAESNVFLKSK           (residues 1-29)    [SEQ ID NO: 22]

ANRFLQRTKR                              (residues 31-40)   [SEQ ID NO: 23]

KREASLPDFVQSXXAXXLKKSDNPSPDIIR          (residues 181-209) [SEQ ID NO: 24]

MAPQLLLCLILTFLWSLPEAESNVFLKSKXANRFLQRTKR (residues 1-40)    [SEQ ID NO: 25]
```

X may be any amino acid.

It will be appreciated that peptide sub-fragments of the above peptide fragments are also contemplated, for example peptides as set forth by SEQ ID NOS: 19 and 20 are respective sub-fragments of the peptide set forth by SEQ ID NO: 24. Other fragments and sub-fragments may be selected by a person skilled in the art. In still another embodiment, a "fragment" is a small peptide, for example of at least 6, preferably at least 10 and more preferably at least 20 amino acids in length. Larger fragments comprising more than one peptide are also contemplated, and may be obtained through the application of standard recombinant nucleic acid techniques or synthesized using conventional liquid or solid phase synthesis techniques. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatography (HPLC) techniques.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWS-gapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, wordlength=12 to obtain nucleotide sequences homologous to 53010 nucleic acid molecules of the invention. BLAST protein searches can be performed with the BLASTX program, score=50, wordlength=3 to obtain amino acid sequences homologous to 53010 protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., BLASTX and BLASTN) can be used.

Particularly preferred snake venom protease polypeptides of the present invention have an amino acid sequence substantially identical to the amino acid sequence of SEQ ID NOs:2, 5, 8, 11, 14 or 17. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NOs:2, 5, 8, 11, 14 or 17 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NOs:1, 3, 4, 6, 7, 9, 10, 12, 13, 15, 16, or 18 are termed substantially identical.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Variants may fall within the scope of the term "homologs" of the snake venom protease proteins of the invention.

As generally used herein, a "homolog" shares a definable nucleotide or amino acid sequence relationship with a nucleic acid or amino acid sequence of the invention as the case may be. The snake venom protease proteins of the invention derived from different snakes are homologs of each other.

Included within the scope of homologs are "orthologs", which are snake venom protease proteins and their encoding nucleic acids, isolated from organisms other than *Pseudonaja textilis, Oxyuranus scutellatus, Notechis scutatus, Tropidechis carinatus* and *Pseudechis porphyriacus*. Also, a snake venom protease protein from one of the above species is an ortholog of any of the other mentioned species. For example, a snake venom protease protein from *P. textilis* is an ortholog of a snake venom protease protein from *O. scutellatus*.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Isolated prothrombin activating proteins of the invention (inclusive of fragments, variants, derivatives and homologs) may be prepared by any suitable procedure known to those of skill in the art.

Various aspects of the invention are described in further detail below.

Isolated Nucleic Acid Molecules

In one aspect, the invention provides, an isolated or purified, nucleic acid molecule that encodes a snake venom protease polypeptide described herein, e.g., a full-length snake venom protease protein or a fragment thereof, e.g., a biologically active portion of snake venom protease protein. Also included is a nucleic acid fragment suitable for use as a hybridization probe, which can be used, e.g., to identify a nucleic acid molecule encoding a polypeptide of the invention, snake venom protease mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NOs:1, 3, 4, 6, 7, 9, 10, 12, 13, 15, 16, or 18, or a portion of any of these nucleotide sequences. In one embodiment, the nucleic acid molecule includes sequences encoding the snake venom protease protein (i.e., "the coding region" of SEQ ID NO:1, 4, 7, 10, 13 or 16, as shown in SEQ ID NO:3, 6, 9, 12, 15 or 18, respectively), as well as 5' untranslated sequences. Alternatively, the nucleic acid molecule can include only the coding region of SEQ ID NO:1, 4, 7, 10, 13 or 16 (e.g., SEQ ID NO:3, 6, 9, 12, 15 or 18, respectively) and, e.g., no flanking sequences which normally accompany the subject sequence. In another embodiment, the nucleic acid molecule encodes a sequence corresponding to a fragment of the protein. For example, the nucleic acid molecule encodes one or more of a snake venom protease propeptide, light chain, activation peptide and heavy chain. In another embodiment, the nucleic acid molecule can encode on or more of the domains or regions described herein.

In another embodiment, an isolated nucleic acid molecule of the invention includes a nucleic acid molecule which is a complement, e.g., a full complement, of the nucleotide sequence shown in SEQ ID NO:1, 3, 4, 6, 7, 9, 10, 12, 13, 15, 16, or 18, or a portion of any of these nucleotide sequences, e.g., any portion encoding a domain or region described herein. In other embodiments, the nucleic acid molecule of the invention is sufficiently complementary to the nucleotide sequence shown in SEQ ID NO:1, 3, 4, 6, 7, 9, 10, 12, 13, 15, 16, or 18, such that it can hybridize (e.g., under a stringency condition described herein) to the nucleotide sequence shown in SEQ ID NO:1, 3, 4,6 ,7, 9, 10, 12, 13, 15, 16, or 18, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, 3, 4, 6, 7, 9, 10, 12, 13, 15, 16, or 18, or a portion, preferably of the same length, of any of these nucleotide sequences.

Snake Venom Protease Nucleic Acid Fragments

A nucleic acid molecule of the invention can include only a portion of the nucleic acid sequence of SEQ ID NO:1, 3, 4, 6, 7, 9, 10, 12, 13, 15, 16, or 18. For example, such a nucleic acid molecule can include a fragment which can be used as a probe or primer or a fragment encoding a portion of a snake venom protease protein, e.g., an immunogenic or biologically active portion of a snake venom protease protein, e.g., an immunogenic or biologically active portion of a snake venom protease protein described herein. A fragment can comprise those nucleotides of SEQ ID NO:1, 3, 4, 6, 7, 9, 10, 12, 13, 15, 16, or 18, which encodes, e.g., a propeptide, a light chain, an activator peptide, a heavy chain, a GLA domain, an EGF-1 domain, an EGF-2 domain, or any other domain or region described herein, of snake venom protease. The nucleotide sequence determined from the cloning of the snake venom protease gene allows for the generation of probes and primers designed for use in identifying and/or cloning other snake venom protease family members, or fragments thereof, as well as snake venom protease homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50, 100, 150, 200, 250, 300, 350, 400, 450, 500, or 550 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a snake venom protease nucleic acid fragment can include a sequence corresponding to a GLA domain, an EGF domain or a factor Va-like domain.

Snake venom protease probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, 3, 4, 6, 7, 9, 10, 12, 13, 15, 16 and/or 18, or of a naturally occurring allelic variant or mutant of SEQ ID NO:1, 3, 4, 6, 7, 9, 10, 12, 13, 15, 16, or 18. Preferably, an oligonucleotide is less than about 200, 150, 120, or 100 nucleotides in length. In a preferred embodiment, the snake venom protease probes or primers hybrize to a region of a snake venom protease encoding nucleic acid but do not hybridize to a region of human factor Xa and/or trocarin.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:2, 5, 8, 11, 14 or 17. The reverse primer can anneal to the ultimate codon, e.g., the codon immediately before the stop codon, e.g., the codon encoding amino acid residue 581 of SEQ ID NO:2, 5, 8, 11, 14, or 17. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes: a propeptide, a light chain, an activator peptide, a heavy chain, or portions thereof (or domains within such regions).

In another embodiment a set of primers is provided, e.g., primers suitable for use in a PCR, which can be used to amplify a selected region of a snake venom protease sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a propeptide, a light chain, an activator peptide, a heavy chain (or domains and sites within those regions).

A nucleic acid fragment can encode an epitope bearing region of a polypeptide described herein.

A nucleic acid fragment encoding a "biologically active portion of a snake venom protease polypeptide" can be prepared by isolating a portion of the nucleotide sequence of SEQ ID NO:1, 3, 4, 6, 7, 9, 10, 12, 13, 15, 16, or 18, which encodes a polypeptide having a snake venom protease biological activity (e.g., the biological activities of the snake venom protease proteins are described herein), expressing the encoded portion of the snake venom protease protein (e.g., by recombinant expression in vitro) and assessing the activity of the encoded portion of the snake venom protease protein. A nucleic acid fragment encoding a biologically active portion of a snake venom protease polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400 or more nucleotides in length and hybridizes under a stringency condition described herein to a nucleic acid molecule of SEQ ID NO:1, 3, 4, 6, 7, 9, 10, 12, 13, 15, 16, or 18.

Snake Venom Protease Nucleic Acid Variants

The invention further encompasses nucleic acid molecules that differ from the nucleotide sequence shown in SEQ ID NO:1, 3, 4, 6, 7, 9, 10, 12, 13, 15, 16 or 18. Such differences can be due to degeneracy of the genetic code (and result in a nucleic acid which encodes the same snake venom protease proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2, 5, 8, 11, 14 or 17. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the invention can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (sarne locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). In one embodiment, nucleic acid homologs are orthologous nucleic acids isolated from snakes other than *Pseudonaja textilis, Oxyuranus scutellatus, Notechis scutatus, Tropidechis carinatus* and *Pseudechis porphyriacus*.

In a preferred embodiment, the nucleic acid differs from that of SEQ ID NO: 1, 3, 4, 6, 7, 9, 10, 12, 13, 15, 16 or 18, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is typically at least about 70-75%, more typically at least about 80-85%, and most typically at least about 90-95% or more identical to the nucleotide sequence shown in SEQ ID NO:2, 5, 8, 11, 14 or 17 or a fragment of this sequence and preferably has a snake venom protease activity. Such nucleic acid molecules can readily be identified as being able to hybridize under a stringency condition described herein, to the nucleotide sequence shown in SEQ ID NO 2, 5, 8, 11, 14, 17, or a fragments thereof. Nucleic acid molecules corresponding to orthologs, homologs, and allelic variants of the snake venom protease cDNAs of the invention can further be isolated by mapping to the same chromosome or locus as the snake venom protease gene.

Preferred variants include those that have a snake venom protease activity, e.g., an ability to induce clotting in the absence of one or more of calcium, phospholipid and factor Va.

Allelic variants of snake venom protease include both functional and non-functional proteins. Functional allelic variants are naturally occurring amino acid sequence variants of the snake venom protease protein within a population that maintain the ability to process prothrombin. Functional allelic variants will typically contain only conservative substitution of one or more amino acids of SEQ ID NO:2, 5, 8, 11, 14 or 17, or substitution, deletion or insertion of non-critical residues in non-critical regions of the protein. Non-functional allelic variants are naturally-occurring amino acid sequence variants of the snake venom protease protein within a population that do not have the ability to process prothrombin. Non-functional allelic variants will typically contain a non-conservative substitution, a deletion, or insertion, or premature truncation of the amino acid sequence of SEQ ID NO:2, 5, 8, 11, 14, 17, or a substitution, insertion, or deletion in critical residues or critical regions of the protein.

Moreover, nucleic acid molecules encoding other snake venom protease family members and, thus, which have a nucleotide sequence which differs from the snake venom protease sequences of SEQ ID NO:1, 3, 4, 6, 7, 9, 10, 12, 13, 15, 16 or 18 are intended to be within the scope of the invention.

Isolated nucleic acid homologs of the invention may also be prepared by methods utilizing nucleic acid sequence amplification techniques.

In one embodiment, the method includes the steps of:
(i) obtaining a nucleic acid extract from a host cell or animal;

(ii) creating one or more primers which, optionally, are degenerate wherein each said primer corresponds to a portion of an isolated nucleic acid of the invention; and (iii) using said primers to amplify, via a nucleic acid amplification technique, one or more amplification products from said nucleic acid extract.

Suitably, said one or more primers are designed to be capable of annealing to one or the other strands of a double-stranded nucleic acid of the invention under annealing and primer extension conditions typically used for amplification. In the case of degenerate primers, sequence differences between the primer and the isolated nucleic acid sequence are intentionally introduced to account for possible sequence variation, such as due to degeneracy in homologous coding sequences.

Suitable nucleic acid amplification techniques are well known to the skilled addressee, and include polyrnerase chain reaction (PCR) and ligase chain reaction (LCR) as for example described in Chapter 15 of Ausubel et al. supra; strand displacement amplification (SDA) as for example described in U.S. Pat. No. 5,422,252; rolling circle replication (RCR) as for example described in International application WO 92/01813 and International Application WO 97/19193; nucleic acid sequence-based amplification (NASBA) as for example described by Sooknanan et al., 1994, Biotechniques 17 1077; and Q-β replicase amplification as for example described by Tyagi et al., 1996, Proc. Natl. Acad. Sci. USA 93 5395, although without limitation thereto.

A preferred nucleic acid sequence amplification technique is PCR.

As used herein, an "amplification product" refers to a nucleic acid product generated by a nucleic acid amplification technique as broadly defined herein.

A nucleic acid homolog may encode a protein homolog. Accordingly, the above-described methods for isolating a nucleic acid homolog may be used to isolate a protein homolog.

Isolated Snake Venom Protease Polypeptides

In another aspect, the invention features, an isolated snake venom protease protein, or fragment, e.g., a biologically active portion, for use as immunogens or antigens to raise or test (or more generally to bind) anti-snake venom protease antibodies. The snake venom protease protein can be isolated from cells or tissue sources using standard protein purification techniques. In one embodiment, the snake venom protease is isolated from a snake selected from the group of: *Pseudonaja textilis, Oxyuranus scutellatus, Notechis scutatus, Tropidechis carinatus* and *Pseudechis porphyriacus*. Preferably, the snake venom protease is isolated from the venom gland of an Australian snake, e.g., an Australian snake described herein. Snake venom protease protein or fragments thereof can be produced by recombinant DNA techniques or synthesized chemically.

Polypeptides of the invention include those which arise as a result of the existence of alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a snake venom protease polypeptide has one or more of the following characteristics:

(i) it has the ability to process prothrombin;

(ii) it has a molecular weight, e.g., a deduced molecular weight, preferably ignoring any contribution of post translational modifications, amino acid composition or other physical characteristic of a snake venom protease polypeptide, e.g., a polypeptide of SEQ ID NO:2, 5, 8, 11, 14 or 17;

(iii) it has an overall sequence similarity of at least 60%, more preferably at least 70, 80, 90, or 95%, with a snake venom protease polypeptide, e.g., a polypeptide of SEQ ID NO:2, 5, 8, 11, 14 or 17;

(iv) it has a substantial sequence identity with one or more of the domains or regions described herein, e.g., as described herein.

In a preferred embodiment, the snake venom protease protein, or fragment thereof, differs from the corresponding sequence in SEQ ID NO:2, 5, 8, 11, 14, or 17. In one embodiment, it differs by at least one but by less than 15, 10 or 5 amino acid residues. In another, it differs from the corresponding sequence in SEQ ID NO:2, 5, 8, 11, 14 or 17 by at least one residue but less than 20%, 15%, 10% or 5% of the residues in it differ from the corresponding sequence in SEQ ID NO:2, 5, 8, 11, 14 or 17. (If this comparison requires alignment the sequences should be aligned for maximum homology. "Looped" out sequences from deletions or insertions, or mismatches, are considered differences.) The differences are, preferably, differences or changes at a non-essential residue or a conservative substitution.

Other embodiments include a protein that contain one or more changes in amino acid sequence, e.g., a change in an amino acid residue which is not essential for activity. Such snake venom protease proteins differ in amino acid sequence from SEQ ID NO:2, 5, 8, 11, 14 or 17, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2, 5, 8, 11, 14 or 17, and has a snake venom protease biological activity.

In one embodiment, a biologically active portion of a snake venom protease protein includes one or more of: a GLA domain, an EGF-1 domain, an EGF-2 domain and a factor Va-like domain. Moreover, other biologically active portions, in which other regions of the protein are deleted, can be prepared by recombinant techniques and evaluated for one or more of the functional activities of a native snake venom protease protein.

In a preferred embodiment, the snake venom protease protein has an amino acid sequence shown in SEQ ID NO:2, 5, 8, 11, 14 or 17. In other embodiments, the snake venom protease protein is substantially identical to SEQ ID NO:2, 5, 8, 11, 14, or 17, and retains the functional activity of the protein of SEQ ID NO:2, 5, 8, 11, 14 or 17, as described in detail in the subsections above. In a preferred embodiment, the snake venom protease protein retains the ability to process prothrombin in the absence of one or more of calcium, phospholipids and factor Va, preferably it retains the ability to process prothrombin in the absence or both calcium and phospholipid.

Snake Venom Protease Chimeric or Fusion Proteins

In another aspect, the invention provides snake venom protease chimeric or fusion proteins. As used herein, a snake venom protease "chimeric protein" or "fusion protein" includes a snake venom protease polypeptide linked to a non-snake venom protease polypeptide. A "non-snake venom protease polypeptide" refers to a polypeptide having an amino acid sequence corresponding to a protein which is different from the snake venom protease protein and which is derived from the same or a different organism. The snake venom protease polypeptide of the fusion protein can correspond to all or a portion e.g., a fragment described herein of a snake venom protease amino acid sequence. In a preferred embodiment, a snake venom protease fusion protein includes at least one (or two) biologically active portion of a snake venom protease protein. The non-snake venom protease polypeptide can be fused to the N-terminus or C-terminus of the snake venom protease polypeptide. In one embodiment, the "non-snake venom protease polypeptide" is a pro-peptide from a prothrombotic activating protein other than a snake venom protease, e.g., it is a propeptide from mammalian factor Xa, e.g., human factor Xa. In another embodiment, the "non-snake venom protease polypeptide" can include an activator peptide from a prothrombotic activating protein other than a snake venom protease, e.g., an activator peptide from mammalian factor Xa, e.g., human factor Xa. In yet another embodiment, the chimeric or fusion polypeptide can include a propeptide and an activator peptide from a "non-snake venom protease polypeptide", e.g., from a mammalian factor Xa polypeptide, e.g., a human factor Xa polypeptide.

The fusion protein can include a moiety which has a high affinity for a ligand. For example, the fusion protein can be a GST-snake venom protease fusion protein in which the snake venom protease sequences are fused to the C-terminus of the GST sequences. Such fusion proteins can facilitate the purification of recombinant snake venom protease. Alternatively, the fusion protein can be a snake venom protease protein containing a heterologous signal sequence at its N-terminus. In certain host cells (e.g., mammalian host cells), expression and/or secretion of snake venom protease can be increased through use of a heterologous signal sequence.

Fusion proteins can include all or a part of a serum protein, e.g., an IgG constant region, or human serum albumin.

The snake venom protease fusion proteins of the invention can be incorporated into pharmaceutical compositions and administered to a subject in vivo. The snake venom protease fusion proteins can be used to affect the bioavailability of a snake venom protease substrate.

Moreover, the snake venom protease-fusion proteins of the invention can be used as immunogens to produce anti-snake venom protease antibodies in a subject, to purify snake venom protease ligands and in screening assays to identify molecules which inhibit the interaction of snake venom protease with a snake venom protease substrate.

Expression vectors are commercially available that already encode a fusion moiety (e.g., a GST polypeptide). A snake venom protease-encoding nucleic acid can be cloned into such an expression vector such that the fusion moiety is linked in-frame to the snake venom protease protein.

Variants of Snake Venom Protease Proteins

In another aspect, the invention also features a variant of a snake venom protease polypeptide, e.g., which functions as an agonist (mimetics) or as an antagonist. Variants of the snake venom protease proteins can be generated by mutagenesis, e.g., discrete point mutation, the insertion or deletion of sequences or the truncation of a snake venom protease protein. An agonist of the snake venom protease proteins can retain substantially the same, or a subset, of the biological activities of the naturally occurring form of a snake venom protease protein. An antagonist of a snake venom protease protein can inhibit one or more of the activities of the naturally occurring form of the snake venom protease protein by, for example, competitively modulating a snake venom protease-mediated activity of a snake venom protease protein. Thus, specific biological effects can be elicited by treatment with a variant of limited function.

Variants of a snake venom protease protein can be identified by screening combinatorial libraries of mutants, e.g., truncation mutants, of a snake venom protease protein for agonist or antagonist activity.

Libraries of fragments e.g., N terminal, C terminal, or internal fragments, of a snake venom protease protein coding sequence can be used to generate a variegated population of fragments for screening and subsequent selection of variants of a snake venom protease protein. Variants in which a cysteine residues is added or deleted, in which a calcium binding residue, e.g., a carboxyglutamic acid residue or asparganine, is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of snake venom protease proteins. Recursive ensemble mutagenesis (REM), a new technique which enhances the frequency of functional mutants in the libraries, can be used in combination with the screening assays to identify snake venom protease variants (Arkin and Yourvan (1992) *Proc. Natl. Acad. Sci. USA* 89:7811-7815; Delgrave et al. (1993) *Protein Engineering* 6:327-331).

In another aspect, the invention features a method of making a snake venom protease polypeptide, e.g., a peptide having a non-wild type activity, e.g., an antagonist, agonist, or super agonist of a naturally occurring snake venom protease polypeptide, e.g., a naturally occurring snake venom protease polypeptide. The method includes: altering the sequence of a snake venom protease polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a snake venom protease polypeptide having a biological activity of a naturally occurring snake venom protease polypeptide. The method includes: altering the sequence, e.g., by substitution or deletion of one or more residues, of a snake venom protease polypeptide, e.g., altering the sequence of a non-conserved region, or a domain or residue described herein, and testing the altered polypeptide for the desired activity.

Anti-Snake Venom Protease Antibodies

In another aspect, the invention provides an anti-snake venom protease antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-snake venom protease antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., snake venom protease polypeptide or fragment thereof. Examples of antigen-binding fragments of the anti-snake venom protease antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-snake venom protease antibody can be a polyclonal or a monoclonal antibody. In other embodiments, the antibody can be recombinantly produced, e.g., produced by phage display or by combinatorial methods.

Phage display and combinatorial methods for generating anti-snake venom protease antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 2:1373-1377; Hoogenboom et al. (1991) Nuc Acid Res 19:4133-4137; and Barbas et al. (1991) PNAS 88:7978-7982, the contents of all of which are incorporated by reference herein).

In preferred embodiments an antibody can be made by immunizing with purified snake venom protease antigen, or a fragment thereof, e.g., a fragment described herein, tissue, e.g., crude tissue preparations, whole cells, preferably living cells, lysed cells, or cell fractions.

A full-length snake venom protease protein or, antigenic peptide fragment of a snake venom protease can be used as an immunogen or can be used to identify anti-snake venom protease antibodies made with other immunogens, e.g., cells, membrane preparations, and the like. The antigenic peptide of snake venom protease should include at least 8 amino acid residues of the amino acid sequence shown in SEQ ID NO:2, 5, 8, 11, 14 or 17 and encompasses an epitope of a snake venom protease. Preferably, the antigenic peptide includes at least 10 amino acid residues, more preferably at least 15 amino acid residues, even more preferably at least 20 amino acid residues, and most preferably at least 30 amino acid residues. In preferred embodiments, the anti-snake venom protease antibody binds to a region, domain or site of a snake venom protease described herein. Antibodies reactive with, or specific for, any of these regions, or other regions or domains described herein are provided.

Antibodies which bind only native snake venom protease protein, only denatured or otherwise non-native snake venom protease protein, or which bind both, are with in the invention. Antibodies with linear or conformational epitopes are within the invention. Conformational epitopes can sometimes be identified by identifying antibodies which bind to native but not denatured snake venom protease protein.

Preferred epitopes encompassed by the antigenic peptide are regions of snake venom proteases which are located on the light or heavy chain, hydrophilic regions, as well as regions with high antigenicity.

In preferred embodiments, antibodies can bind one or more of purified antigen, tissue, e.g., tissue sections, whole cells, preferably living cells, lysed cells, or cell fractions.

The anti-snake venom protease antibody can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target snake venom protease protein.

The antibody can be coupled to a compound, e.g., a label such as a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-snake venom protease antibody (e.g., monoclonal antibody) can be used to isolate a snake venom protease by standard techniques, such as affinity chromatography or immunoprecipitation. Moreover, an anti-snake venom protease antibody can be used to detect snake venom protease protein (e.g., in a cellular lysate or cell supernatant) in order to evaluate the abundance and pattern of expression of the protein. Anti-snake venom protease antibodies can be used diagnostically to monitor snake venom protease levels in tissue as part of a clinical testing procedure. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. The label may be selected from a group including a chromogen, a catalyst, an enzyme, a fluorophore, a chemiluminescent molecule, a lanthanide ion such as Europium (Eu$^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in U.S. patent Specifications U.S. Pat. Nos. 4,366,241, 4,843,000, and 4,849,338, all of which are herein incorporated by reference. Enzyme labels useful in the present invention include alkaline phosphatase, horseradish peroxidase, luciferase, b-galactosidase, glucose oxidase, lysozyme, malate dehydrogenase and the like. The enzyme label may be used alone or in combination with a second enzyme in solution.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a snake venom protease nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., snake venom protease proteins, fusion proteins, and the like).

The recombinant expression vectors of the invention can be designed for expression of snake venom protease proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The snake venom protease expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

In some embodiments, when used in a mammalian cell, the expression vector can provide for expression of the snake venom protease light chain and heavy chain and expression of a propeptide domain and/or activation peptide from a non-snake venom protease polypeptide, e.g., a non-snake venom protease prothrombin activating protein, e.g., a propeptide and/or activation peptide from a mammalian factor X, e.g., human factor X.

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a snake venom protease nucleic acid molecule within a recombinant expression vector or a snake venom protease nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a snake venom protease protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *CellI*23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a snake venom protease protein. Accordingly, the invention further provides methods for producing a snake venom protease protein, e.g., a snake venom protease protein described herein, using the host cells of the invention. In one embodiment, the method includes culturing the host cell of the invention (into which a recombinant expression vector encoding a snake venom protease protein has been introduced) in a suitable medium such that a snake venom protease protein is produced. In another embodiment, the method further includes isolating a snake venom protease protein from the medium or the host cell.

In another aspect, the invention features, a human cell, e.g., a hematopoietic stem cell, transformed with nucleic acid which encodes a subject snake venom protease polypeptide.

Informatics

The sequence of a snake venom protease is provided in a variety of media to facilitate use thereof. A recorded sequence, in contrast to a protein or nucleic acid, can be provided as a manufacture. Such a manufacture can provide a nucleotide or amino acid sequence, e.g., an open reading frame, in a form which allows examination, e.g., by sequence analysis programs or by direct inspection, of the manufacture using means not directly applicable to examining the nucleotide or amino acid sequences, or a subset thereof, as they exists in nature or in purified form. The sequence information can include, but is not limited to, SVP full-length nucleotide and/or amino acid sequences, partial nucleotide and/or amino acid sequences, polymorphic sequences including single nucleotide polymorphisms (SNPs), epitope or domain sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing an SVP sequence, e.g., analyzing structure, function, or relatedness to one or more other nucleic acid or amino acid sequences. The method includes: providing a SVP nucleic acid or amino acid sequence; comparing the SVP sequence with a second sequence, e.g., one or more preferably a plurality of sequences from a collection of sequences, e.g., a nucleic acid or protein sequence database to thereby analyze SVP. The method can be performed in a machine, e.g., a computer, or manually by a skilled artisan.

The method can include evaluating the sequence identity between a SVP sequence and a second sequence, e.g., database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a SVP sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a SVP sequence, or record, in machine-readable form; comparing a second sequence to the SVP sequence, e.g., analyzing the SVP sequence for the presence or absence of a particular motif or domain; thereby analyzing a sequence. Comparison can include comparing to sequences for sequence identity or determining if one sequence is included within the other, e.g., determining if the SVP sequence includes a sequence being compared. In a preferred embodiment the SVP or second sequence is stored on a first computer, e.g., at a first site and the comparison is performed, read, or recorded on a second computer, e.g., at a second site. E.g., the SVP or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

Libraries

The invention includes nucleic acid or protein libraries derived from one of the snakes disclosed herein, e.g., a brown, Taipan inland, Taipan coast, red belly, tiger or rough scale snake. Nucleic acid libraries can be genomic or cDNA libraries. cDNA libraries can be derived from particular tissues, e.g., venom gland tissues. A library will typically include at least $10^2$, $10^3$, $10^4$, $10^5$ or more diverse members. The nucleic acid library members can be inserted into vectors, e.g., expression vectors, e.g., inducible expression vectors.

Protein library members can be displayed in a number of ways, e.g., in phage display or cell display systems.

Arrays and Uses Thereof

In another aspect, the invention features an array that includes a substrate having a plurality of addresses. The array can be a nucleic acid array or a protein array. A nucleic acid array can display a nucleic acid library from one or more of the snakes referred to herein. A protein array can display a member of a protein, polypeptide or peptide library from one or more of the snakes referred to herein. Proteins or nucleic acids members are placed at identifiable addressed on the array. The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a member of a nucleic acid library, e.g., the sense or anti-sense strand. In one preferred embodiment, a subset of addresses of the plurality of addresses has a nucleic acid capture probe for a nucleic acid library member. Each address of the subset can include a capture probe that hybridizes to a different region of a library member.

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a SVP polypeptide or fragment thereof. The polypeptide can be a naturally-occurring interaction partner of SVP polypeptide. Preferably, the polypeptide is an antibody, e.g., an antibody described herein (see "Anti-SVP Antibodies," above), such as a monoclonal antibody or a single-chain antibody.

Pharmaceutical Compositions

The invention also provides pharmaceutical compositions that include a snake venom protease polypeptide of the invention and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. These carriers may be selected from a non limiting group including sugars, starches, cellulose and its derivatives, malt, gelatine, talc, calcium sulfate, vegetable oils, synthetic oils, polyols, alginic acid, phosphate buffered solutions, emulsifiers, polyethylene glycol and different molecular weights thereof, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference. Supplementary active compounds can also be incorporated into the compositions.

The pharmaceutical compositions of the invention can be used to promote or otherwise facilitate blood coagulation. Examples of use include administration to bleeding wounds such as during surgery or following injury or trauma. In one aspect, a snake venom protease polypeptide is the only blood-coagulating component present in the pharmaceutical composition. One advantage of pharmaceutical compositions of the invention is that blood coagulation occurs rapidly without a need for the sequential or combinatorial action of plural components such as co-factors. For example, additional components such as calcium ions, factor Va and phospholipids are not required. Thus, in some embodiments, the pharmaceutical composition does not include any co-factors, e.g., any of calcium, a phospholipid, factor Va, or vitamin K. In other embodiments, the pharmaceutical composition can include one or more, but not all, of calcium, a phospholipid and factor Va.

In some embodiments, the pharmaceutical composition can include an additional component or adjuvant. For example, the composition can include one or more of: an anti-microbial, e.g., an antibiotic, , an antiviral, an antifungal, an antiparasitic agent, an anti-inflammatory agent, an antihistamine, an anti-fibrolytic agent, and a growth factor. Examples of antibiotics include tetracycline, ciprofloxacin, gentamycin, cyclosporin cefotaxim, and the like. Examples of antivirals include gangcyclovir, zidovudine, amantidine, vidarabine, ribaravin, trifluridine, acyclovir, dideoxyuridine, and the like. Antifungals include, but are not limited to, diflucan, ketaconizole, nystatin, and the like. Antiparasitic agents such as pentamidine can be included. The composition may further include an anti-inflammatory agent such as α-1-antitrypsin, α-1-antichymotrypsin, and the like. Examples of growth factors which can be included in the composition are growth factors that promote the healing of wounds, including, but not limited to, angiogenins; endothelins; hepatocyte growth factor and keratinocyte growth factor; fibroblast growth factors, including fibroblast growth factor-1 (FGF-1), fibroblast growth factor-2 (FGF-2), and fibroblast growth factor-4 (FGF-4); platelet-derived growth factors (PDGF); insulin-binding growth factors (IGF), including insulin-binding growth factor-1 and insulin-binding growth factor-2; epidermal growth factor (EGF); transforming growth factors (TGF), including transforming growth factor-α and transforming growth factor-β; cartilage-inducing factors (CIF), including CIP-A and CIP-B; osteoid-inducing factor (OIF); osteogenin and other bone growth factors; bone morphogenetic growth factors (BMP), including BMP-1 and BMP-2; collagen growth factor; heparin-binding growth factors, including heparin-binding growth factor-1 and heparin-binding growth factor-2; cytokines; interferons; hormones. Other compounds that can be included in the composition include: vasoconstricting agents such as adrenalin, or anaesthetics, e.g., local anaesthetics.

The pharmaceutical composition can be formulated to promote stability of the snake venom protease, e.g., to reduce digestion, e.g., autodigestion, of the snake venom protease. The stability of the snake venom protease can be promoted, for example, by preparing providing the snake venom protease in a pharmaceutical composition having a pH of about 5 to 9, preferably about 6.5 to 7. The stability of the snake venom protease can also be stabilized by providing the snake venom protease in a pharmaceutical composition further includes, e.g., a stabilizer, such as a polyol. In such embodiments, the pharmaceutical composition can include about 5%, 10%, 20% or more of a polyol (or polyols). An example of a polyol which can be used in the pharmaceutical composition is glycerol. In other aspects, the stability of the snake venom protease can be increased by providing the snake venom protease in a crystallized, freeze-dried or lyophilized form. If the composition is frozen, the composition should be thawed prior to the time of use. In another embodiment, the invention features a composition which includes a snake venom protease, e.g., a snake venom protease described herein, and which has a pH of about 5 to 9, preferably about 6.5 to 7. The invention also features a composition which includes a snake venom protease, e.g., a snake venom protease described herein, and a stabilizing agent, e.g., a polyol, e.g., glycerol. The polyol can be present at about 5%, 10% or 20%.

The dosage of the composition comprising the snake venom protease depends upon the particular use of the snake venom protease, but the dosage should be an effective amount for the composition to perform its intended use. Data obtained from the cell culture assays and animal studies can be used in formulating a range of dosage for use in humans. Generally, for a composition comprising a snake venom protease that is an aqueous solution, it is believed that from about 1 ml to about 50 ml of such composition is sufficient to increase fibrin clot formation. However, depending on the use of the composition, the dosage can range from about 1 ml to about 200 ml.

In some embodiments, pharmaceutical compositions of the invention are topically administered to a wound, surgical incision or other location where blood loss is to be prevented. To this end, bandages, patches, gauze, surgical tape, cotton swabs or other absorbent materials or supportive matrices may be coated, impregnated or chemically bonded with a composition which includes a snake venom protease of the invention for topical administration. Also contemplated are pharmaceutical compositions in the form a fibrin glue or surgical sealant. Compositions of the invention can be in the form of creams, lotions, gels, sprays or aerosols for laparoscopic or open surgical or traumatic wound closure. Topical administration is desirable in thses applications. In addition, sutures and staples coated or chemically bonded with a composition which includes a snake venom protease can be used.

The pharmaceutical compositions can be included in a container, pack, or dispenser together with instructions for administration.

It is also contemplated that antifibrinolytic agents may be added to prevent lysis of the blood clot through the action of tissue plasminogen activator such as textilinin as described in International Publication WO 99/58569, aprotinin and EACA.

Also within the scope of the invention are kits comprising a snake venom protease or portion thereof described herein. The kit can include one or more other elements including: instructions for use; other reagents, e.g., one or more co-factors (e.g., one or more of calcium, a phospholipid, and factor Va), and/or other therapeutic agents (e.g., one or more of: an anti-microbial, e.g., an antibiotic, an antiviral, an antifungal, an antiparasitic agent, an anti-inflammatory agent, an antihistamine, an anti-fibrolytic agent, an analgesic ,and a growth factor); a diluent; devices, e.g., containers, e.g., sterile containers, or other materials for preparing the snake venom protease for administration; pharmaceutically acceptable carriers (e.g., a stabilizer); and devices or other materials for administration to a subject (e.g., syringes, applicators, bandages, spray or aerosol devices). The instructions can include instructions for therapeutic application including suggested dosages and/or modes of administration, e.g., in a patient with external and/or internal bleeding. In some applications, the snake venom protease will be reacted with other components, e.g., one or more co-factor, prior to administration. In other applications, the snake venom protease can be administered in combination with other components, e.g., one or more co-factor, and the kit can include instructions on the amount, dosage, and timing of administration of the snake venom protease and the other components.

In some embodiments, the snake venom protease may be supplied in lyophilized or freeze dried form. In such embodiments, the kit can include one or more of: instructions for thawing and/or hydrolyzing, and a pharmaceutically acceptable carrier or diluent. In some embodiments, the kit can include instructions for a diluent or a premeasured amount of a diluent.

Uses

The snake venom proteases of the invention have been found to effectively activate prothrombin by processing prothrombin to thrombin. Thrombin is a serine protease that cleaves fibrinogen to generate fibrin, and can act upon several blood factors including factors V, VIII and XIII to stabilize interaction between fibrin monomers, thereby enhancing clot formation. Accordingly, the invention features methods of activating prothrombin and increasing haemostasis by administering the snake venom proteases described herein. The method can include: administering a snake venom protease to a desired site in a subject in an amount effective to promote or increase fibrin clot formation, to thereby increase clotting and/or decrease blood or fluid loss. The term "desired site" refers to a location where the formation of a fibrin clot is desired. The compositions can be applied directly to the wound, other tissue or other desired site. Typically for external wounds it can be applied directly by any means, including spraying the wound. It can also be applied internally, such as during a surgical procedure.

In preferred embodiments, the subject is a mammal, e.g., a human. Since the snake venom proteases described herein are not from blood, concerns regarding the risk of blood born pathogens or other infectious agents which can be found in sealants, adhesives and hemostats obtained from components of blood are alleviated.

The snake venom proteases and compositions comprising the snake venom proteases described herein can be used in various applications including as a surgical sealant, an adhesive (e.g., a topical or surgical adhesive), or as a hemstat.

The methods, kits or pharmaceutical compositions of the invention can be used, e.g., for connecting tissues or organs, stopping or reducing bleeding, preventing or inhibiting bleeding, healing wounds, and/or sealing a wound. The methods, kits and pharmaceutical compositions can be used in various surgical settings including: surgery of the nervous system; surgery of the nose, mouth or pharynx; surgery of the respiratory system; surgery of the cardiovascular system; surgery of hemic or lymphatic systems; surgery of the digestive system; surgery of the urinary system; surgery of the reproductive system; surgery of the muscloskeletal system; surgery of the integumentary system; plastic surgery; orthopedic surgery, and transplant surgery. For example, the snake venom proteases can be used in vascular surgery include providing hemostasis for stitch hole bleeding of distal coronary artery anastomoses; left ventricular suture lines; aortotomy and cannulation sites; diffuse epimyocardial bleeding seen in reoperations; and oozing from venous bleeding sites, e.g. at atrial, caval, or right ventricular levels. The subject invention is also useful for sealing of dacron artery grafts prior to grafting, sealing tissues outside the body, stopping bleeding from damaged spleens (thereby saving the organ), livers, and other parenchymatous organs; sealing tracheal and bronchial anastomoses and air leaks or lacerations of the lung, sealing bronchial stumps, bronchial fistulas and esophageal fistulas; and for sutureless seamless healing ("Zipper" technique). The subject invention is further useful for providing hemostasis in corneal transplants, nosebleeds, post tonsillectomies, teeth extractions and other applications. See G. F. Gestring and R. Lermer, Vascular Surgery, 294-304, September/October 1983. Also, the pharmaceutical compositions of the invention are especially suited for individuals with coagulation defects such as hemophilia (e.g., Hemophilia A and Hemophilia B).

It has also been found that unlike factor Xa and trocarin, the snake venom proteases of the invention can activate descarboxyprothrombin. Descarboxyprothrombin is found, e.g., in subjects being treated with anticoagulants such as coumadin. Thus, the methods, kits and pharmaceutical compositions of the invention can be used to activate prothrombin and increase haemostasis in subjects being treated with an anticouagulant such as coumadin. The methods and compositions described herein can be used on these subjects during surgery or trauma without the need to inhibit or decrease coumadin treatment.

As discussed above, the snake venom protease may be formulated as part of a wound dressing, bandage, patch, gauze, surgical tape, cotton swabs or other absorbent materials or supportive matrices. The dressing and bandage are easy-to-use, requiring no advanced technical knowledge or skill to operate. They can even be self-administered as an emergency first aid measure. Such wound dressings and bandages can be used in various field applications, such as in trauma packs for soldiers, rescue workers, ambulance/paramedic teams, firemen, and in early trauma and first aid treatment by emergency room personnel in hospitals and clinics, particularly in disaster situations. Such dressings may also have utility in first aid kits for use by the general public or by medical practitioners. The snake venom protease containing wound dressing or bandage can further include one or more of calcium, a phospholipid, a stabilizing agent, or other compound or agent such as those described herein. For example, the wound dressing or bandage can further include: an analgesic, an antiviral, an antifungal, an antiparasitic agent, an anti-inflammatory agent, an antihistamine, an anti-fibrolytic agent, and a growth factor.

More than one compound other than the snake venom protease can be added to the composition, to be released simultaneously, or each can be released in predetermined time-release manner. The additional compound (or compounds) added to the composition can be added at a concentration such that it will be effective for its intended purpose, e.g., an antibiotic will inhibit the growth of microbes, an analgesic will relieve pain, etc. In some embodiments, the dressing or bandage can include an adhesive layer and/or backing layer. The backing of the dressing or bandage may be of conventional, non-resorbable materials, e.g., a silicone patch or plastic material; or it may be of biocompatible, resorbable materials, e.g., chitin or its derivatives.

For other applications such as for use as a surgical sealant or surgical adhesive, the pharmaceutical compositions can in the form a fibrin glue or surgical sealant that may be in the form of creams, lotions, gels, sprays, foam or aerosols. For foams, sprays and aerosols, the composition can be stored in a canister or tank with a pressurized propellant, so that the components are delivered to the wound site as an expandable foam or spray. In a preferred embodiment, the spray, foam or aerosol is provided in a metered dose. In such embodiments, the methods can include providing a subject with the spray, aerosol, or foam in a metered dose and providing the subject with instructions for administering the spray, aerosol or foam, e.g., to a wound. The instructions can be for self-administration or administration to others.

Although the speed with which the composition forms clots may be to some degree dictated by the application, e.g., rapid setting for arterial wounds and hemorrhaging tissue damage, slower setting for treatment of wounds to bony tissue. Preferably, clotting is evident within ten minutes after application. Most preferably, clotting will be evident within two to eight minutes after application.

This invention is further illustrated by the following examples that should not be construed as limiting. The contents of all references, patents and published patent applications cited throughout this application are incorporated herein by reference.

EXAMPLES

Materials and Methods

Materials

A Brown snake venom protease complex was prepared by a method as described in Masci et al., 1988, Biochem. Int. 17 825, incorporated herein by reference. 4 mg/ml of prothrombin activator was stored in 50% glycerol at −20° C. Sephacryl S-300 was obtained from Amersham Pharmacia Biotech., Uppsala, Sweden, and the synthetic chromogenic substrate S-2222 was obtained from Chromogenex, Stockholm, Sweden. Outdated citrated plasma was obtained from normal, virus-screened volunteers made available by Princess Alexandra Hospital Blood Bank. Hampton 1 and 2 screen kits were obtained from Hampton Research, United States of America. Wizard 1 and 2 screen kits were obtained from Emerald Biostructures, United Kingdom.

Brown Snake Venom Protease Purification

ConA-Sepharose 4B

The first step in the purification of *P. textilis*-snake venom protease was to isolate Brown snake venom protease complex from crude venom, as described in Masci et al., 1988, supra. Con A-Sepharose 4B was packed into a 2.5×16 cm column, washed as recommended by the manufacturer and equilibrated with starting buffer (0.05 M Tris-HCl, pH 7.4). *P. textilis* venom (233 mg dry weight) was reconstituted in 10 ml starting buffer and placed into a 37° C. water bath until dissolved. The sample was loaded onto the column and washed with column buffers until the baseline returned to zero. Elution buffer (0.02 M methyl α-D mannopyranoside in 0.05 M Tris-HCl) was applied to the column to elute bound protein (Brown snake venom protease complex) from the Con A-Sepharose 4B. The flow rate of the column was 52 ml/hour. The UV dual wavelength detector was set at 280 mm with attenuations of 0.32 and 0.64 absorbance units full scale (AUFS). Fractions with S-2222 hydrolytic activity were pooled and concentrated in an Amicon concentrator, model 405, with a YM3 membrane, having a flow rate of 48 mL/hour. Purified Brown snake venom protease complex was stored in 50% glycerol at −20° C.

Brown Snake Venom Protease Purification from Brown Snake Venom Protease Complex

Sephacryl S-300 Chromatography

Sephacryl S-300 chromatography gel was washed as recommended by the manufacturer. An 87 cm×2.5 cm column of Sephacryl S-300 was packed at 6° C., and equilibrated with starting buffer (0.05 M Tris-HCl buffer, pH 7.4), followed by the equilibration with two column volumes of the same buffer with added 0.8 M NaSCN prior to application of sample. 10 ml of 4 mg/ml prothrombin activator and 10 ml of 1.6 M NaSCN was incubated for 10 min and loaded onto the column. A Gilson peristaltic pump was set up with a purple/black chamber, in order to give a flow rate of 40 ml/hr. An Altex UV dual wavelength detector, set at $A_{280}$ with an attenuation of 0.32 AUFS, with a Cole Palmer 2 pen chart recorder, set at 1 cm/hr were used. Fractions were collected using time base at time intervals of 10 min/tube initially, followed by a change to 12 min/tube giving 6.5 and 8 ml fractions respectively, using a LKB 7000 fraction collector. Chromogenic assays, as described above, were performed to assess fractions with hydrolytic activity, which were pooled and concentrated in an Amicon concentrator, model 42, with a YM3 membrane. This procedure was repeated three times.

Superdex 200 Gel Chromatography

Superdex 200 high resolution gel chromatography was also used to purify protease from Brown snake venom protease complex. The Superdex 200 was washed as recommended by the manufacturer, packed into a 2.5×90 cm column, and equilibrated with column buffer (0.05 M Tris-HCl, pH 7.4, 0.8 M NaSCN). A solution comprising 9 mL of 5.6 mg/mL Brown snake venom protease complex and 9 mL 1.6 M NaSCN was incubated for 30 min, then loaded onto the column. The flow rate was 48 mL/hour. The attenuation of the wavelength detector at 280 mn was 0.32 or 0.64 AUFS. Fractions with S-2222 activity were pooled and concentrated in an Amicon concentrator, model 52, with a YM3 membrane. The pooled concentrated sample (5 mL) was then rechromatographed on the same column. The final protease preparation was dialyzed overnight in 0.05 M Tris-HCl, pH 7.4, to remove NaSCN from the solution. This preparation (stored in 10% glycerol/Tris buffer at −20° C.) was used for all functional and structural characterization studies.

High Performance Liquid Chromatography (HPLC)

Reverse-phase HPLC was performed 25° C., using a Waters (TM) system consisting of a 6000A dual piston pump and M45A pump, a 490 wavelength detector set at $A_{280}$ nm, and a Wisp sample injector and a Phemonenex Jupiter $C_{18}$-column (KHO-4154) (1.4 mm×250 mm). Chromatography was carried out using a linear gradient mode over 60 min with a starting solution, (A) 0.1% TFA in distilled water and eluted with (B) 80% acetonitrile in (A). Waters Millenium version 1.01 software was used to manage the system and integrate the data.

Sodium Dodecyl Sulfate (SDS) Polyacrylamide Gel Electrophoresis (PAGE)

SDS PAGE was performed essentially as described by Laemlli, 1970, Nature 227 680. SDS-PAGE samples were boiled for 10 min in SDS sample buffer in the presence or absence of β-mercaptoethanol (β-Me). Gels were stained with Coomassie blue and destained with methanol, acetic acid and water (45:10:45).

N-Terminus Amino Acid Sequencing

Sequencing was performed using the Edman Degradation method. An Applied Biosytems Procine 492cLC Protein Sequencing System was used to sequence the Brown snake venom serine protease. Refer to Applied Biosystems Manual, part no. 904 244, revision D for details of equipment. Searches were then performed using ExPAsy/NCBI blast to identify sequence homology between the reptilian serine protease and Factor Xa, and the *T. carinatus* Factor Xa-like serine protease.

First-Strand cDNA Synthesis and Amplification of cDNA Ends

1 μg of total RNA isolated from snake gland was used for cDNA synthesis. For preparation of 5'RACE-Ready cDNA we used 5'-CDS [5'-(T)$_{25}$N$_{-1}$N-3'; N=A, C, G, or T; N$_{-1}$=A, G, or C] [SEQ ID NO: 32] and SMART II A oligo [5'-AAGCAGTGGTATCAACGCAGAGTACGCGGG-3'] [SEQ ID NO: 33] primers from SMART RACE cDNA Amplification Kit, and for preparation of 3'RACE ready cDNA -3'-CDS primer A [ 5'-AAGCAGTGGTATCAACG-CAGAGTAC(T)$_{30}$N$_{-1}$N-3'; N=A,C,G, or T; N$_{-1}$=A,G, or C] [SEQ ID NO: 34] and PowerScript Reverse Transcriptase from the same Kit. Both cDNA were diluted by adding 100 μl of water and used for Rapid Amplification of cDNA Ends (RACE) according to the protocol described in User Manual (SMART RACE cDNA Amplification Kit, Clontech).

For 3'RACE PCR: 3'RACE cDNA, UPM [Universal Primer Mix A 5'-CTAATACGACTCACTATAGGGCAAG-CAGTGGTATCAACGCAGAGT-3' (long) [SEQ ID NO: 35] and 5'-CTAATACGACTCACTATAGGGC-3' (short) [SEQ ID NO: 36] and degenerate GSP-2 (forward) primer [AAYG-GWATGGAYTGYAA; Y=C+T,W=A+T] [SEQ ID NO: 37] based on the N-terminal amino acid sequence IVNGMD. Advantage 2 Polymerase Mix (Clontech) was used to prime the reaction. Thermal Cycler: 1 cycle: 95° C. 1 min; 25 cycles: 95° C. 30 sec, 65° C. 1 min, 68° C. 3 min; 1 cycle: 68° C. 3 min. Main PCR-product (1.5 kbp) was isolated from gel using QIAquick Gel extraction Kit (Qiagen) and cloned in pGEM-T Easy Vector. After screening the colonies minipreps from 35 colonies were isolated using QIAprep Spin Miniprep Kit (Qiagen).

DNA Sequencing

DNA sequencing was performed using BigDye Terminator and forward primer to pGEM-T Easy Vector (GTTTTC-CCAGTCACGAC) [SEQ ID NO: 38]. Only 2 clones not containing stop codon within ca 500 bp were discovered. These clones were sequenced with For2 primer (ATCGT-TAGTGGATTTGG) [SEQ ID NO: 39]. Stop codon was discovered. The full sequence of these two clones was similar and the length of 3'-DNA from GSP-2 until first stop codon was 776 bp.

Using 3'cDNA sequence the reverse primer GSP-1 was designed: GAAATCGTCTCGGTCTCATTA [SEQ ID NO: 40]. For 5'RACE PCR 5'cDNA, UPM (see above), GSP-1 and Advantage 2 Polymerase Mix (Clontech) was used. PCR conditions were the same as for 3'RACE PCR. Main PCR product (1 kbp) was isolated and cloned in pGEM-T Easy Vector. From 15 clones selected for sequencing 6 were the same, and did not contain stop codons. Two sequencing primers were used: forward to pGEM-T Easy Vector (see above) and reverse primer GSP-1. All six clones contained ATG and were 628 bp from start to the position corresponding to GSP-2 primer sequence. 3' and 5' cDNA sequences were used to design forward and reverse primers for full-length cDNA: SE(forward) ATGGCTCCTCAACTACTCCTCTG [SEQ ID NO: 41] and SE(reverse) TTAGAGCCGACCAGTGCT-TGACTC [SEQ ID NO: 42]. PCR-product (1.407 bp) was cloned in pGEM-T Easy Vector for sequencing.

Chromogenic Prothrombin Activation Assays for Brown Snake Venom Protease Complex A series of assays were performed to obtain standard curves for a rate of S-2222 hydrolysis verses an amount of Brown snake venom protease complex or Brown snake venom protease. Respective dilutions of Brown snake venom protease complex (4 mg/ml) and protease (1 mg/ml) varying from 1/10 to 1/10,000 were made in 0.05 M Tris-HCl, pH 7.4 and stored on ice.

Hydrolytic activity of *P. textilis* serine protease or the Brown snake venom protease complex on S-2222 was determined by equilibration of 0.93 ml of 0.05 M Tris-HCl buffer, pH 7.4, with or without 10 mM $CaCl_2$ and 50 μl of 3.0 mM S-2222 in the 1 ml cell of a Hitachi 557 spectrophotometer at 25° C. The reaction was initiated by addition of varying concentrations of 20 μl of protease (0.4 mg/ml). The release of p-nitroaniline was monitored at 405 nm. Assays with 0.91 ml of 0.05 M Tris-HCl buffer, pH 7.4, containing 0.8 M NaSCN, 50 μl of S-2222 and 40 μl of 0.4 mg/ml Brown snake venom protease complex were performed at time intervals of 0, 1, 2, 5 and 10 minutes. One unit of activity is equivalent to the hydrolysis of 1 μmol of substrate/min.

Prothrombin Activation Assays for Brown Snake Venom Protease

Brown snake venom protease (5 μg) was added to 2 mL 0.25 mg/mL prothrombin (in 0.05 M Tris-HCl, pH 7.4). Alquots (20 μL) of this solution were taken at various time intervals and chromogenic assays with the thrombin-selective substrate S-2238 were performed. These assays consisted of 930 μL 0.05 M Tris-HCl, pH 7.4, 50 μL S-2238 and the 20 μL sample. The rate of substrate hydrolysis was measured at 405 nm. Two 20 μL aliquots were also taken at each time interval for SDS PAGE analysis±β-mercaptoethanol.

Clotting Assay

Citrated plasma clotting assays were performed using a Hyland-Clotek machine as described by Austen & Rhymes In: A laboratory manual of blood coagulation. Blackwell Scientific Publishers, Oxford UK 1975. The assays consisted of 100 μl of 0.05 M Tris-HCl buffer, pH 7.4, 100 μl of citrated human plasma and 20 μl of a varied concentration of protease. Identical assays were also performed with or without 0.04 M $CaCl_2$, and with 0.8 M NaSCN taking aliquots at time intervals.

Fibrin Formation in Citrated Plasma by Brown Snake Venom Protease

Human citrated plasma (970 µl) was mixed with:

(1) 20 µl 1.16 mg/mL protease;

(2) 20 µl 1.16 mg/mL protease and 10 µl 4 M $CaCl_2$ to give a final $Ca^{2+}$ concentration of 40 mM (concentration of free $Ca^{2+}$~10 mM);

(3) 10 µl 4 M $CaCl_2$.

Each solution was made up to 1 mL by the addition of 0.05 M Tris-HCl, pH 7.4. The three solutions were left for 4 hours and the resulting clots were pressed and washed several times with $dH_2O$ to remove other plasma proteins from the fibrin clots. The clots were then added to Eppendorf tubes containing 500 µL 4×SDS sample buffer with β-mercaptoethanol and 4 M urea. An additional drop of β-mercaptoethanol was added to each Eppendorf tube and left overnight. The samples were boiled for 5 min and 10 µL of each run on a SDS PAGE acrylamide gel as described herein.

Active Site Labelling of Brown Snake Venom Protease Complex and Brown Snake Venom Protease Samples (120 µl) of solutions Brown snake venom protease complex (4 mg/mL) and Brown snake venom protease (2 mg/mL) were reacted with 15 µL 40 mM DNS-GGACK (4 mM final concentration in 0.05 M Tris-HCl, pH 7.4) for 1 hour. The samples were then dialysed overnight with a magnetic stirrer at 4° C. in 0.05 M Tris-HCl, pH 7.4, to remove excess inhibitor. SDS PAGE was then performed with and without β-mercaptoethanol on both labelled and unlabelled Brown snake venom protease complex and protease. The gel with active site labelled proteins was visualized under ultraviolet light, whereas the other gel was stained with Coomassie Blue.

Fibrin Glue studies

Outdated citrated plasma (3.5 ml) was dispensed into 20 ml conical plastic vials at 37° C. water bath. 20 µl of 2 mg/ml Brown snake venom serine protease was added to both vials. 0.025 M $CaCl_2$ was added to one and saline was added to the other vial. Clotting time was monitored visually and when firm clots formed they were placed on no. 54 filter paper and pressed. The resulting pressed clots were extensively washed in distilled water and stored overnight at 4° C. The clots were photographed to review texture.

Results

As shown herein, and exemplified by P. textilis, the snake venom protease complex comprises a protease characteristic of a Factor Xa-like serine protease and a number of other proteins with unknown function. The isolated snake venom proteases from P. textilis, O. scutellatus, N. scutatus, T. carinatus and P. porphyriacus may be useful for the preparation of a pharmaceutical composition in the form of a topical fibrin "glue" or "sealant".

Some of the experiments herein have been performed using P. textilis derived samples and proteins. However, it will be appreciated by a person skilled in the art that these experiments are examples characterising a snake venom protease complex and snake venom protease that may be applicable to the other snake venom proteases of the invention.

Purification of Snake Venom Proteases

Purification of Brown Snake Venom Protease Complex (ConA-Sepharose 4B)

The first step in the purification of P. textilis-snake venom protease was to isolate Brown snake venom protease complex from crude venom. A method based on that described by Masci et al, 1988, supra was used. An elution profile at 280 nm resulting from chromatography of 233 mg dry weight of crude P. textilis venom on ConA-Sepharose 4B is shown in FIG. 1 (a trace of original chromatogram).

The venom was resolved into two major protein peaks, one that bound to ConA-Separose 4B and had activity against the factor Xa substrate S-2222 (indicated by line at A in FIG. 1). Based on $A_{280}$ measurements, the activity peak represented approximately 30% of total venom protein.

Results of SDS PAGE of the pooled Brown snake venom protease complex concentrate from ConA-Sepharose 4B chromatography are shown in FIG. 2; lane 1: Molecular weight markers (sizes are shown in kDa), lane 2: Brown snake venom protease complex without β-mercaptoethanol, lane 3: Brown snake venom protease complex with β-mercaptoethanol.

Arrow A indicates an intact Brown snake venom protease band in lane 2, whereas arrows B and C designate respective heavy and light chains of Brown snake venom protease in lane 3 (see below).

Brown snake venom protease complex, in the absence of β-mercaptoethanol (lane 2), comprises a single dominant broad protein band at ~150-200 kDa, and three other major bands with molecular masses of ~60, 50 and 45 kDa. Summing the approximate masses of the three major bands in lane 2 results in a predicted calculated mass of 300-350 kDa for the intact complex.

Brown snake venom protease complex in the presence of β-mercaptoethanol (lane 3) separates into several protein bands with respective apparent molecular masses of 110, 93, 80, 55, 46, 40 and a broad band (possibly a doublet) at ~32-34 kDa. The differences between lanes 2 and 3 indicate that disulfide bonds appear to link some of the polypeptides in the complex together.

The protease component of the Brown snake venom protease complex exists as a visible doublet in lane 2 at ~50-60 kDa, as indicated by arrow A. The heavy chain of the protease presents as a band at about 40 kDa (indicated by arrow B), and the light chain of the protease has an approximate mass of 32 kDa (indicated by arrow C). This designation of the SDS PAGE bands A, B and C was confirmed by the isolation and characterization experiments described herein. Some of the bands in FIG. 2 may represent venom impurities in the Brown snake venom protease complex.

Purification of the Protease Component from the Brown Snake Venom Protease Complex Sephacryl S-300 Chromatography To isolate the Brown snake venom Factor Xa-like serine protease component of the Brown snake venom protease complex, it was necessary to dissociate the complex. Speijer et al (1986) showed 0.8 M NaSCN could efficiently dissociate the O. scutellatus-prothrombin activator, but never attempted to purify it with 0.8 M NaSCN in the chromatography procedure. To illustrate an ability to dissociate the Brown snake venom protease complex with 0.8 M NaSCN, the following experiments were performed and the results are provided in FIG. 3. 0.8 M NaSCN added to Brown snake venom protease complex caused a rapid decrease in the citrated plasma clotting activity from less than 10 sec to greater than 60 sec, however, most S-2222 activity was essentially retained.

Brown snake venom protease complex treated with 0.8 M NaSCN was separated into individual components by gel filtration chromatography on a Sephacryl S-300 column, equilibrated with a 0.8 M NaSCN containing buffer.

Fractions 30-43 showed S-2222 hydrolysis activity. The fraction volume was increased for the remaining chromatography steps from 6.5 ml/tube to 8 ml/tube to reduce the number of fractions. A second Sephacryl S-300 chromatography was performed with pooled and concentrated fractions 30-43. S-2222 hydrolytic activity was observed in fractions 25-29. A third Sephacryl S-300 chromatography with the pooled and concentrated fractions 25-29. Essentially it gave a single protein peak having S-2222 hydrolytic activity in fractions 25-29. A high degree of homogeneity was confirmed by HPLC (FIG. 4). Based on HPLC, the Brown snake venom serine protease is greater than 95% pure.

Tables 1-6 summarise purification results and characterisation of samples from sets of experiments.

SDS PAGE±β-Me of Sephacryl S-300 Gel Filtration Products

SDS PAGE was performed with pooled fractions from all chromatography steps, shown in FIG. 5. Lane 4 (containing Sephacryl S-300, chromatography step 1, pooled fractions 30-43) shows a homogenous preparation of pooled Brown snake venom serine protease was not attained since a contaminant exists at a molecular weight of approximately 107 kDa. Lane 5 (containing Sephacryl S-300, chromatography step 2, pooled fractions 25-29) shows a greater percentage of a 55-56 kDa component but still containing a contaminant requiring a third chromatography. Lanes 6-8, with varying quantities of the Sephacryl S-300 pooled fractions 25-29 from the third chromatography step, show a homogeneous preparation. The molecular weight of the intact Brown snake venom serine protease appears to be between 55 and 56 kDa seen in Lanes 5-8.

The Brown snake venom serine protease has been compared with both whole *P. textilis* venom (Lane 2) and intact Brown snake venom protease complex, with (Lane 10) and without β-Me (Lane 3). This showed the position of Brown snake venom serine protease within the complex and in whole venom.

Lane 9 of FIG. 5 shows reduction of the Sephacryl S-300 pooled fractions 25-29 from chromatography step 3, with β-Me. A single band with a molecular weight of approximately 31 kDa can be seen. A second gel separation was performed to identify the expected two bands that should have resulted from reduction of the Brown snake venom serine protease. This gel is shown in FIG. 6.

SDS PAGE of Sephacryl S-300 pooled and concentrated fractions 25-29, with or without β-Me, can be seen in FIG. 6. Lanes 3 (containing Sephacryl S-300, chromatography step 3, pooled fractions 25-29), 4 and 6 (containing Sephacryl S-300 pooled and concentrated fractions 25-29 from chromatography 3) shows a homogeneous preparation of Brown snake venom serine protease was achieved. However, both Lanes 3 and 6 bands were very faint. The molecular weight of the Brown snake venom serine protease appears to be between 55 and 56 kDa, corresponding with the result in FIG. 5.

Lane 5 (containing Sephacryl S-300 pooled and concentrated fractions 25-29 from chromatography 3 with β-Me) shows that the Brown snake venom serine protease contains 3 subunits, however the last band could be a dye front, which is often seen with the Laemlli method, or it could be a product of self digestion. Lane 7 (comprising Sephacryl S-300, chromatography step 3, pooled and concentrated fractions 25-29+β-Me) shows no band and Lane 8 (comprising Sephacryl S-300 pooled and concentrated fractions 25-29 from chromatography 3+β-Me) shows that the Brown snake venom serine protease is comprised of heavy and light chains. It is assumed that the Brown snake venom serine proteases comprise heavy and light chains based on the corresponding Factor Xa and *O. scutellatus* serine protease structure. The molecular weight of the Brown snake venom serine protease heavy chain appears to be approximately 31 kDa, corresponding with the result in FIG. 5, and the light chain about 18 kDa. *P. textilis* whole venom (Lane 2) and intact Brown snake venom protease complex with β-Me (Lane 9) was included in the gel so a comparison could be made with the bands representing Brown snake venom serine protease.

Superdex 200 Gel Filtration

In an attempt to improve the purification of Brown snake venom protease, a higher resolution gel filtration medium (Superdex 200) was alternatively used instead of Sephacryl S-300. The elution profiles at 280 nm after chromatography and rechromatography of Brown snake venom protease complex on Superdex 200 in the presence of NaSCN are shown in FIGS. 10A and 10B. FIGS. 10A and 10B show an elution profile after chromatography of Brown snake venom protease complex (18 mL; 50.4 mg) on a column (2.5×90 cm) of Superdex 200 in 0.05 M Tris-HCl, pH 7.4 with 0.8 M NaSCN. FIG. 7A shows chromatography step 1 and FIG. 7B shows chromatography step 2. At each step fractions with S-2222 activity were pooled and concentrated, designated by line at A.

Samples from purification of Brown snake venom protease with Superdex 200 were separated by SDS PAGE after each purification step as shown in FIG. 7C. Lanes 1 and 2: pooled concentrate from chromatography step 1 with (lane 2) and without (lane 1) β-mercaptoethanol; lanes 3 and 4: pooled concentrate from chromatography step 2 with (lane 5) and without (lane 4) β-mercaptoethanol; lane 5: molecular weight markers (sizes are shown in kDa); arrows A, B and C indicate impurities in lane 4.

The specific activity of the starting material used in the Superdex 200 purification was substantially less than that of the starting material used in the Sephacryl S-300 chromatography (Table 2). This may reflect different activities of different venom samples. The final product from Superdex 200 purification had a specific activity of 1.1 U/mL/$A_{280}$, less than half the 2.4 U/mL/$A_{280}$ of the Sephacryl S-300 product.

Other methods of isolation are contemplated including ion-exchange chromatography, urea as an alternative dissociating agent, purification of the Brown snake venom protease from crude *P. textilis* venom using a one step ConA-Sepharose 4B purification procedure, affinity based on substrate specificity of the protease and other methods known in the art. The following are examples of suitable methods for isolating a prothrombin activating protein of the invention, exemplified with isolation of Brown snake venom protease. Tables 3-6 show properties of samples during purification at different steps.

Protocol 1

ConA-Sepharose (07-01-03)

Starting buffer, 0.05 M Tris-HCl, pH 7.4

Eluting buffer, 0.05 M Tris-HCl, 0.02 M methyl-α-D-mannopyranoside

Loading sample: dry venom (weight: 541 mg) from Venom Supplies was reconstituted in 10 ml starting buffer A280 of 1 ml solution: 13.5

Total A280 units loaded: 135

Activity of sample: 38 U/ml

Total activity units loaded: 377

Fractions with S-2222 activity pooled

A280 of concentrated pool was 6.8 and consisted of 10 ml.

Total A280 units pooled: 68

Activity of pool: 2.6 U/ml

Total activity units pooled: 26.0

Superdex 200 (13-01-03)

Starting buffer, 0.05 M Tris-HCl, pH 7.4, 0.8 M NaSCN

Loading sample: part of the pooled and concentrated peak from above ConA-Sepharose chromatography with added 0.8 M NaSCN (A280 8.9, 10 ml, 3.25 U/ml)

Total A280 units loaded: 89
Total activity units loaded: 32.5
Fractions with S-2222 activity pooled
A280 of concentrated pool was 0.350 and consisted of 20 ml
Total A280 units pooled: 7
Activity of concentrated pool: 0.46 U/ml
Total activity units pooled: 9.2
Superdex 200 (14-01-03)
Starting buffer, 0.05 M Tris-HCl, pH 7.4, 0.8 M NaSCN
Loading sample: pooled and concentrated fractions from previous Superdex 200 chromatography (A280 0.350, 20 ml, 0.46 U/ml)
Total A280 units loaded: 7
Total activity units loaded: 9.2
Fractions with S-2222 activity pooled
A280 of concentrated pool was 0.076 and consisted of 40 ml
Total A280 units pooled: 3.0
Activity of concentrated pool: 0.11 U/ml
Total activity units pooled: 4.4
Protocol 2
ConA-Sepharose (21-01-03)
Starting buffer, 0.05 M Tris-HCl, pH 7.4
Eluting buffer, 0.05 M Tris-HCl, 0.02 M methyl-α-D-mannopyranoside, then 0.05 M Tris-HCl, pH 7.4, 0.8 M NaSCN
Loading sample: dry venom (weight: 432 mg) from John Weigel was reconstituted in 10 ml starting buffer
280 of 1 ml solution: 25.6
Total A280 units loaded: 256
Activity of sample: 102.9 U/ml
Total activity units loaded: 1028
Fractions with S-2222 activity pooled
2 pools were made
1. concentrated fractions eluted with methyl-α-D-mannopyranoside (applied to phenyl-sepharose column)
A280 of concentrated pool was 0.95 and consisted of 22 ml
Total A280 units pooled: 20.9
Activity of pool: 5.0 U/ml
Total activity units pooled: 110
2. concentrated fractions eluted with NaSCN (only half of this was applied to two identical Superdex 200 chromatography steps below).
200 column as described below
A280 of concentrated pool was 1.85 and consisted of 27 ml.
Total A280 units pooled: 68
Activity of pool: 2.6 U/ml
Total activity units pooled: 26.0
Superdex 200 (29-01-03 and 30-01-03)
Starting buffer, 0.05 M Tris-HCl, pH 7.4, 0.8 M NaSCN
Loading sample: part of the pooled and concentrated peak from above ConA-Sepharose chromatography. Two identical chromatography steps were performed. A loading sample consisted of 16 ml of the pooled and concentrated peak from above ConA-Sepharose chromatography with added 0.8 M NaSCN:
A280 of 1 ml solution: 1.2
Total A280 units loaded: 19.2
Activity of sample: 15.7 U/ml
Total activity units loaded: 250.6
Fractions with high and identical specific activity from each of the chromatography steps were pooled and concentrated (other fractions also had S-2222 activity but the specific activity was lower, these were pooled separately):
A280 of concentrated pool was 1.9 and consisted of 9 ml Total A280 units pooled: 17.1
Activity of concentrated pool: 25.7 U/ml
Total activity units pooled: 231.3
Superdex 200 (04-02-03)
Starting buffer, 0.05 M Tris-HCl, pH 7.4 (without NaSCN)
Loading sample: pooled and concentrated fractions from previous Superdex 200 chromatography (A280 1.9, 9 ml, 25.7 U/ml)
Total A280 units loaded: 17.1
Total activity units loaded: 231.3
Fractions with S-2222 activity pooled (results below include fractions with the highest S-2222 activity, other fractions also had S-2222 activity and these were pooled separately)
A280 of concentrated pool was 1.7 and consisted of 9.5 ml
Total A280 units pooled: 16.2
Activity of concentrated pool: 17.7 U/ml
Total activity units pooled: 168.2
Protocol 3
ConA-Sepharose (10-02-03)
Starting buffer, 0.05 M Tris-HCl, pH 7.4
Eluting buffer, 0.025 M Tris-Acetate, pH 6.5, 4 M Urea
Loading sample: dry venom (weight: 557 mg) reconstituted in 25 ml starting buffer
A280 of 1 ml solution: 28
Total A280 units loaded: 700
Activity of sample: 83.4 U/ml
Total activity units loaded: 2087
Fractions with S-2222 activity pooled
A280 of pool was 0.592 and consisted of 640 ml.
Total A280 units pooled: 379
Activity of pool: 0.152 U/ml
Total activity units pooled: 97.3
CM-Sepharose (12-02-03)
Starting buffer, 0.025 M Tris-Acetate, pH 6.5, 4 M Urea
Loading sample: pooled fractions from ConA-Sepharose chromatography (A280 0.592, 640 ml, 0.152 U/ml)
Total A280 units loaded: 379
Total activity units loaded: 97
Once entire sample was loaded onto the column a 0-0.5 M NaCl gradient was applied
Fractions with S-2222 activity pooled
A280 of concentrated pool was 4.5 and consisted of 17.5 ml.
Total A280 units pooled: 79
Activity of concentrated pool: 1.44 U/ml
Total activity units pooled: 25
Superdex 200 (13-02-03)
Starting buffer, 0.05 M Tris-Acetate, pH 6.5
Loading sample: pooled and concentrated fractions from CM-Sepharose chromatography (A280 4.5, 17.5 ml, 1.44 U/ml)
Total A280 units loaded: 79
Total activity units loaded: 25
Fractions with S-2222 activity pooled (results below refer to a pooled symmetrical peak, other fractions had S-2222 activity also)
A280 of concentrated pool was 0.330 and consisted of 7.5 ml
Total A280 units pooled: 2.5
Activity of concentrated pool: 0.146 U/ml
Total activity units pooled: 1
Protocol 4
Phenyl-Sepharose (15-02-03)
Starting buffer, 0.8 M NaSCN-Phosphate, pH 6.5

Loading sample: pooled and concentrated fractions from ConA-Sepharose chromatography (A280 0.95, 22 ml, 5.03 U/ml)
Total A280 units loaded: 20.9
Total activity units loaded: 110
Once entire sample was loaded onto the column a 0.8-0 M NaSCN gradient was applied
Fractions with S-2222 activity pooled
A280 of concentrated pool was 0.485 and consisted of 9.5 ml
Total A280 units pooled: 4.6
Activity of concentrated pool: 1.4 U/ml
Total activity units pooled: 13
Superdex 200 (18-02-03)
Starting buffer, 0.05 M Tris-Acetate, pH 6.5
Loading sample: pooled and concentrated fractions from phenyl-sepharose chromatography (A280 0.485, 10 ml, 1.4 U/ml)
Total A280 units loaded: 4.85
Total activity units loaded: 14
Fractions with S-2222 activity pooled (two pools were made, the one described below comprises fractions with greatest activity)
A280 of concentrated pool was 0.327 and consisted of 3.5 ml
Total A280 units pooled: 1.14
Activity of pool: 1.83 U/ml
Total activity units pooled: 6.4

Characterisation of *P. Textilis*-Snake Venom Protease Complex

Effect of $Ca^{2+}$ on Hydrolysis of S-2222 Chromogenic Substrate by Brown Snake Venom Protease Complex To determine the snake venom protease complex Factor Xa-like cleavage specificity, chromogenic assays using the Factor Xa specific chromogenic substrate S-2222 were performed. Brown snake venom protease complex hydrolyses S-2222, with or without added $Ca^{2+}$. The initial rates of hydrolysis without $Ca^{2+}$ are similar to those in the presence of $Ca^{2+}$, but only at concentrations greater than 2 µg/ml of Brown snake venom protease complex (data not shown).

The rate of S-2222 hydrolysis by Brown snake venom protease complex was approximately linear with an amount of Brown snake venom proteasecomplex in the assay (as indicated by $R_2$ values in Table 7; graphs not shown).

Added $Ca^{2+}$ or $Ca^{2+}$ with $P_L$ did not substantially affect hydrolysis of S-2222 by Brown snake venom protease complex, which is similar for isolated Brown snake venom protease. A comparison of S-2222 hydrolysis by Brown snake venom protease complex with Brown snake venom protease shows that the rates in Units µg$^{-1}$ are similar. Since only about 10-15% of Brown snake venom protease complex is protease (on a mass basis), the rate of S-2222 hydrolysis by protease in the Brown snake venom protease complex in molar terms is about 10 times greater than for the isolated protease.

Citrated Plasma Clotting by Brown Snake Venom Protease Complex

Citrated plasma clotting assays were performed with Brown snake venom protease complex to compare clotting properties with isolated Brown snake venom protease. The results of these experiments are shown in Table 8. Values shown in Table 8 are derived from data in relation to clotting of citrated plasma by Brown snake venom protease complex with and without accessory components (i.e. Brown snake venom protease complex alone, Brown snake venom protease complex with 40 mM $CaCl_2$, and Brown snake venom protease complex with 40 mM $CaCl_2$ and phospholipid).

The results show that $Ca^{2+}$ and $P_L$ do not affect the clotting efficiency of Brown snake venom protease complex.

Effect of $Ca^{2+}$ on Citrated Plasma Clotting Time of Brown Snake Venom Serine Protease To investigate the clotting properties of Brown snake venom protease, citrated plasma clotting times without $Ca^{2+}$ were compared to that when $Ca^{2+}$ was present. The results in Tables 9 and 10 show that Brown snake venom protease complex does not require $Ca^{2+}$ to clot blood. For example, 39 µg/mL of isolated Brown snake venom serine protease will clot citrated plasma in the absence of $Ca^{2+}$ in less than 30 sec. Addition of $Ca^{2+}$ resulted in a 200 fold decrease in the amount of Brown snake venom protease required to give a clotting time of 70 sec (Table 10). This shows that Brown snake venom protease can convert prothrombin to thrombin in the absence of $Ca^{2+}$ and that $Ca^{2+}$ may facilitate prothrombin cleavage.

FIGS. 11A-11C show clotting of citrated plasma by Brown snake venom protease with and without accessory components (data points are means of duplicate measurements). FIG. 8A: Brown snake venom protease alone, FIG. 8B: Brown snake venom protease with 10 mM $CaCl_2$ and FIG. 8C: Brown snake venom protease with 10 mM $CaCl_2$ and phospholipid (platelin).

$Ca^{2+}$ would also enhance activation of fibrinogen by Brown snake venom protease produced thrombin (Mankad and Codispoti, 2001, Am J Surg 182 21S) and accordingly addition of $Ca^{2+}$ affecting clotting may be secondary to prothrombin activation. $P_L$ could also function to facilitate prothrombin cleavage by Brown snake venom protease, resulting in a further 10 fold decrease in the amount of Brown snake venom protease required for clotting, as shown in Table 14.

Effect of $Ca^{2+}$ on Cleavage of S-2222 Chromogenic Substrate by Prothrombin Activating Proteins To determine the Brown snake venom protease complex Factor Xa-like cleavage specificity, chromogenic assays using the Factor Xa specific chromogenic substrate S-2222 were performed. S-2222 is a synthetic chromogenic substrate developed for factor Xa (Aurell et al., 1977, Thrombin Res 11 595). Hydrolysis of S-2222 releases p-nitroaniline that is detectable by an increase in absorbance at 405 nm. Plots of enzyme activity versus amount of Brown snake venom protease were essentially linear, as shown in FIGS. 12A-12D. The results indicate that the rate of S-2222 hydrolysis was not affected by the presence of $Ca^{2+}$, or $Ca^{2+}$ and $P_L$, and therefore, that the catalytic site is not affected by $Ca^{2+}$ and $P_L$. From the slope of 0.002 U/µg protease, the specific activity of the purified preparation was 2 U/mg.

FIGS. 12A-12D show hydrolysis of S-2222 by Brown snake venom protease with and without accessory components (data points are means of duplicate measurements). FIG. 9A: Brown snake venom protease alone; FIG. 9B: Brown snake venom protease with 10 mM $CaCl_2$; FIG. 9C: Brown snake venom protease with 10 mM $CaCl_2$ and $P_L$. and FIG. 9D: slope and $R_2$ value of each plot shown in respective FIGS. 12A-12C. $R_2$ value is the correlation coefficient for a straight line.

Brown snake venom protease hydrolyses S-2222, with or without added $Ca^{2+}$ as shown in Table 11 albeit at slightly lower initial rates of hydrolysis without $Ca^{2+}$ compared to those in the presence of $Ca^{2+}$ In contrast, hydrolysis of a synthetic factor Xa substrate by Textarin was enhanced by the presence of $Ca^{2+}$ and $P_L$ (Stocker et al., 1994, Toxicon 32 1227), as was that by Trocarin, the factor Xa-like serine protease from Rough-scaled snake venom (Joseph et al., 1999, Blood 94 621).

Isolated Brown Snake Venom Protease Activation of Prothrombin

Not being bound by theory, it is believed that clotting occurs by a two-step reaction: (1) conversion of prothrombin to thrombin by Brown snake venom protease, followed by (2) cleavage of fibrinogen to fibrin and the activation of factor XIII by thrombin.

Referring to FIG. 10 which demonstrates Brown snake venom serine protease activation of prothromobin, within 10 minutes of reaction Brown snake venom protease acts to convert prothrombin to thrombin sufficiently to decrease citrated plasma clotting time from 65 seconds to a 12 second baseline.

Prothrombin Activation by Brown Snake Venom Protease

The results of the experiments below show that Brown snake venom protease is able to convert prothrombin to thrombin without $Ca^{2+}$, $P_L$ or accessory proteins like factor Va.

Results of the S-2222 assays indicate that Brown snake venom protease may hydrolyse the same bonds as factor Xa in prothrombin. An effect of Brown snake venom protease on prothrombin was determined using human prothrombin (0.5 mg in 2 mL 0.05 M Tris-HCl buffer) reacted with 5 μg Brown snake venom protease (1:100 enzyme: substrate). Reaction products were analysed by non-reducing SDS PAGE, as shown in FIG. 11A. Additionally, the rate of thrombin formation was monitored by S-2238 hydrolysis, as shown in FIG. 11B. S-2238 is commonly used for determining enzyme activity of thrombin (Komalik and Blomback, 1975, Nature 227 680), incorporated herein by reference.

FIG. 11A shows SDS PAGE of the time course of prothrombin cleavage by Brown snake venom protease. A protein band at ~40 kDa (lane 5) indicates that thrombin (molecular mass 36.7 kDa) is a major end product. This protein band increases in intensity with time showing that prothrombin (PT) is being converted by Brown snake venom protease to thrombin (T). The prothrombin is substantially gone by the 48 hour time point (lane 5). FIG. 11B shows initial activity against S-2238 was very low and increased approximately 20 fold. From the SDS PAGE gel, it would have been expected that S-2238 activity would have reached a maximum by 48 hours.

The human prothrombin used in these experiments was not totally pure, as indicated by bands shown in lane 2 of FIG. 11A. Only a prothrombin (PT) band at 72 kDa should be seen (Mann, 1976, Methods Enzymol 1976 132). A fainter protein band at ~55 kDa indicates the presence of some prethrombin 1 ($PT_1$), possibly resulting from cleavage of prothrombin by thrombin, as shown in FIG. 12. Prethrombin 1 is not an active enzyme, confirmed by the S-2238 assay on the prothrombin solution at t=0.

A prethrombin 1 band appears to have increased with time then decreased. Possibly thrombin was present in the prothrombin solution, but was not detectable by the S-2238 assay. More probably, thrombin generated during the incubation could have been responsible for the formation of prethrombin 1.

To assist with interpreting the results, a mechanism of prothrombin activation by Brown snake venom protease has been proposed and a schematic diagram is shown in FIG. 12. The invention is not bound by this diagram.

Isolated Brown Snake VenomA Protease Activation of Prothrombin and Formation of Cross-linked Fibrin From the above results, Brown snake venom protease activates prothrombin to thrombin. The activated thrombin should sequentially convert fibrinogen to fibrin. To investigate this, citrated plasma was incubated with Brown snake venom protease with or without $Ca^{2+}$. This resulted in formation of clots that were washed and then separated by SDS PAGE, along with a washed fibrin clot formed by the addition $Ca^{2+}$ alone to citrated plasma (representing formation of a normal in vivo clot since $Ca^{2+}$ alone activates the coagulation cascade. The results of this experiment, shown in FIG. 13, demonstrates that fibrin produced by the action of Brown snake venom protease has a similar structure to normal fibrin, formation of cross-linked fibrin occurs in response to Brown snake venom serine protease activation of thrombin and resultant Factor XIII activation. Approximate clotting times of each experiment were also recorded (Table 12).

Using the molecular weight standards (lane 1), and the chain structures of both fibrinogen (lane 5) and the $Ca^{2+}$ produced fibrin clot (lane 4) from FIG. 13, the bands can be identified. A band at about 100 kDa in lanes 2 and 3 (Brown snake venom protease without and with $Ca^{2+}$ respectively) is indicative of γ-dimer (γ-γ). γ-Dimer has a molecular mass of 105 kDa and results from covalent crosslinks made between two γ-monomers by factor XIIIa (McKee et al., 1970, Proc Natl Acad Sci 66 738).

Bands at approximately 70 and 60 kDa can also be seen in these lanes indicative of the α-monomer (α) and β-monomer (β) chains of fibrin respectively. α-Monomer has a molecular mass of 73 kDa, while β monomer has a molecular mass of 60 kDa (McKee et al., 1970, supra). The band with a molecular mass of greater than 400 kDa (top of gel) is indicative of α-polymer ($α_p$), resulting from lysine-glutamic acid covalent crosslinking of α-monomer by factor XIIIa (Gaffney and Brasher, 1974, Nature 251 53). The α-chain degradation product ($α_1$) can also be seen at ~38 kDa in lanes 2-4.

It appears that thrombin resulting from action of Brown snake venom protease converts fibrinogen to fibrin in a similar manner as normal α-thrombin. This is shown by comparing the banding patterns of the clot produced in the normal way (by addition of $Ca^{2+}$ to citrated plasma) with clots produced by Brown snake venom protease, with and without $Ca^{2+}$ (lanes 3 and 2 respectively). A larger amount of non-crosslinked α-monomer is present in the clot produced with Brown snake venom protease alone (lane 2) compared with in the presence of $Ca^{2+}$ (lane 3). This suggests that factor XIIIa was not as active in formation of the former clot. This is consistent with the literature since factor XIIIa activated in the presence of $Ca^{2+}$ is more active than the same enzyme activated in the absence of $Ca^{2+}$ (Turner and Maurer, 2002, Biochemistry 41 7947). Crosslinking of α-monomer by factor XIIIa is a slower process than γ-chain crosslinking, explaining why the γ-chain appears to be fully crosslinked in all three clots. Leaving the clot for longer than four hours may have allowed the α-monomer to be completely crosslinked.

Very similar banding patterns were observed in the clot produced using Brown snake venom protease with $Ca^{2+}$ and the clot representing normal in vivo formation ($Ca^{2+}$ alone). There was a difference however in the clotting times of these two clots (Table 12). The clot with Brown snake venom protease and $Ca^{2+}$ clotted ~30 times faster than the clot with $Ca^{2+}$ alone. This indicates that clotting was due to the action of Brown snake venom protease on citrated plasma rather than of the $Ca^{2+}$. Added calcium slightly decreased the clotting time of citrated plasma by Brown snake venom protease (120 to 60 sec). This is consistent with the results of citrated plasma clotting assays with Brown snake venom protease and added $Ca^{2+}$.

Structural Characterization of *P. Textilis*-Snake Venom Protease Active Site Labelling of Brown Snake Venom Protease Dansyl-L-glutamyl-glycyl-L-arginyl chloromethyl ketone (DNS-GGACK) is an inhibitor that specifically alkylates the active site histidine of serine proteases, including factor Xa, thereby inactivating them (Kettner and Shaw, 1981, Methods Enzymol 80 826). To determine which SDS PAGE band or bands comprises a catalytic site, Brown snake venom protease and intact Brown snake venom protease complex were respectively incubated with DNS-GGACK and separated run by SDS PAGE. Fluorescent properties of DNS-GGACK allows visualization of the Brown snake venom protease bands incorporating covalently bound inhibitor using ultraviolet light. The results of this experiment are shown in FIG. 14.

A prominent fluorescent band is visible in lane 3, corresponding to the intact Brown snake venom protease (lane 7). In the presence of β-mercaptoethanol (lane 4), the fluorescent inhibitor was exclusively incorporated into the heavy chain of the venom protease (band at approximately 37 kDa in lane 8). This shows that the active site of Brown snake venom protease is located on the heavy chain rather than the light chain. These results and also the location of Brown snake venom protease within the Brown snake venom protease complex banding pattern are confirmed in lanes 1 and 2, and 7 and 8.

The heavy chain of mammalian factor Xa comprises an enzyme active site (Bock et al., 1989, Arch Biochem Biophys 273 375). Analysis of peptide digests of factor Xa inactivated by DNS-GGACK has shown that histidine 42 of the heavy chain forms part of the active site. By sequence alignment, the active site histidine residues of both Trocarin and Brown snake venom protease are proposed to be in an identical position to the active site histidine of factor Xa, as shown in FIG. 15. The proposed histidine of the active site is shown in bold text.

N-terminal Amino Acid Sequencing of the Brown Snake Venom Serineprotease, and Sequence Homology with Factor Xa and *T. Carinatus* Factor Xa-like Serine Protease.

N-Terminal amino acid sequencing of the putative light and heavy chains of Brown snake venom protease was performed. Short sequences were also required to Facilitate cloning of the cdna for Brown snake venom protease from a *P. Textilis* Venom gland cdna library.

Brown snake venom protease complex and Brown snake venom protease were separated by SDS PAGE in the presence of β-mercaptoethanol and transferred to a PVDF membrane. From this membrane, sequencing of protein bands was performed.

Initially, partial amino acid sequence was obtained from the heavy chain of Brown snake venom protease: IVNGMD (C)KLGE [SEQ ID NO: 43]. Note that the (C) means that this cycle was blank and indicates that a cysteine was present but is not certain. The presence of this cysteine residue was subsequently confirmed after sequencing of a corresponding cDNA.

The heavy chain of Brown snake venom protease was a first protein band transferred to a PVDF membrane and sequenced. The N-terminus of the heavy chain fragment comprises an amino acid sequence: IVNGMDCKLGE [SEQ ID NO: 43]. A homology search showed that this sequence is 100% identical with the N-terminal sequence of the heavy chain of Trocarin (see FIG. 16). This sequence was used to design a nucleic acid primer that was used successfully to amplify Brown snake venom protease cDNA. Similarity was also found between the N-terminal sequence of Brown snake venom protease and human factor Xa heavy chain, shown in FIG. 17.

The light chain of Brown snake venom protease was also amino acid sequenced. The N-terminal sequence from the band corresponding to the light chain was ANSLVXXFKS-GNI [SEQ ID NO: 44]. The "X" indicate that there were blanks in the 6$^{th}$ and 7$^{th}$ sequencing cycles. This indicated that the amino acids were either cysteines, which degrade during sequencing, or that the residues contained post-translational modifications. The amino acid sequence of Brown snake venom protease deduced from a nucleotide sequence of the corresponding cDNA revealed that the "X" amino acid residues were both glutamic acid. The "X" in the amino acid sequence were substituted for these residues. Homology of the sequenced N-terminus of the light chain of the invention was aligned with Trocarin as shown in FIG. 18. Similarity was also found by aligning the partial Brown snake venom light chain sequence with the N-terminal sequence of mouse factor Xa light chain as shown in FIG. 19. The alignments shown in FIGS. 18-23 show that Brown snake venom protease shares homology with Trocarin, and factor Xa.

Sequence homology was also found with another second sequence for Brown snake venom serine protease and Factor Xa. Homology is greater than 55%.

A comparison between trocarin amino acid sequence and N-terminal sequence obtained from Brown snake venom serine protease.

The full length cDNA and encoded protein sequence of Brown snake venom serine protease was obtained as described above and both sequences are shown in FIGS. 25-28.

A comparison of the complete amino acid sequence of Brown snake venom serine protease and trocarin is shown in FIGS. 26 and 27. The overall level of sequence identity was 81%, however there are a number of unique features in Brown snake venom protease beginning at the N-terminal propeptide sequence (40 amino acids) which is not present in trocarin. It was predicted that the propeptide cleavage site to be between R and A at the end of the propeptide as shown in FIG. 29. This is supported by a BLAST search which reveals a series of haemostatic factors including factors X, IX, VII and others and their precursors as being related to Brown snake venom serine protease. This sequence at the end of the propeptide KRANS - - - EE - - - EREC [SEQ ID NO: 48] and additional glutamic acid residues important for function in binding Ca$^{2+}$ are well conserved. Indeed there are several blocks of sequence conserved including the cleavage site or parts of it between the heavy and light chains RIVNGMD [SEQ ID NO:45]just distal to amino acid residue 200.

Another difference with trocarin evident in the alignment is the presence of 28 amino acids in Brown snake venom protease (residues 182-209) which are absent in trocarin. This sequence leads up the predicted cleavage site between light and heavy chains as shown in FIGS. 21A and 21B. The light chain of Trocarin consists of 141 residues and ends with the amino acid sequence KARNK [SEQ ID NO: 46] (Joseph et al., 1999, Blood 94 621). The predicted amino acid sequence of Brown snake venom protease light chain comprises a similar sequence (KTRNK) [SEQ ID NO: 47] starting at amino acid 176 of FIG. 29. The light chain of Brown snake venom protease may be cleaved at this point thereby removing the final 28 amino acids before the start of the heavy chain. The molecular mass of Brown snake venom protease was calculated to be 43,587 Da, assuming cleavage at the above indicated point, and respective heavy and light chains are predicted to have a molecular mass of 27,952 and 15,652 Da (see Table 13).

Distance migrated of proteins separated by SDS PAGE was also used to estimate the molecular mass of Brown snake venom protease and its component chains (data not shown). Approximate molecular masses of the intact Brown snake venom protease and its heavy and lights chains were determined to be 53 kDa, 35 kDa and 29 kDa respectively based on SDS PAGE data (see Table 13).

The cDNA nucleotide sequence does not indicate whether a protein is cleaved or if it has post-translational modifications. For this reason, Trocarin was used as a model since the amino acid sequence of native Trocarin (determined by protein sequencing) and the translated cDNA nucleotide sequence of Brown snake venom protease are very similar. The molecular mass of native Trocarin was estimated to be 46,515 Da (Joseph et al., 1999, supra). The molecular mass calculated from the Trocarin amino acid sequence without any post-translational modifications is about 42,455 Da. Accordingly, there is approximately 4,060 Da of post-translational modifications including Glu residues, N-glycosylation and O-glycosylation. Trocarin and Brown snake venom protease are very similar and therefore it may be predicted that Brown snake venom protease will have a similar post-translational modification as trocarin. Based on this assumption, the molecular mass of Brown snake venom protease with post-translational modifications and a cleaved light chain is 47,647 Da, which is consistent with the experimentally determined value of 53 and 48 kDa. Factor Xa has a molecular mass of 46 kDa (Di Scipio et al., 1977, Biochemistry 67 99). This calculated mass of 47,647 Da was used in determining the concentration of Brown snake venom protease in solution.

Comparison of Snake Derived Venom Protease Proteins

The venom glands from a coastal taipan, inland taipan, brown, tiger, red-belly black and rough scale snake were removed from alive road damaged specimens, and total RNA extracted via the TRI Reagent© method for RNA extraction (Sigma, Castle Hill, Australia). First-strand cDNA was then synthesised from the RNA. The cDNA was then screened for the factor Xa-like snake venom protease gene via PCR using degenerate primers designed from the preliminary amino acid sequence deduced from the brown snake protease. Note that different regions of the protease were amplified, using different primer sets, with focus upon the heavy chain of the factor Xa-like component. All PCR products were run on a 1.5% TAE agarose gel, extracted using a QIAEX II gel extraction kit (Qiagen, Hilden, Germany), cloned into the pGEM-T vector system (Promega, Annandale, Australia) and subsequently sequenced using an ABI Prism Big Dye Terminator Cycle Sequence Ready Reaction Kit (Perkin-Elmer, Boston, U.S.A.). Sequence alignments were then performed between the proteases isolated from the all five species. FIG. 27 shows an amino acid alignment of the brown, coastal taipan, red belly black, tiger and rough scale snake proteases of the invention with trocarin. FIG. 28 shows an amino acid alignment of these proteases of the invention with human factor Xa. FIG. 29 shows an alignment of all of the brown, coastal taipan, inland taipan, red belly black, tiger and rough scale snake proteases of the invention with propeptide, light chain and heavy chain domains indicated.

Cloning and Sequencing of Nucleic Acids Encoding Taipan, Tiger, Rough Scale and Red-belly Black Snake Venom Protease Proteins Respective full length nucleic acids encoding snake venom protease proteins were cloned and sequenced from taipan, tiger, rough scale and red-belly black snakes. An alignment of the nucleotide sequences of the above snake derived nucleic acids with the snake venom protease from the common brown snake revealed a number of points of interest. This includes almost 100% homology within a 40 amino acid propeptide amino acid sequence (residues 1-40 shown in FIGS. 29 and 30), not withstanding a single amino acid change within the red-belly black snake. This high degree of conservation is also observed within the regions of the cleavage site between the propeptide and the light chain, and the light chain and the heavy chain (see FIG. 29). Overall there is a 72% degree of homology between the five snakes. The protease from the taipan is most closely related to that of the common brown snake, being 92% homologous, as would be expected as both are group C prothrombin activators. Likewise, there is a high degree of similarity between the group D prothrombin activators from the mainland tiger and rough scale snakes with 95% homology, with the red-belly black snake protease being the most distinct of the five. One final point of interest is the area of low homology within the heavy chain, where deletions are observed within the tiger, red-belly black and rough scale snakes, plus the premature termination of the protease eleven amino acids from the end in the tiger and rough scale snakes.

There are conserved novel regions of the snake venom proteases that are distinct from both trocarin and human factor Xa and all other known proteins. These regions include the following, which are also shown in FIGS. 27-29 as consensus sequences.

KREASLPDFVQS (residues 181-192) SEQ ID NO: 19];
LKKSDNPSPDIR (residues 198-209) [SEQ ID NO: 20]; and
SVX$_1$VGEIX$_2$X$_3$SR (residues 260-270) [SEQ ID NO: 21]
X$_1$, X$_2$ and X$_3$ may be any amino acid, but preferably X$_1$ is either V or I, X$_2$ is either D or N and X$_3$ is either R or I.
MAPQLLLCLILTFLWSLPEAESNVFLKSK (residues 1-29) [SEQ ID NO:22] and
ANRFLQRTKR (residues 31-40) [SEQ ID NO: 23]
KREASLPDFVQSXXAXXLKKSDNPSPDIR (residues 181-209) [SEQ ID NO: 24], wherein X may be any amino acid
MAPQLLLCLILTFLWSLPEAESNVFLK-SKXANRFLQRTKR (residues 1-40) [SEQ ID NO: 25], wherein X may be any amino acid It will be appreciated that SEQ ID NOS: 23, 24 and 25 correspond to a predicted propeptide comprising amino acids 1-40 as shown in FIG. 29 and accordingly may not in one embodiment form part of a proteolytically digested mature protein.

A person skilled in the art will be able to identify other novel conserved regions of the prothrombin activating proteins of the invention based on alignment data provided in FIGS. 27-29.

Similarly, novel conserved nucleic acids encoding the prothrombin activating proteins of the invention may be determined from alignment data provide in FIG. 30. Such novel nucleic acids may be useful, for example, in designing specific nucleic acid primers and/or probes to amplify, sequence and/or identify a nucleic acid of the invention.

Fibrin Glue

Citrated plasma with added Brown snake venom scrine protease clotted very quickly in the both the presence and absence of 10 mM Ca$^{2+}$. The macroscopic texture of the two clots appears to differ for the two preparations.

Mouse Tail-Vein Bleeding Model

Effectiveness of purified Brown snake venom protease functioning as an anti-bleeding agent was tested in mice using a tail-vein bleeding model. The results of these experiments are shown in Tables 14 and 15 and FIGS. 32-33.

Mouse tail-vein bleeding studies were performed as essentially described by Masci et al (2000) with minor alteration. The results are shown in FIGS. 32 and 33 and Tables 14 and 15. *P. textilis* protease (250 μL; 65 μg/mL *P. textilis* protease in 0.02 M Tris-HCl, pH 7.4, 10 mM CaCl$_2$) was applied topically to the open wound of the severed tail for 3 minutes. Blood loss was measured using preweighed eppendorf tubes. Accuracy dictated that blood loss was measured by weight rather than volume. It is noted that all mice topically treated with the protease showed a large clot at the site of injury as shown in FIG. 27. Mice were euthanized via cervical dislocation.

Data for Table 15 and FIG. 28 were obtained from experiments wherein an open wound of a severed mouse tail was submersed in 250 μl 0.9% sodium chloride (saline control) with or without 65 μg Brown snake venom protease for three minutes. Blood lose was measured by weight. As Table 15 and FIG. 28 show, cofactors are not required to clot blood.

As shown in Tables 14 and 15 and FIG. 28, Brown snake venom protease significantly reduced blood loss in mice (0.169 g±0.086) compared to the control animals (0.542±0.160) (Mann Whitney U test, p=0.021) when corrected for technical errors.

EXAMPLE

Generation of a cDNA library from the venom gland of Taipan to establish a microarray chip for cross-species comparisons and use for drug discovery.

Messenger RNA extracted from the venom gland of the target snake was amplified as cDNA and fragments greater then 600 bp in size cloned into a λTrip1Ex2 vector using a SMART cDNA library synthesis kit (Clontech, Palo Alto, U.S.A.). Such a cDNA library was produced from both the taipan and brown snake, and preliminary sequence analysis performed on approximately 30 transcripts from each library. This process involved PCR amplification to detect the presence and size of the insert, followed by conversion of the λTrip1Ex2 to a pTrip1Ex2 plasmid and subsequent sequencing.

Due to its average increased insert size and variation, it was decided to select the taipan cDNA library for the establishment of a microarray chip. Subsequently, 4800 cDNA clones were randomly isolated for large scale PCR amplification and purification, which were then spotted in duplicate onto coated glass slides using an GMS 417 array spotter available within the Queensland Institute of Medical Research. RNA from the venom glands of the afore mentioned snakes was then amplified in a linear fashion using a modified Eberwine antisense RNA amplification protocol (yielding up to a seventy fold increase in RNA concentration) awaiting hybridisation to the chip.

Discussion

The snake venom proteases of the invention have a unique structure and functional properties. They also share some similarities with Factor Xa and the *O. scutellatus*-prothrombin activator. The snake venom proteases of the invention clot citrated plasma without the presence of $Ca^{2+}$. In vivo, Factor Xa also requires the presence of $Ca^{2+}$ for normal clotting. Accordingly, it is a novel and surprising observation that the snake venom proteases of the invention are capable of clotting blood without the presence of factors such as phospholipid, factor Va or $Ca^{2+}$.

The Factor Xa specific chromogenic substrate, S-2222 is cleaved by the snake venom proteases of the invention. This shows that the snake venom proteases have very similar cleavage specificity to Factor Xa. Furthermore, it is interesting that $Ca^{2+}$ only enhances the rate of S-2222 hydrolysis at concentrations lower than 2 μg/ml of Brown snake venom protease complex. Also, when NaSCN is added to the Brown snake venom protease complex, not all of the S-2222 activity is maintained. These observations are distinct from the work by Speijer et al (1986) in relation to the *O. scutellatus*-prothrombin activator.

The simple gel filtration method using Sephacryl S-300 proved relatively poor for the isolation of the serine protease component from the Brown snake venom protease complex, evident from the number of chromatographies required for purification. Despite the extended purification, a homogenous preparation was finally achieved, determined by HPLC and SDS PAGE in the absence of β-Me.

The SDS PAGE results suggest that the Brown snake venom protease has a native molecular weight of between 55 and 56 kDa. The Brown snake venom protease shares greater size similarity with the 54 kDa mammalian Factor Xa (Mann et al, 1987) than the 60 kDa *O. scutellatus* Factor Xa-like protease (Speijer et al, 1987, J. Biol. Chem. 261 13258). Furthermore, the Brown snake venom protease chain structure shows greater resemblance to Factor Xa than the *O. scutellatus* Factor Xa-like serine protease.

SDS PAGE (+β-Me) showed that the Brown snake venom protease comprises two peptide chains, probably linked together by a disulfide bridge. This is further supported by the finding of two N-terminus amino acids from sequencing of the Brown snake venom protease. From the results, the sizes of the heavy and light chains are approximately 31 and 18 kDa respectively, however this does not correspond with a total protease molecular weight of 55-56 kDa. In contrast to the Brown snake venom protease of the invention, the *O. scutellatus* Factor Xa-like serine protease was found to consist of two chains composed of 30 kDa each (Speijer et al, 1986, supra).

It was an interesting observation that 100% sequence homology exists between the first 11 amino acids of the *T. carinatus* Factor Xa-like serine protease and the Brown snake venom proteases of the invention. This shows that a degree of amino acid sequence (revealed with the complete amino acid sequence of the Brown snake venom protease) conservation has occurred throughout the evolution of these two Australian snake venom prothrombin activators. Sequence homology also exists between Factor Xa and the Brown snake venom protease, showing that some amino acids have been conserved in the evolution of snakes and mammals. However, as also shown in FIGS. 27 and 28, the snake venom proteases of the invention have novel conserved regions that are distinct from Factor Xa and Trocarin and all other proteins known to the applicant.

Factor Xa has all the typical characteristics of a serine protease, having two similarly structured domains, intradomain disulfide bonds and others (Stubbs & Bode, 1994, supra). However, serine proteases differences confer their specific function. For example, the Factor Xa active site cleft is much more open than the thrombin cleft (Stubbs & Bode, 1994, supra), which may contribute to the Factor Xa cleavage specificity for Arg274-Thr275 and Arg323-Ile324.

A novel therapeutic use for the snake venom proteases of the invention is as reagents for making topical fibrin glue. The snake venom proteases of the invention may provide a more effective therapeutic for preparing fibrin glue than current methods. Topical fibrin glue prepared with the snake venom proteases of the invention may greatly reduce haemorrhage experienced in trauma and hence could possibly save many human and non-human animal lives. For example, emergency medical units may be equipped with bandages and the like impregnated with a fibrin glue comprising snake venom proteases of the invention to prevent bleeding at an accident.

Abbreviations

A405—absorbance at 405 nm
Arg—arginine
AUFS—absorbance units full scale at 280 nm
C—cysteine
$Ca^{2+}$—calcium ions
$CaCl_2$—calcium chloride
cm—centimeter
D—aspartic acid
E—glutamic acid
F—phenylalanine
G—glycine
HPLC—high performance liquid chromatography
hr—hour I—isoleucine
Ile—isoleucine
K—lysine
kDa—kilo Dalton
L—leucine
M—methionine
M—molar
mg—milligram
min—minute
ml—milli liter
mM—mill molar
N—asparagines
NaSCN—sodium thiocyanate
nm—nano meter
*O. scutellatus*—*Oxyuranus scutellatus*
*P. textilis*—*Pseudonaja textilis*
PAGE—polyacrylamide gel electrophoresis
PEG—polyethylene glycol
Q—glutamine
S—serine
SDS—sodium dodecyl sulfate
sec—second
T—threonine
*T. carinatus*—*Tropidechis carinatus*
TFA—trifluoroacetic acid
Thr—threonine
TOF—time of flight
V—valine
Y—tyrosine
β-Me—β-mercaptoethanol
μl—micro liter
μmol—micro molar

TABLE 1

| Step | Sample volume (mL) | Total A280 | Total Activity (Units) | Specific Activity (Units/mL/A280) | Yield (%) | Purification |
|---|---|---|---|---|---|---|
| Brown SVP Complex with NaSCN | 20.0 | 80.0 | 106.5 | 1.3 | 100 | – |
| Step 1 | 15.0 | 25.7 | 51.2 | 2.0 | 48.1 | 1.5 |
| Step 2 | 8.0 | 13.0 | 27.3 | 2.1 | 25.6 | 1.6 |
| Step 3 | 5.5 | 7.3 | 17.2 | 2.4 | 16.1 | 1.8 |

TABLE 2

| STEP | SAMPLE VOLUME (mL) | TOTAL $A_{280}$ | TOTAL ACTIVITY (Units) | SPECIFIC ACTIVITY (Units/mL/$A_{280}$) | YIELD (%) | PURIFICATION |
|---|---|---|---|---|---|---|
| Brown SVP Complex with NaSCN | 18.0 | 50.4 | 40.1 | 0.8 | 100 | — |
| Step 1 | 5.0 | 13.0 | 13.1 | 1.0 | 32.6 | 1.2 |
| Step 2 | 3.5 | 10.4 | 10.9 | 1.1 | 27.2 | 1.3 |

TABLE 3

| STEP | SAMPLE VOLUME (mL) | TOTAL $A_{280}$ | TOTAL ACTIVITY (Units) | SPECIFIC ACTIVITY (Units/mL/$A_{280}$) | YIELD (%) | PURIFICATION |
|---|---|---|---|---|---|---|
| Brown SVP Complex + NaSCN | 10.0 | 89.0 | 32.5 | 0.4 | 100 | — |
| Superdex 200 (step 1) | 20.0 | 7.0 | 9.2 | 1.3 | 28.3 | 3.25 |
| Superdex 200 (step 2) | 40 | 3.0 | 4.4 | 1.5 | 13.5 | 3.75 |

TABLE 4

| STEP | SAMPLE VOLUME (mL) | TOTAL $A_{280}$ | TOTAL ACTIVITY (Units) | SPECIFIC ACTIVITY (Units/mL/$A_{280}$) | YIELD (%) | PURIFICATION |
|---|---|---|---|---|---|---|
| Brown SVP Complex | 32.0 | 38.4 | 501.2 | 13.1 | 100 | — |
| Superdex 200 (step 1) | 9.0 | 17.1 | 231.3 | 13.5 | 46.1 | 1.0 |
| Superdex 200 (step 2) | 9.5 | 16.2 | 168.2 | 10.4 | 33.6 | 0.8 |

TABLE 5

| STEP | SAMPLE VOLUME (mL) | TOTAL $A_{280}$ | TOTAL ACTIVITY (Units) | SPECIFIC ACTIVITY (Units/mL/$A_{280}$) | YIELD (%) | PURIFICATION |
|---|---|---|---|---|---|---|
| Venom | 25.0 | 700 | 2087 | 2.97 | 100 | — |
| ConA 4B | 640.0 | 379.0 | 97.3 | 0.257 | 4.6 | 0.09 |
| CM-Sepharose | 17.5 | 79.0 | 25.0 | 0.32 | 1.2 | 0.12 |
| Superdex 200 | 7.5 | 2.5 | 1 | 0.442 | 0.05 | 0.15 |

TABLE 6

| STEP | SAMPLE VOLUME (mL) | TOTAL $A_{280}$ | TOTAL ACTIVITY (Units) | SPECIFIC ACTIVITY (Units/mL/$A_{280}$) | YIELD (%) | PURIFICATION |
|---|---|---|---|---|---|---|
| Brown SVP Complex | 22.0 | 20.9 | 110 | 5.3 | 100 | — |
| Phenyl-Sepharose | 10 | 4.85 | 14 | 2.9 | 12.7 | 0.55 |
| Superdex 200 | 3.5 | 1.14 | 6.4 | 5.6 | 5.8 | 1.1 |

TABLE 7

| CONDITION | SLOPE | $R_2$ |
|---|---|---|
| A-Brown SVP complex alone | 0.0022 | 0.9965 |
| B Brown SVP complex w/ 10 mM $CaCl_2$ | 0.0025 | 0.9884 |
| C Brown SVP complex w/ 10 mM $CaCl_{2+}$ phospholipid. | 0.0041 | 0.9852 |

TABLE 8

| CLOTTING TIME (sec) | B SVP COMPLEX (µg) ± ACCESSORY COMPONENTS | | |
|---|---|---|---|
| | Alone | $Ca^{2+}$ | $Ca^{2+}$ and $P_L$ |
| 20 | 0.5 | 0.5 | 0.6 |
| 10 | 2.5 | 3 | 3 |

TABLE 9

| Brown SVP (µg/mL | Clotting time (sec) $-Ca^{2+}$ | Clotting time (sec) $+Ca^{2+}$ |
|---|---|---|
| 39.000 | 27.3 | 14.9 |
| 26.000 | 35.1 | 18.7 |
| 13.000 | 38.4 | 23.4 |
| 6.500 | 51.6 | 24.0 |
| 2.600 | >100 | 27.6 |
| 1.300 | >100 | 34.5 |
| 0.650 | >100 | 34.7 |

TABLE 10

| CLOTTING TIME (sec) | BROWN SVP (µg) ± ACCESSORY COMPONENTS | | |
|---|---|---|---|
| | Alone | $Ca^{2+}$ | $Ca^{2+}$ and $P_L$ |
| 70 | 4 | 0.02 | 0.002 |
| 50 | 11 | 0.05 | 0.004 |

TABLE 11

| Brown SVP (µg/mL) | $\Delta A_{405/min}$ $-Ca^{2+}$ | $\Delta A_{405/min}$ $+Ca^{2+}$ |
|---|---|---|
| 39 | 0.70 | 1.11 |
| 19.5 | 0.33 | 0.90 |
| 13 | 0.26 | 0.36 |
| 6.5 | 0.15 | 0.24 |
| 2.6 | 0.12 | 0.11 |
| 1.3 | 0.06 | 0.09 |
| 0.65 | 0.03 | 0.05 |
| 0.33 | 0.01 | 0.01 |

TABLE 12

| CLOT TYPE | TIME (SEC) |
|---|---|
| Brown SVP | 120 |
| Brown SVP with 40 mM $CaCl_2$ | 60 |
| $CaCl_2$ alone | 1800 |

TABLE 13

| METHOD OF MASS DETERMINATION | MOLECULAR MASS (DA) | | |
|---|---|---|---|
| | Heavy chain | Light chain | Intact protein |
| SDS PAGE | 35000 | 29000 | 53000 |
| Mass spectrometry | — | — | 48000 |
| Calculated from cDNA sequence without propeptide (residues 1–40) | 27952 | 18789 | 46723 |
| Calculated from cDNA sequence without propeptide and assuming light chain has 141 residues as does that of Trocarin | 27952 | 15652 | 43587 |
| Calculated from cDNA sequence without propeptide, 141 residue light chain, Gla residues and glycosylation at the same level as Trocarin | — | — | 47647 |

TABLE 14

| Treatment | Blood loss (grams) (n = 2) | Relative blood conserved (%) |
|---|---|---|
| Saline | 0.4335 | — |
| Protease/10 mM Ca$^{2+}$ | 0.0166 | 96.17 |

TABLE 15

| TEST | BLOOD LOSS (g) | CONTROL | BLOOD LOSS (g) |
|---|---|---|---|
| 1 | 0.12 | 1 | 0.64 |
| 2 | 0.16 | 2 | 0.71 |
| 3 | 0.29 | 3 | 0.42 |
| 4 | 0.10 | 5 | 0.39 |
| Average blood loss (g) ± SD | 0.169 g ± 0.086 | Average blood loss (g) ± SD | 0.542 ± 0.160 |

TABLE 16

| Snake venoms | Venom concentration (mg/mL) | Clotting times (sec ± 0.5 secs) |
|---|---|---|
| A | | |
| *Pseudonaja textilis*- Qld | 2.0 | 3.9 |
| *Pseudonaja textilis*- SA | 2.0 | 5.4 |
| *Pseudonaja textilis*- Goyder lagoon | 2.0 | 8.4 |
| *Pseudonaja nuchalis* | 2.0 | 8.7 |
| *Pseudonaja affinis* | 2.0 | 5.5 |
| *Pseudonaja inframacula* | 2.0 | 7.9 |
| *Oxyuranus scutellatus* | 200.0 | 24.1 |
| *Oxyuranus microlepidotus* | 500.0 | 19.7 |
| *Notechis scutatus* | 500.0 | 34.9 |
| *Notechis ater niger* | 500.0 | 27.7 |
| *Notechis ater serventyi* | 1,000.0 | 31.1 |
| *Hoplocephalus stephansii* | 1,000.0 | 36.2 |
| *Pseudechis porphiracus* | 500.0 | 48.6 |
| *Australaps surperba* | 1,000.0 | 38.7 |
| *Tropedechis carinatus* | 500.0 | 34.9 |
| B | | |
| *Australaps ramsayii* | 1,000.0 | 250>clot<600 |
| *Pseudechis guttatus* | 1,000.0 | 250>clot<600 |
| *Pseudechis australis* | 1,000.0 | >100; no clot |
| *Pseudechis colletti* | 1,000.0 | >100; no clot |
| *Acanthopis antarcticus* | 1000.0 | >100; no clot |
| *Cryptophis nigrescens* | 1,000.0 | >100; no clot |
| C | | |
| *Bothrops jararaca* | 100.0 | 11.7 |
| *Agkistradom rhodasroma* | 100.0 | 6.3 |
| *Vipera russelli* | 500.0 | >200 |
| *Naja naja* | 500.0 | >200 |
| *Naja naja miolepis* | 500 | >200 |
| *Echis carinatus* | 200.0 | 10.4 |
| *Bothrops atrox* | 100.0 | 5.3 |
| *Bungarus fasciatus* | 50.0 | 12.6 |
| *Ophiophagus hannah* | 100.0 | >200; weak clot |

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

---

SEQUENCE LISTING

<160> NUMBER OF SEQ ID NOS: 61

<210> SEQ ID NO 1
<211> LENGTH: 1404
<212> TYPE: DNA
<213> ORGANISM: Psuedonaja textilis
<220> FEATURE:
<221> NAME/KEY: CDS
<222> LOCATION: (1)..(1401)

<400> SEQUENCE: 1

```
atg gct cct caa cta ctc ctc tgt ctg atc ctc act ttt ctg tgg agt        48
Met Ala Pro Gln Leu Leu Leu Cys Leu Ile Leu Thr Phe Leu Trp Ser
1               5                   10                  15 ctc cca gag gct gaa agt aat gta ttc tta aaa agc aaa gtg gca aat        96
Leu Pro Glu Ala Glu Ser Asn Val Phe Leu Lys Ser Lys Val Ala Asn
            20                  25                  30 aga ttt ttg caa aga aca aaa cga gct aat tca ctg gtt gag gaa ttt       144
Arg Phe Leu Gln Arg Thr Lys Arg Ala Asn Ser Leu Val Glu Glu Phe
        35                  40                  45 aaa tct gga aac att gaa agg gaa tgc att gag gag aga tgt tca aaa       192
Lys Ser Gly Asn Ile Glu Arg Glu Cys Ile Glu Glu Arg Cys Ser Lys
    50                  55                  60 gaa gaa gcc agg gag gta ttt gaa gat gac gag aaa act gag acc ttc       240
Glu Glu Ala Arg Glu Val Phe Glu Asp Asp Glu Lys Thr Glu Thr Phe
65                  70                  75                  80
```

| | | |
|---|---|---|
| tgg aat gtt tat gta gat ggg gat cag tgt tca tca aac ccc tgt cat<br>Trp Asn Val Tyr Val Asp Gly Asp Gln Cys Ser Ser Asn Pro Cys His<br>                                   85                          90                          95 | 288 |

```
tgg aat gtt tat gta gat ggg gat cag tgt tca tca aac ccc tgt cat      288
Trp Asn Val Tyr Val Asp Gly Asp Gln Cys Ser Ser Asn Pro Cys His
             85                  90                  95 tat cgc ggg ata tgc aaa gat ggc att ggt agc tat acc tgt acc tgc      336
Tyr Arg Gly Ile Cys Lys Asp Gly Ile Gly Ser Tyr Thr Cys Thr Cys
            100                 105                 110 ttg tct ggc tat gaa ggg aaa aac tgt gaa cgt gtc tta tat aag tcc      384
Leu Ser Gly Tyr Glu Gly Lys Asn Cys Glu Arg Val Leu Tyr Lys Ser
        115                 120                 125 tgc aga gtg gac aat ggt aac tgt tgg cac ttc tgc aaa tct gtt caa      432
Cys Arg Val Asp Asn Gly Asn Cys Trp His Phe Cys Lys Ser Val Gln
    130                 135                 140 aac gat att caa tgt tca tgc gct gaa ggt tac ctt ttg gga gag gat      480
Asn Asp Ile Gln Cys Ser Cys Ala Glu Gly Tyr Leu Leu Gly Glu Asp
145                 150                 155                 160 ggg cac tct tgt gtt gct gga ggt aac ttt tca tgt ggt aga aat atc      528
Gly His Ser Cys Val Ala Gly Gly Asn Phe Ser Cys Gly Arg Asn Ile
                165                 170                 175 aaa aca agg aac aag agg gaa gca agt ctg cct gac ttt gtg cag tcc      576
Lys Thr Arg Asn Lys Arg Glu Ala Ser Leu Pro Asp Phe Val Gln Ser
            180                 185                 190 cat aat gca act ttg ctg aaa aaa tct gat aat cca agc cct gat atc      624
His Asn Ala Thr Leu Leu Lys Lys Ser Asp Asn Pro Ser Pro Asp Ile
        195                 200                 205 aga att gtt aac gga atg gac tgc aaa ctg ggt gaa tgt ccg tgg cag      672
Arg Ile Val Asn Gly Met Asp Cys Lys Leu Gly Glu Cys Pro Trp Gln
    210                 215                 220 gca gct ctg gta gat gac aag aaa ggt gtg ttt tgt gga gga aca att      720
Ala Ala Leu Val Asp Asp Lys Lys Gly Val Phe Cys Gly Gly Thr Ile
225                 230                 235                 240 ttg agt ccc atc tat gtg ctt act gca gcc cac tgc att aat gag acc      768
Leu Ser Pro Ile Tyr Val Leu Thr Ala Ala His Cys Ile Asn Glu Thr
                245                 250                 255 gag acg att tca gtt gtt gta gga gaa ata gac aga tca aga gca gaa      816
Glu Thr Ile Ser Val Val Val Gly Glu Ile Asp Arg Ser Arg Ala Glu
            260                 265                 270 acc gga cct ctt ctt tct gtg gat aaa gta tat gtg cat aaa aaa ttt      864
Thr Gly Pro Leu Leu Ser Val Asp Lys Val Tyr Val His Lys Lys Phe
        275                 280                 285 gtt cct ccc aaa aaa agc cag gaa ttc tat gaa aag ttt gat ctt gtc      912
Val Pro Pro Lys Lys Ser Gln Glu Phe Tyr Glu Lys Phe Asp Leu Val
    290                 295                 300 agc tat gac tat gat ata gcc atc atc caa atg aag acc cct atc cag      960
Ser Tyr Asp Tyr Asp Ile Ala Ile Ile Gln Met Lys Thr Pro Ile Gln
305                 310                 315                 320 ttc tct gaa aat gtg gtt cct gcc tgc ctt ccc aca gct gat ttt gcc     1008
Phe Ser Glu Asn Val Val Pro Ala Cys Leu Pro Thr Ala Asp Phe Ala
                325                 330                 335 aac caa gtc ctc atg aaa caa gat ttt ggc atc gtt agt gga ttt ggg     1056
Asn Gln Val Leu Met Lys Gln Asp Phe Gly Ile Val Ser Gly Phe Gly
            340                 345                 350 ggt att ttc gaa aga gga ccg aac tct aaa aca ctt aaa gtc ctt aag     1104
Gly Ile Phe Glu Arg Gly Pro Asn Ser Lys Thr Leu Lys Val Leu Lys
        355                 360                 365 gtt cct tat gtg gac agg cac acc tgc atg ctt tcc agc aat ttt cca     1152
Val Pro Tyr Val Asp Arg His Thr Cys Met Leu Ser Ser Asn Phe Pro
    370                 375                 380 att act cca act atg ttc tgt gct ggc tat gat act ctg cct caa gat     1200
Ile Thr Pro Thr Met Phe Cys Ala Gly Tyr Asp Thr Leu Pro Gln Asp
```

-continued

```
                385                 390                 395                 400
gca tgc caa gga gac agc ggg ggg ccc cac atc act gca tac aga gat        1248
Ala Cys Gln Gly Asp Ser Gly Gly Pro His Ile Thr Ala Tyr Arg Asp
                405                 410                 415 acc cac ttt att act ggg att gtc agc tgg ggg gaa gga tgt gca cgg        1296
Thr His Phe Ile Thr Gly Ile Val Ser Trp Gly Glu Gly Cys Ala Arg
                420                 425                 430 aaa ggc aga tat ggt att tac aca aaa ttg tcc aaa ttc atc cct tgg        1344
Lys Gly Arg Tyr Gly Ile Tyr Thr Lys Leu Ser Lys Phe Ile Pro Trp
                435                 440                 445 ata aaa aga ata atg cgt caa aag cta ccc agt aca gag tca agc act        1392
Ile Lys Arg Ile Met Arg Gln Lys Leu Pro Ser Thr Glu Ser Ser Thr
450                 455                 460 ggt cgg ctc taa                                                        1404
Gly Arg Leu
465
```

<210> SEQ ID NO 2
<211> LENGTH: 467
<212> TYPE: PRT
<213> ORGANISM: Psuedonaja textilis

<400> SEQUENCE: 2

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ala Asn Ser Leu Val Glu Glu Phe
            35                  40                  45

Lys Ser Gly Asn Ile Glu Arg Glu Cys Ile Glu Glu Arg Cys Ser Lys
        50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Ile Cys Lys Asp Gly Ile Gly Ser Tyr Thr Cys Thr Cys
                100                 105                 110

Leu Ser Gly Tyr Glu Gly Lys Asn Cys Glu Arg Val Leu Tyr Lys Ser
            115                 120                 125

Cys Arg Val Asp Asn Gly Asn Cys Trp His Phe Cys Lys Ser Val Gln
        130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
                180                 185                 190

His Asn Ala Thr Leu Leu Lys Lys Ser Asp Asn Pro Ser Pro Asp Ile
            195                 200                 205

Arg Ile Val Asn Gly Met Asp Cys Lys Leu Gly Glu Cys Pro Trp Gln
        210                 215                 220

Ala Ala Leu Val Asp Asp Lys Lys Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Val Gly Glu Ile Asp Arg Ser Arg Ala Glu
```

-continued

```
                    260                 265                 270
Thr Gly Pro Leu Leu Ser Val Asp Lys Val Tyr Val His Lys Lys Phe
                275                 280                 285
Val Pro Pro Lys Lys Ser Gln Glu Phe Tyr Glu Lys Phe Asp Leu Val
            290                 295                 300
Ser Tyr Asp Tyr Asp Ile Ala Ile Ile Gln Met Lys Thr Pro Ile Gln
305                 310                 315                 320
Phe Ser Glu Asn Val Val Pro Ala Cys Leu Pro Thr Ala Asp Phe Ala
                325                 330                 335
Asn Gln Val Leu Met Lys Gln Asp Phe Gly Ile Val Ser Gly Phe Gly
            340                 345                 350
Gly Ile Phe Glu Arg Gly Pro Asn Ser Lys Thr Leu Lys Val Leu Lys
            355                 360                 365
Val Pro Tyr Val Asp Arg His Thr Cys Met Leu Ser Ser Asn Phe Pro
        370                 375                 380
Ile Thr Pro Thr Met Phe Cys Ala Gly Tyr Asp Thr Leu Pro Gln Asp
385                 390                 395                 400
Ala Cys Gln Gly Asp Ser Gly Gly Pro His Ile Thr Ala Tyr Arg Asp
                405                 410                 415
Thr His Phe Ile Thr Gly Ile Val Ser Trp Gly Glu Gly Cys Ala Arg
            420                 425                 430
Lys Gly Arg Tyr Gly Ile Tyr Thr Lys Leu Ser Lys Phe Ile Pro Trp
            435                 440                 445
Ile Lys Arg Ile Met Arg Gln Lys Leu Pro Ser Thr Glu Ser Ser Thr
        450                 455                 460
Gly Arg Leu
465

<210> SEQ ID NO 3
<211> LENGTH: 1401
<212> TYPE: DNA
<213> ORGANISM: Psuedonaja textilis

<400> SEQUENCE: 3
atggctcctc aactactcct ctgtctgatc ctcactttc tgtggagtct cccagaggct      60
gaaagtaatg tattcttaaa aagcaaagtg caaatagat ttttgcaaag aacaaaacga     120
gctaattcac tggttgagga atttaaatct ggaaacattg aaagggaatg cattgaggag     180
agatgttcaa agaagaagc cagggaggta tttgaagatg acgagaaaac tgagaccttc     240
tggaatgttt atgtagatgg ggatcagtgt tcatcaaacc cctgtcatta tcgcgggata     300
tgcaaagatg gcattggtag ctatacctgt acctgcttgt ctggctatga agggaaaaac     360
tgtgaacgtg tcttatataa gtcctgcaga gtggacaatg gtaactgttg gcacttctgc     420
aaatctgttc aaaacgatat tcaatgttca tgcgctgaag ttacctttt gggagaggat     480
gggcactctt gtgttgctgg aggtaacttt tcatgtggta gaaatatcaa acaaggaac     540
aagagggaag caagtctgcc tgactttgtg cagtcccata atgcaacttt gctgaaaaaa     600
tctgataatc aagccctga tatcagaatt gttaacggaa tggactgcaa actgggtgaa     660
tgtccgtggc aggcagctct ggtagatgac aagaaggtg tgttttgtgg aggaacaatt     720
ttgagtccca tctatgtgct tactgcagcc cactgcatta tgagaccga gacgatttca     780
gttgttgtag gagaaaatga cagatcaaga gcagaaaccg gacctcttct ttctgtggat     840
aaagtatatg tgcataaaaa aatttgttcct cccaaaaaaa gccaggaatt ctatgaaaag     900
```

-continued

```
tttgatcttg tcagctatga ctatgatata gccatcatcc aaatgaagac ccctatccag    960
ttctctgaaa atgtggttcc tgcctgcctt cccacagctg attttgccaa ccaagtcctc   1020
atgaaacaag attttggcat cgttagtgga tttgggggta ttttcgaaag aggaccgaac   1080
tctaaaacac ttaaagtcct taaggttcct tatgtgaca ggcacacctg catgctttcc    1140
agcaattttc caattactcc aactatgttc tgtgctggct atgatactct gcctcaagat   1200
gcatgccaag agacagcgg ggggcccac atcactgcat acagagatac ccactttatt    1260
actgggattg tcagctgggg ggaaggatgt gcacggaaag gcagatatgg tatttacaca   1320
aaattgtcca aattcatccc ttggataaaa agaataatgc gtcaaaagct acccagtaca   1380
gagtcaagca ctggtcggct c                                            1401

<210> SEQ ID NO 4
<211> LENGTH: 1404
<212> TYPE: DNA
<213> ORGANISM: Oxyuranus scutellatus
<220> FEATURE:
<221> NAME/K

```
                195                 200                 205
aga att gtt aat gga atg gac tgc aaa ctg ggt gaa tgt ccg tgg cag    672
Arg Ile Val Asn Gly Met Asp Cys Lys Leu Gly Glu Cys Pro Trp Gln
    210                 215                 220 gca gtt ctg gta gat gaa aag gaa gat gcg ttt tgt gga gga aca att    720
Ala Val Leu Val Asp Glu Lys Glu Asp Ala Phe Cys Gly Gly Thr Ile
225                 230                 235                 240 ttg agt ccc atc tat gtg ctt act gca gcc cac tgc att aac cag acc    768
Leu Ser Pro Ile Tyr Val Leu Thr Ala Ala His Cys Ile Asn Gln Thr
        245                 250                 255 aag atg att tca gtt gtt gta ggg gaa ata aac ata tca aga aaa aac    816
Lys Met Ile Ser Val Val Val Gly Glu Ile Asn Ile Ser Arg Lys Asn
            260                 265                 270 ccc gga cgt ctt ctt tct gtg gat aaa ata tat gtg cat caa aaa ttt    864
Pro Gly Arg Leu Leu Ser Val Asp Lys Ile Tyr Val His Gln Lys Phe
                275                 280                 285 gtt cct ccc aaa aaa ggc tat gaa ttc tat gaa aag ttt gat ctt gtc    912
Val Pro Pro Lys Lys Gly Tyr Glu Phe Tyr Glu Lys Phe Asp Leu Val
    290                 295                 300 agc tat gac tat gat ata gcc atc ctc caa atg aag acc cct atc cag    960
Ser Tyr Asp Tyr Asp Ile Ala Ile Leu Gln Met Lys Thr Pro Ile Gln
305                 310                 315                 320 ttc tct gaa aat gtg gtt cct gcc tgc ctt ccc aca gct gat ttt gcc   1008
Phe Ser Glu Asn Val Val Pro Ala Cys Leu Pro Thr Ala Asp Phe Ala
        325                 330                 335 aac caa gtc ctc atg aaa caa gat ttt ggc atc gtt agt gga ttt ggg   1056
Asn Gln Val Leu Met Lys Gln Asp Phe Gly Ile Val Ser Gly Phe Gly
            340                 345                 350 cgt att ttc gaa aaa gga cct caa tct aaa aca ctt aaa gtc ctt aag   1104
Arg Ile Phe Glu Lys Gly Pro Gln Ser Lys Thr Leu Lys Val Leu Lys
                355                 360                 365 gtt cct tat gtg gac agg cac acc tgc atg ctt tcc agc gaa tct cca   1152
Val Pro Tyr Val Asp Arg His Thr Cys Met Leu Ser Ser Glu Ser Pro
    370                 375                 380 att act cca act atg ttc tgt gct ggc tat gat act ctg cct cga gat   1200
Ile Thr Pro Thr Met Phe Cys Ala Gly Tyr Asp Thr Leu Pro Arg Asp
385                 390                 395                 400 gca tgc cag gga gac agt ggg ggg ccc cac atc act gca tac aga gat   1248
Ala Cys Gln Gly Asp Ser Gly Gly Pro His Ile Thr Ala Tyr Arg Asp
        405                 410                 415 acc cac ttt att act ggg att gtc agc tgg ggg gaa gga tgt gca cag   1296
Thr His Phe Ile Thr Gly Ile Val Ser Trp Gly Glu Gly Cys Ala Gln
            420                 425                 430 aca ggc aaa tat ggt gtt tac aca aaa gtg tcc aaa ttc atc ctt tgg   1344
Thr Gly Lys Tyr Gly Val Tyr Thr Lys Val Ser Lys Phe Ile Leu Trp
                435                 440                 445 ata aaa aga ata atg cgt caa aag cta ccc agt aca gag tca agc act   1392
Ile Lys Arg Ile Met Arg Gln Lys Leu Pro Ser Thr Glu Ser Ser Thr
    450                 455                 460 ggt cgg ctc taa                                                    1404
Gly Arg Leu
465

<210> SEQ ID NO 5
<211> LENGTH: 467
<212> TYPE: PRT
<213> ORGANISM: Oxyuranus scutellatus

<400> SEQUENCE: 5

Met Ala Pro Gln Leu Leu Leu Cys Leu Ile Leu Thr Phe Leu Trp Ser
```

```
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ala Asn Ser Leu Tyr Glu Glu Phe
            35                  40                  45

Arg Ser Gly Asn Ile Glu Arg Glu Cys Ile Glu Glu Arg Cys Ser Lys
        50                  55                  60

Glu Glu Ala Arg Glu Val Phe Glu Asp Asp Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Ser Gly Tyr Glu Gly Lys Asn Cys Glu Arg Val Leu Tyr Lys Ser
        115                 120                 125

Cys Arg Val Asp Asn Gly Asn Cys Trp His Phe Cys Lys Pro Val Gln
    130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Ser Leu Pro Asp Phe Val Gln Ser
            180                 185                 190

Gln Asn Ala Ile Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Val Asp Glu Lys Glu Asp Ala Phe Cys Gly Gly Thr Ile
225                 230                 235                 240

Leu Ser Pro Ile Tyr Val Leu Thr Ala Ala His Cys Ile Asn Gln Thr
                245                 250                 255

Lys Met Ile Ser Val Val Gly Glu Ile Asn Ile Ser Arg Lys Asn
            260                 265                 270

Pro Gly Arg Leu Leu Ser Val Asp Lys Ile Tyr Val His Gln Lys Phe
        275                 280                 285

Val Pro Pro Lys Lys Gly Tyr Glu Phe Tyr Glu Lys Phe Asp Leu Val
    290                 295                 300

Ser Tyr Asp Tyr Asp Ile Ala Ile Leu Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Val Ser Gly Phe Gly
            340                 345                 350

Arg Ile Phe Glu Lys Gly Pro Gln Ser Lys Thr Leu Lys Val Leu Lys
        355                 360                 365

Val Pro Tyr Val Asp Arg His Thr Cys Met Leu Ser Ser Glu Ser Pro
    370                 375                 380

Ile Thr Pro Thr Met Phe Cys Ala Gly Tyr Asp Thr Leu Pro Arg Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Gln
            420                 425                 430
```

```
Thr Gly Lys Tyr Gly Val Tyr Thr Lys Val Ser Lys Phe Ile Leu Trp
        435                 440                 445

Ile Lys Arg Ile Met Arg Gln Lys Leu Pro Ser Thr Glu Ser Ser Thr
    450                 455                 460

Gly Arg Leu
465

<210> SEQ ID NO 6
<211> LENGTH: 1401
<212> TYPE: DNA
<213> ORGANISM: Oxyuranus scutellatus

<400> SEQUENCE: 6
atggctcctc aactactcct ctgtctgatc ctcactttc tgtggagtct cccagaggcc      60
gaaagtaatg tattcttaaa aagcaaagtg gcaaatagat ttttgcaaag aacaaaacga    120
gctaattcac tgtatgagga atttagatct ggaaacattg aaagggaatg cattgaggag    180
agatgttcaa agaagaagc cagggaggta tttgaagatg acgagaaaac tgagaccttc    240
tggaatgttt atgtagatgg ggatcagtgt tcatcaaacc cctgtcatta tcgcgggaca    300
tgcaaagatg gcattggtag ctatacctgt acctgcttgt ctggctatga agggaaaaac    360
tgtgaacgtg tcttatataa gtcctgcaga gtggacaatg taactgttg gcacttctgc    420 aaacctgttc aaaacgatat tcagtgttca tgtgctgaag gttaccttt gggagaggat    480 gggcactctt gtgttgctgg aggtaacttt tcatgtggta gaaatatcaa acaaggaac    540 aagagggaag caagtctgcc tgactttgtg cagtcccaga atgcaattt gctgaaaaaa    600 tctgataatc aagccctga tatcagaatt gttaatggaa tggactgcaa actgggtgaa    660
tgtccgtggc aggcagttct ggtagatgaa aaggaagatg cgttttgtgg aggaacaatt    720
ttgagtccca tctatgtgct tactgcagcc cactgcatta accagaccaa gatgattca    780 gttgttgtag gggaaataaa catatcaaga aaaaaccccg gacgtcttct ttctgtggat    840
aaaatatatg tgcatcaaaa atttgttcct cccaaaaaag gctatgaatt ctatgaaaag    900
tttgatcttg tcagctatga ctatgatata gccatcctcc aaatgaagac ccctatccag    960
ttctctgaaa atgtggttcc tgcctgcctt cccacagctg attttgccaa ccaagtcctc   1020
atgaaacaag attttggcat cgttagtgga tttgggcgta ttttcgaaaa aggacctcaa   1080
tctaaaacac ttaaagtcct taaggttcct tatgtggaca ggcacacctg catgctttcc   1140
agcgaatctc caattactcc aactatgttc tgtgctggct atgatactct gcctcgagat   1200
gcatgccagg gagacagtgg ggggccccac atcactgcat acagagatac ccactttatt   1260
actgggattg tcagctgggg ggaaggatgt gcacagacag gcaaatatgg tgtttacaca   1320
aaagtgtcca aattcatcct ttggataaaa agaataatgc gtcaaaagct acccagtaca   1380
gagtcaagca ctggtcggct c                                              1401

<210> SEQ ID NO 7
<211> LENGTH: 1404
<212> TYPE: DNA
<213> ORGANISM: Oxyuranus microlepitdotus
<220> FEATURE:
<221> NAME/KEY: CDS
<222> LOCATION: (1)..(1401)

<400> SEQUENCE: 7 atg gct cct caa cta ctc ctc tgt ctg atc ctc act ttt ctg tgg agt      48
Met Ala Pro Gln Leu Leu Leu Cys Leu Ile Leu Thr Phe Leu Trp Ser
```

| | | | | | | | | | | | | | | | | |
|---|---|---|---|---|---|---|---|---|---|---|---|---|---|---|---|---|
| ctc | cca | gag | gct | gaa | agt | aat | gta | ttc | tta | aaa | agc | aaa | gtg | gca | aat | 96 |
| Leu | Pro | Glu | Ala | Glu | Ser | Asn | Val | Phe | Leu | Lys | Ser | Lys | Val | Ala | Asn | |
| | | | 20 | | | | | 25 | | | | | 30 | | | |
| aga | ttt | ttg | caa | aga | aca | aaa | cga | gct | aat | tca | ctg | ttt | gag | gaa | ttt | 144 |
| Arg | Phe | Leu | Gln | Arg | Thr | Lys | Arg | Ala | Asn | Ser | Leu | Phe | Glu | Glu | Phe | |
| | | 35 | | | | | 40 | | | | | 45 | | | | |
| aga | tct | gga | aac | att | gaa | agg | gaa | tgc | att | gag | gag | aga | tgt | tca | aaa | 192 |
| Arg | Ser | Gly | Asn | Ile | Glu | Arg | Glu | Cys | Ile | Glu | Glu | Arg | Cys | Ser | Lys | |
| | 50 | | | | | 55 | | | | | 60 | | | | | |
| gaa | gaa | gcc | agg | gag | gta | ttt | gaa | gat | gac | gag | aaa | act | gag | acc | ttc | 240 |
| Glu | Glu | Ala | Arg | Glu | Val | Phe | Glu | Asp | Asp | Glu | Lys | Thr | Glu | Thr | Phe | |
| 65 | | | | | 70 | | | | | 75 | | | | | 80 | |
| tgg | aat | gtt | tat | gta | gat | ggg | gat | cag | tgt | tca | tca | aac | ccc | tgt | cat | 288 |
| Trp | Asn | Val | Tyr | Val | Asp | Gly | Asp | Gln | Cys | Ser | Ser | Asn | Pro | Cys | His | |
| | | | | 85 | | | | | 90 | | | | | 95 | | |
| tat | cgc | ggg | aca | tgc | aaa | gat | ggc | att | ggt | agc | tat | acc | tgt | acc | tgc | 336 |
| Tyr | Arg | Gly | Thr | Cys | Lys | Asp | Gly | Ile | Gly | Ser | Tyr | Thr | Cys | Thr | Cys | |
| | | | 100 | | | | | 105 | | | | | 110 | | | |
| ttg | ttt | ggc | tat | gaa | ggg | aaa | aac | tgt | gaa | cgt | gtc | tta | tat | aag | tcc | 384 |
| Leu | Phe | Gly | Tyr | Glu | Gly | Lys | Asn | Cys | Glu | Arg | Val | Leu | Tyr | Lys | Ser | |
| | | 115 | | | | | 120 | | | | | 125 | | | | |
| tgc | aga | gtg | gac | aat | ggt | aac | tgt | tgg | cac | ttc | tgc | aaa | cct | gtt | caa | 432 |
| Cys | Arg | Val | Asp | Asn | Gly | Asn | Cys | Trp | His | Phe | Cys | Lys | Pro | Val | Gln | |
| | 130 | | | | | 135 | | | | | 140 | | | | | |
| aac | gat | att | cag | tgt | tca | tgt | gct | gaa | ggt | tac | ctt | ttg | gga | gag | gat | 480 |
| Asn | Asp | Ile | Gln | Cys | Ser | Cys | Ala | Glu | Gly | Tyr | Leu | Leu | Gly | Glu | Asp | |
| 145 | | | | | 150 | | | | | 155 | | | | | 160 | |
| ggg | cac | tct | tgt | gtt | gct | gga | ggt | aac | ttt | tca | tgt | ggt | aga | aat | atc | 528 |
| Gly | His | Ser | Cys | Val | Ala | Gly | Gly | Asn | Phe | Ser | Cys | Gly | Arg | Asn | Ile | |
| | | | | 165 | | | | | 170 | | | | | 175 | | |
| aaa | aca | agg | aac | aag | agg | gaa | gca | agt | ctg | cct | gac | ttt | gtg | cag | tcc | 576 |
| Lys | Thr | Arg | Asn | Lys | Arg | Glu | Ala | Ser | Leu | Pro | Asp | Phe | Val | Gln | Ser | |
| | | | 180 | | | | | 185 | | | | | 190 | | | |
| cag | aat | gca | act | ttg | ctg | aaa | aaa | tct | gat | aat | cca | agc | cct | gat | atc | 624 |
| Gln | Asn | Ala | Thr | Leu | Leu | Lys | Lys | Ser | Asp | Asn | Pro | Ser | Pro | Asp | Ile | |
| | | 195 | | | | | 200 | | | | | 205 | | | | |
| aga | att | gtt | aat | gga | atg | gac | tgc | aaa | ctg | ggt | gaa | tgt | ccg | tgg | cag | 672 |
| Arg | Ile | Val | Asn | Gly | Met | Asp | Cys | Lys | Leu | Gly | Glu | Cys | Pro | Trp | Gln | |
| | 210 | | | | | 215 | | | | | 220 | | | | | |
| gca | gtt | ctg | gta | gat | gaa | aag | gaa | ggt | gtg | ttt | tgt | gga | gga | aca | att | 720 |
| Ala | Val | Leu | Val | Asp | Glu | Lys | Glu | Gly | Val | Phe | Cys | Gly | Gly | Thr | Ile | |
| 225 | | | | | 230 | | | | | 235 | | | | | 240 | |
| ttg | agt | ccc | atc | tat | gtg | ctt | act | gca | gcc | cac | tgc | att | aac | cag | acc | 768 |
| Leu | Ser | Pro | Ile | Tyr | Val | Leu | Thr | Ala | Ala | His | Cys | Ile | Asn | Gln | Thr | |
| | | | | 245 | | | | | 250 | | | | | 255 | | |
| gag | aag | att | tca | gtt | gtt | gta | ggg | gaa | ata | gac | aaa | tca | aga | gta | gaa | 816 |
| Glu | Lys | Ile | Ser | Val | Val | Val | Gly | Glu | Ile | Asp | Lys | Ser | Arg | Val | Glu | |
| | | | 260 | | | | | 265 | | | | | 270 | | | |
| acc | gga | cat | ctt | ctt | tct | gtg | gat | aaa | ata | tat | gtg | cat | aaa | aaa | ttt | 864 |
| Thr | Gly | His | Leu | Leu | Ser | Val | Asp | Lys | Ile | Tyr | Val | His | Lys | Lys | Phe | |
| | | 275 | | | | | 280 | | | | | 285 | | | | |
| gtt | cct | ccc | aaa | aaa | ggc | tat | aaa | ttc | tat | gaa | aag | ttt | gat | ctt | gtc | 912 |
| Val | Pro | Pro | Lys | Lys | Gly | Tyr | Lys | Phe | Tyr | Glu | Lys | Phe | Asp | Leu | Val | |
| | 290 | | | | | 295 | | | | | 300 | | | | | |
| agc | tat | gac | tat | gat | ata | gcc | atc | atc | caa | atg | aag | acc | cct | atc | cag | 960 |
| Ser | Tyr | Asp | Tyr | Asp | Ile | Ala | Ile | Ile | Gln | Met | Lys | Thr | Pro | Ile | Gln | |
| 305 | | | | | 310 | | | | | 315 | | | | | 320 | |
| ttc | tct | gaa | aat | gtg | gtt | cct | gcc | tgc | ctt | ccc | aca | gct | gat | ttt | gcc | 1008 |

```
Phe Ser Glu Asn Val Val Pro Ala Cys Leu Pro Thr Ala Asp Phe Ala
                325                 330

-continued

```
Lys Thr Arg Asn Lys Arg Glu Ala Ser Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Gln Thr
                245                 250                 255

Glu Lys Ile Ser Val Val Val Gly Glu Ile Asp Lys Ser Arg Val Glu
            260                 265                 270

Thr Gly His Leu Leu Ser Val Asp Lys Ile Tyr Val His Lys Lys Phe
        275                 280                 285

Val Pro Pro Lys Lys Gly Tyr Lys Phe Tyr Glu Lys Phe Asp Leu Val
    290                 295                 300

Ser Tyr Asp Tyr Asp Ile Ala Ile Ile Gln Met Lys Thr Pro Ile Gln
305                 310                 315                 320

Phe Ser Glu Asn Val Val Pro Ala Cys Leu Pro Thr Ala Asp Phe Ala
                325                 330                 335

Asn Gln Val Leu Met Lys Gln Asp Phe Gly Ile Ile Ser Gly Phe Gly
            340                 345                 350

Arg Ile Phe Glu Lys Gly Pro Lys Ser Asn Thr Leu Lys Val Leu Lys
        355                 360                 365

Val Pro Tyr Val Asp Arg His Thr Cys Met Val Ser Ser Glu Ser Pro
    370                 375                 380

Ile Thr Pro Thr Met Phe Cys Ala Gly Tyr Asp Thr Leu Pro Arg Asp
385                 390                 395                 400

Ala Cys Gln Gly Asp Ser Gly Gly Pro His Ile Thr Ala Tyr Arg Asp
                405                 410                 415

Thr His Phe Ile Thr Gly Ile Val Ser Trp Gly Glu Gly Cys Ala Lys
            420                 425                 430

Lys Gly Lys Tyr Gly Ile Tyr Thr Lys Val Ser Lys Phe Ile Leu Trp
        435                 440                 445

Ile Lys Arg Ile Met Arg Gln Lys Leu Pro Ser Thr Glu Ser Ser Thr
    450                 455                 460

Gly Arg Leu
465
```

<210> SEQ ID NO 9
<211> LENGTH: 1401
<212> TYPE: DNA
<213> ORGANISM: Oxyuranus microlepidotus

<400> SEQUENCE: 9

```
atggctcctc aactactcct ctgtctgatc ctcacttttc tgtggagtct cccagaggct     60
gaaagtaatg tattcttaaa aagcaaagtg gcaaatagat ttttgcaaag aacaaaacga    120
gctaattcac tgtttgagga atttagatct ggaaacattg aaagggaatg cattgaggag    180
agatgttcaa aagaagaagc cagggaggta tttgaagatg acgagaaaac tgagaccttc    240
tggaatgttt atgtagatgg ggatcagtgt tcatcaaacc cctgtcatta tcgcgggaca    300
tgcaaagatg gcattggtag ctatacctgt acctgcttgt ttggctatga agggaaaaac    360
tgtgaacgtg tcttatataa gtcctgcaga gtggacaatg gtaactgttg gcacttctgc    420
```

```
aaacctgttc aaaacgatat tcagtgttca tgtgctgaag gttaccttt  gggagaggat      480 gggcactctt gtgttgctgg aggtaacttt tcatgtggta gaaatatcaa acaaggaac      540 aagagggaag caagtctgcc tgactttgtg cagtcccaga atgcaacttt gctgaaaaaa      600
tctgataatc caagccctga tatcagaatt gttaatggaa tggactgcaa actgggtgaa      660
tgtccgtggc aggcagttct ggtagatgaa aggaaggtg  tgttttgtgg aggaacaatt      720
ttgagtccca tctatgtgct tactgcagcc cactgcatta accagaccga aagatttca      780 gttgttgtag gggaaataga caaatcaaga gtagaaaccg acatcttct  ttctgtggat      840 aaaatatatg tgcataaaaa atttgttcct cccaaaaaag gctataaatt ctatgaaaag      900
tttgatcttg tcagctatga ctatgatata gccatcatcc aaatgaagac ccctatccag      960
ttctctgaaa atgtggttcc tgcctgcctt cccacagctg attttgccaa ccaagtcctc     1020
atgaaacaag attttggcat cattagtgga tttgggcgta ttttcgaaaa aggaccgaaa     1080
tctaacacac ttaaagtcct taaggttcct tatgtggaca ggcacacctg catggtttcc     1140
agcgaatctc caattactcc aactatgttc tgtgctggct atgatactct gcctcgagat     1200
gcatgccagg gagacagtgg ggggccccac atcactgcat acagagatac ccactttatt     1260
actgggattg tcagctgggg ggaaggatgt gctaagaaag gcaaatatgg tatttacaca     1320
aaagtgtcca aattcatcct tggataaaaa agaataatgc gtcaaaagct acccagtaca     1380
gagtcaagca ctggtcggct c                                               1401

<210> SEQ ID NO 10
<211> LENGTH: 1365
<212> TYPE: DNA
<213> ORGANISM: Pseudechis porphyriacus
<220> FEATURE:
<221> NAME/KEY: CDS
<222> LOCATION: (1)..(1362)

<400> SEQUENCE: 10 atg gct cct caa cta ctc ctc tgt ctg atc ctc act ttt ctc tgg agt       48
Met Ala Pro Gln Leu Leu Leu Cys Leu Ile Leu Thr Phe Leu Trp Ser
1               5                   10                  15 ctc ccg gag gct gaa agt aat gta ttc tta aaa agc aaa gag gca aat       96
Leu Pro Glu Ala Glu Ser Asn Val Phe Leu Lys Ser Lys Glu Ala Asn
            20                  25                  30 aga ttt ttg caa aga aca aaa cga tct aat tca ctg ttt gag gaa ttt      144
Arg Phe Leu Gln Arg Thr Lys Arg Ser Asn Ser Leu Phe Glu Glu Phe
        35                  40                  45 aga cct gga aac att gaa agg gaa tgc att gag gag aaa tgt tca aaa      192
Arg Pro Gly Asn Ile Glu Arg Glu Cys Ile Glu Glu Lys Cys Ser Lys
    50                  55                  60 gaa gaa gcc agg gag ata ttt aaa gat aac gag aaa act gag gcc ttt      240
Glu Glu Ala Arg Glu Ile Phe Lys Asp Asn Glu Lys Thr Glu Ala Phe
65                  70                  75                  80 tgg aat gtt tat gta gat ggg gat cag tgt tca tca aac ccc tgt cat      288
Trp Asn Val Tyr Val Asp Gly Asp Gln Cys Ser Ser Asn Pro Cys His
                85                  90                  95 tat ggt ggg aca tgc aaa gat ggc att ggt agc tat acc tgt acc tgc      336
Tyr Gly Gly Thr Cys Lys Asp Gly Ile Gly Ser Tyr Thr Cys Thr Cys
            100                 105                 110 ttg cct aac tat gaa ggg aaa aac tgt gaa cat ctc tta ttt aag tcc      384
Leu Pro Asn Tyr Glu Gly Lys Asn Cys Glu His Leu Leu Phe Lys Ser
        115                 120                 125 tgc aga ttt ttc aat ggt aac tgt tgg cac ttc tgc aaa cct gtt caa      432
Cys Arg Phe Phe Asn Gly Asn Cys Trp His Phe Cys Lys Pro Val Gln
```

```
                Cys Arg Phe Phe Asn Gly Asn Cys Trp His Phe Cys Lys Pro Val Gln
                    130                 135                 140 aac gac act cag tgt tca tgt gct gaa agt tac cgt ttg gga gat gat          480
Asn Asp Thr Gln Cys Ser Cys Ala Glu Ser Tyr Arg Leu Gly Asp Asp
145                 150                 155                 160 ggg cac tct tgt gtt gct gaa ggt gac ttt tca tgt ggt aga aat ata          528
Gly His Ser Cys Val Ala Glu Gly Asp Phe Ser Cys Gly Arg Asn Ile
                165                 170                 175 aaa gca agg aac aag agg gaa gca agt ctg cct gac ttt gtg cag tcc          576
Lys Ala Arg Asn Lys Arg Glu Ala Ser Leu Pro Asp Phe Val Gln Ser
            180                 185                 190 cag aat gca act ttg ctg aaa aaa tct gat aat cca agc cct gat atc          624
Gln Asn Ala Thr Leu Leu Lys Lys Ser Asp Asn Pro Ser Pro Asp Ile
        195                 200                 205 aga att att aat gga atg gac tgc aaa ctg ggt gaa tgt cca tgg cag          672
Arg Ile Ile Asn Gly Met Asp Cys Lys Leu Gly Glu Cys Pro Trp Gln
    210                 215                 220 gca gtt ctg cta gat aaa gaa gga gat gtg ttt tgt gga gga aca att          720
Ala Val Leu Leu Asp Lys Glu Gly Asp Val Phe Cys Gly Gly Thr Ile
225                 230                 235                 240 ttg agt ccc atc tat gtg ctt act gca gcc cac tgc att acc cag tcc          768
Leu Ser Pro Ile Tyr Val Leu Thr Ala Ala His Cys Ile Thr Gln Ser
                245                 250                 255 aag cac att tca gtt gtt gta ggg gaa ata gat ata tca aga aaa gaa          816
Lys His Ile Ser Val Val Val Gly Glu Ile Asp Ile Ser Arg Lys Glu
                260                 265                 270 acc aga cat ctt ctt tct gta gat aaa gca tat gtg cat aca aaa ttt          864
Thr Arg His Leu Leu Ser Val Asp Lys Ala Tyr Val His Thr Lys Phe
            275                 280                 285 gtt ctt gcc acc tat gac tat gat ata gcc atc atc caa ttg aag acc          912
Val Leu Ala Thr Tyr Asp Tyr Asp Ile Ala Ile Ile Gln Leu Lys Thr
        290                 295                 300 cct atc cag ttc tct gaa aat gtg gtt cct gcc tgt ctt ccc act gct          960
Pro Ile Gln Phe Ser Glu Asn Val Val Pro Ala Cys Leu Pro Thr Ala
305                 310                 315                 320 gat ttt gcc aac caa gtc ctc atg aaa caa gat ttt ggc atc att agt         1008
Asp Phe Ala Asn Gln Val Leu Met Lys Gln Asp Phe Gly Ile Ile Ser
                325                 330                 335 gga ttt ggg cat act cga tct gga gga cag acc tct aac aca ctt aaa         1056
Gly Phe Gly His Thr Arg Ser Gly Gly Gln Thr Ser Asn Thr Leu Lys
                340                 345                 350 gtc gtt acg att cct tat gtg gac agg cac acc tgc atg ctt tcc agc         1104
Val Val Thr Ile Pro Tyr Val Asp Arg His Thr Cys Met Leu Ser Ser
            355                 360                 365 gat ttt cga att act cca aat atg ttc tgt gct ggt tat gat act ctg         1152
Asp Phe Arg Ile Thr Pro Asn Met Phe Cys Ala Gly Tyr Asp Thr Leu
        370                 375                 380 cct cga gat gca tgc cag gga gac agt ggg ggg ccc cac atc act gca         1200
Pro Arg Asp Ala Cys Gln Gly Asp Ser Gly Gly Pro His Ile Thr Ala
385                 390                 395                 400 tac aga gat acc cac ttt att act ggg att atc agc tgg ggg gaa gga         1248
Tyr Arg Asp Thr His Phe Ile Thr Gly Ile Ile Ser Trp Gly Glu Gly
                405                 410                 415 tgt gca aag aaa ggc aaa tat ggt gtt tac aca aaa gtg tcc aac ttc         1296
Cys Ala Lys Lys Gly Lys Tyr Gly Val Tyr Thr Lys Val Ser Asn Phe
                420                 425                 430 atc cct tgg ata aaa gca gta atg cgt aaa cat caa ccc agt aca gag         1344
Ile Pro Trp Ile Lys Ala Val Met Arg Lys His Gln Pro Ser Thr Glu
            435                 440                 445
```

```
tca agc act ggt cgg ctc taa                                    1365
Ser Ser Thr Gly Arg Leu
    450
```

<210> SEQ ID NO 11
<211> LENGTH: 454
<212> TYPE: PRT
<213> ORGANISM: Pseudechis porphyriacus

<400> SEQUENCE: 11

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Glu Ala Asn
                20                  25                  30

Arg Phe Leu Gln Arg Thr Lys Arg Ser Asn Ser Leu Phe Glu Glu Phe
        35                  40                  45

Arg Pro Gly Asn Ile Glu Arg Glu Cys Ile Glu Glu Lys Cys Ser Lys
    50                  55                  60

Glu Glu Ala Arg Glu Ile Phe Lys Asp Asn Glu Lys Thr Glu Ala Phe
65                  70                  75                  80

Trp Asn Val Tyr Val Asp Gly Asp Gln Cys Ser Ser Asn Pro Cys His
                85                  90                  95

Tyr Gly Gly Thr Cys Lys Asp Gly Ile Gly Ser Tyr Thr Cys Thr Cys
            100                 105                 110

Leu Pro Asn Tyr Glu Gly Lys Asn Cys Glu His Leu Leu Phe Lys Ser
        115                 120                 125

Cys Arg Phe Phe Asn Gly Asn Cys Trp His Phe Cys Lys Pro Val Gln
    130                 135                 140

Asn Asp Thr Gln Cys Ser Cys Ala Glu Ser Tyr Arg Leu Gly Asp Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Ile Asn Gly Met Asp Cys Lys Leu Gly Glu Cys Pro Trp Gln
    210                 215                 220

Ala Val Leu Leu Asp Lys Glu Gly Asp Val Phe Cys Gly Gly Thr Ile
225                 230                 235                 240

Leu Ser Pro Ile Tyr Val Leu Thr Ala Ala His Cys Ile Thr Gln Ser
                245                 250                 255

Lys His Ile Ser Val Val Gly Glu Ile Asp Ile Ser Arg Lys Glu
            260                 265                 270

Thr Arg His Leu Leu Ser Val Asp Lys Ala Tyr Val His Thr Lys Phe
        275                 280                 285

Val Leu Ala Thr Tyr Asp Tyr Asp Ile Ala Ile Ile Gln Leu Lys Thr
    290                 295                 300

Pro Ile Gln Phe Ser Glu Asn Val Pro Ala Cys Leu Pro Thr Ala
305                 310                 315                 320

Asp Phe Ala Asn Gln Val Leu Met Lys Gln Asp Phe Gly Ile Ile Ser
                325                 330                 335

Gly Phe Gly His Thr Arg Ser Gly Gly Gln Thr Ser Asn Thr Leu Lys
            340                 345                 350

Val Val Thr Ile Pro Tyr Val Asp Arg His Thr Cys Met Leu Ser Ser
```

```
                    355                 360                 365
Asp Phe Arg Ile Thr Pro Asn Met Phe Cys Ala Gly Tyr Asp Thr Leu
        370                 375                 380

Pro Arg Asp Ala Cys Gln Gly Asp Ser Gly Gly Pro His Ile Thr Ala
385                 390                 395                 400

Tyr Arg Asp Thr His Phe Ile Thr Gly Ile Ile Ser Trp Gly Glu Gly
                405                 410                 415

Cys Ala Lys Lys Gly Lys Tyr Gly Val Tyr Thr Lys Val Ser Asn Phe
                420                 425                 430

Ile Pro Trp Ile Lys Ala Val Met Arg Lys His Gln Pro Ser Thr Glu
                435                 440                 445

Ser Ser Thr Gly Arg Leu
    450
```

```
<210> SEQ ID NO 12
<211> LENGTH: 1362
<212> TYPE: DNA
<213> ORGANISM: Pseudechis porphyriacus

<400> SEQUENCE: 12
atggctcctc aactactcct ctgtctgatc ctcactttc tctggagtct cccggaggct      60
gaaagtaatg tattcttaaa aagcaaagag gcaaatagat ttttgcaaag aacaaaacga    120
tctaattcac tgtttgagga atttagacct ggaaacattg aaagggaatg cattgaggag    180
aaatgttcaa agaagaagc cagggagata tttaagata cgagaaaac tgaggccttt      240
tggaatgttt atgtagatgg ggatcagtgt tcatcaaacc cctgtcatta tggtgggaca    300
tgcaaagatg gcattggtag ctatacctgt acctgcttgc ctaactatga agggaaaaac    360
tgtgaacatc tcttatttaa gtcctgcaga ttttcaatg gtaactgttg gcacttctgc    420
aaacctgttc aaaacgacac tcagtgttca tgtgctgaaa gttaccgttt gggagatgat    480
gggcactctt gtgttgctga aggtgacttt tcatgtggta gaaatataaa agcaaggaac    540
aagagggaag caagtctgcc tgactttgtg cagtcccaga atgcaacttt gctgaaaaaa    600
tctgataatc caagccctga tatcagaatt attaatggaa tggactgcaa actgggtgaa    660
tgtccatggc aggcagttct gctagataaa gaaggagatg tgttttgtgg aggaacaatt    720
ttgagtccca tctatgtgct tactgcagcc cactgcatta cccagtccaa gcacatttca    780
gttgttgtag gggaaataga tatatcaaga aaagaaacca gacatcttct ttctgtagat    840
aaagcatatg tgcatacaaa atttgttctt gccacctatg actatgatat agccatcatc    900
caattgaaga cccctatcca gttctctgaa aatgtggttc ctgcctgtct tcccactgct    960
gattttgcca ccaagtcct catgaaacaa gattttggca tcattagtgg atttgggcat   1020
actcgatctg gaggacagac ctctaacaca cttaaagtcg ttacgattcc ttatgtggac   1080
aggcacacct gcatgctttc cagcgatttt cgaattactc aaatatgtt ctgtgctggt   1140
tatgatactc tgcctcgaga tgcatgccag ggagacagtg ggggcccca catcactgca   1200
tacagagata cccactttat tactgggatt atcagctggg gggaaggatg tgcaaagaaa   1260
ggcaaatatg gtgtttacac aaaagtgtcc aacttcatcc cttggataaa agcagtaatg   1320
cgtaaacatc aacccagtac agagtcaagc actggtcggc tc                     1362

<210> SEQ ID NO 13
<211> LENGTH: 1395
<212> TYPE: DNA
<213> ORGANISM: Notechis scutatus
```

```
<220> FEATURE:
<221> NAME/KEY: CDS
<222> LOCATION: (1)..(1359)

<400> SEQUENCE: 13 atg gct cct caa cta ctc ctc tgt ctg atc ctc act ttt ctg tgg agt      48
Met Ala Pro Gln Leu Leu Leu Cys Leu Ile Leu Thr Phe Leu Trp Ser
1               5                   10                  15 ctc cca gag gct gaa agt aat gta ttc tta aaa agc aaa gtg gca aat      96
Leu Pro Glu Ala Glu Ser Asn Val Phe Leu Lys Ser Lys Val Ala Asn
                20                  25                  30 aga ttt ttg caa aga aca aaa cga tct aat tca ctg ttt gag gaa att     144
Arg Phe Leu Gln Arg Thr Lys Arg Ser Asn Ser Leu Phe Glu Glu Ile
            35                  40                  45 aga cct gga aac att gaa agg gaa tgc att gag gag aaa tgt tca aaa     192
Arg Pro Gly Asn Ile Glu Arg Glu Cys Ile Glu Glu Lys Cys Ser Lys
        50                  55                  60 gaa gaa gcc agg gag gta ttt gaa gat aac gag aaa act gag acc ttc     240
Glu Glu Ala Arg Glu Val Phe Glu Asp Asn Glu Lys Thr Glu Thr Phe
65                  70                  75                  80 tgg aat gtt tat gta gat ggg gat cag tgt tca tca aac ccc tgt cat     288
Trp Asn Val Tyr Val Asp Gly Asp Gln Cys Ser Ser Asn Pro Cys His
                85                  90                  95 tat cgc ggg aca tgc aaa gat ggc att ggt agc tat acc tgt acc tgc     336
Tyr Arg Gly Thr Cys Lys Asp Gly Ile Gly Ser Tyr Thr Cys Thr Cys
                100                 105                 110 ttg cct aac tat gaa ggg aaa aac tgt gaa aaa gtc tta ttt aag tcc     384
Leu Pro Asn Tyr Glu Gly Lys Asn Cys Glu Lys Val Leu Phe Lys Ser
            115                 120                 125 tgc aga gca ttc aat ggt aac tgt tgg cac ttc tgc aaa cgt gtt caa     432
Cys Arg Ala Phe Asn Gly Asn Cys Trp His Phe Cys Lys Arg Val Gln
        130                 135                 140 agt gaa act cag tgt tca tgt gct gaa agt tac ctt ttg gga gtt gat     480
Ser Glu Thr Gln Cys Ser Cys Ala Glu Ser Tyr Leu Leu Gly Val Asp
145                 150                 155                 160 ggg cac tct tgt gtt gct gaa ggt gac ttt tca tgt ggt aga aat ata     528
Gly His Ser Cys Val Ala Glu Gly Asp Phe Ser Cys Gly Arg Asn Ile
                165                 170                 175 aaa gca agg aac aag agg gaa gca agt ctg cct gac ttt gtg cag tcc     576
Lys Ala Arg Asn Lys Arg Glu Ala Ser Leu Pro Asp Phe Val Gln Ser
                180                 185                 190 cag aag gca act gtg ctg aaa aaa tct gat aat cca agc cct gat atc     624
Gln Lys Ala Thr Val Leu Lys Lys Ser Asp Asn Pro Ser Pro Asp Ile
            195                 200                 205 aga att gtt aat gga atg gac tgc aaa ctg ggt gaa tgt cca tgg cag     672
Arg Ile Val Asn Gly Met Asp Cys Lys Leu Gly Glu Cys Pro Trp Gln
        210                 215                 220 gca gtt ctg ata aat gaa aaa gga gaa gtg ttt tgt gga gga aca att     720
Ala Val Leu Ile Asn Glu Lys Gly Glu Val Phe Cys Gly Gly Thr Ile
225                 230                 235                 240 ttg agc ccc atc cat gtg ctt act gca gcc cac tgc att aac cag acc     768
Leu Ser Pro Ile His Val Leu Thr Ala Ala His Cys Ile Asn Gln Thr
                245                 250                 255 aag agc gtt tca gtt att gta ggg gaa ata gac ata tca aga aaa gaa     816
Lys Ser Val Ser Val Ile Val Gly Glu Ile Asp Ile Ser Arg Lys Glu
                260                 265                 270 acc aga cgt ctt ctt tct gtg gat aaa ata tat gtg cat aaa aaa ttt     864
Thr Arg Arg Leu Leu Ser Val Asp Lys Ile Tyr Val His Lys Lys Phe
            275                 280                 285 gtt cct ccc aac tct tac tat caa aac att gat cgt ttc gcc tat gac     912
```

```
Val Pro Pro Asn Ser Tyr Tyr Gln Asn Ile Asp Arg Phe Ala Tyr Asp
    290                 295                 300 tat gat ata gcc atc atc cga atg aag acc cct atc cag ttc tct gaa     960
Tyr Asp Ile Ala Ile Ile Arg Met Lys Thr Pro Ile Gln Phe Ser Glu
305                 310                 315                 320 aat gtg gtt cct gcc tgc ctt ccc act gct gat ttt gcc aag gaa gtc    1008
Asn Val Val Pro Ala Cys Leu Pro Thr Ala Asp Phe Ala Lys Glu Val
                325                 330                 335 ctc atg aaa caa gat tct ggc atc gtt agt gga ttt ggg cgt act caa    1056
Leu Met Lys Gln Asp Ser Gly Ile Val Ser Gly Phe Gly Arg Thr Gln
            340                 345                 350 tct ata gga tat acc tct aac ata ctt aaa gtc att acg gtt cct tat    1104
Ser Ile Gly Tyr Thr Ser Asn Ile Leu Lys Val Ile Thr Val Pro Tyr
        355                 360                 365 gtg gac agg cac acc tgc atg ctt tcc agt aat ttt cga att act caa    1152
Val Asp Arg His Thr Cys Met Leu Ser Ser Asn Phe Arg Ile Thr Gln
370                 375                 380 aat atg ttc tgt gct ggc tat gat act ctg cct caa gat gca tgc cag    1200
Asn Met Phe Cys Ala Gly Tyr Asp Thr Leu Pro Gln Asp Ala Cys Gln
385                 390                 395                 400 gga gac agt ggg ggg ccc cac atc act gca tac gga gat acc cac ttt    1248
Gly Asp Ser Gly Gly Pro His Ile Thr Ala Tyr Gly Asp Thr His Phe
                405                 410                 415 gtt act ggg att atc agc tgg ggg gaa gga tgt gca cgg aaa ggc aaa    1296
Val Thr Gly Ile Ile Ser Trp Gly Glu Gly Cys Ala Arg Lys Gly Lys
            420                 425                 430 tat ggt gtt tac aca aaa gtg tcc aat ttc atc cct tgg ata aaa aaa    1344
Tyr Gly Val Tyr Thr Lys Val Ser Asn Phe Ile Pro Trp Ile Lys Lys
        435                 440                 445 ata atg agt cta aag taacccagta cagagtcaag cactggtcgg ctctaa        1395
Ile Met Ser Leu Lys
    450

<210> SEQ ID NO 14
<211> LENGTH: 453
<212> TYPE: PRT
<213> ORGANISM: Notechis scutatus

<400> SEQUENCE: 14

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45

Arg Pro Gly Asn Ile Glu Arg Glu Cys Ile Glu Glu Lys Cys Ser Lys
    50                  55                  60

Glu Glu Ala Arg Glu Val Phe Glu Asp Asn Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Phe Lys Ser
        115                 120                 125

Cys Arg Ala Phe Asn Gly Asn Cys Trp His Phe Cys Lys Arg Val Gln
    130                 135                 140

Ser Glu Thr Gln Cys Ser Cys Ala Glu Ser Tyr Leu Leu Gly Val Asp
```

```
            145                 150                 155                 160
Gly His Ser Cys Val Ala Glu Gly Asp Phe Ser Cys Gly Arg Asn Ile
                165                 170                 175
Lys Ala Arg Asn Lys Arg Glu Ala Ser Leu Pro Asp Phe Val Gln Ser
            180                 185                 190
Gln Lys Ala Thr Val Leu Lys Lys Ser Asp Asn Pro Ser Pro Asp Ile
        195                 200                 205
Arg Ile Val Asn Gly Met Asp Cys Lys Leu Gly Glu Cys Pro Trp Gln
    210                 215                 220
Ala Val Leu Ile Asn Glu Lys Gly Glu Val Phe Cys Gly Gly Thr Ile
225                 230                 235                 240
Leu Ser Pro Ile His Val Leu Thr Ala Ala His Cys Ile Asn Gln Thr
                245                 250                 255
Lys Ser Val Ser Val Ile Val Gly Glu Ile Asp Ile Ser Arg Lys Glu
            260                 265                 270
Thr Arg Arg Leu Leu Ser Val Asp Lys Ile Tyr Val His Lys Lys Phe
        275                 280                 285
Val Pro Pro Asn Ser Tyr Tyr Gln Asn Ile Asp Arg Phe Ala Tyr Asp
    290                 295                 300
Tyr Asp Ile Ala Ile Ile Arg Met Lys Thr Pro Ile Gln Phe Ser Glu
305                 310                 315                 320
Asn Val Val Pro Ala Cys Leu Pro Thr Ala Asp Phe Ala Lys Glu Val
                325                 330                 335
Leu Met Lys Gln Asp Ser Gly Ile Val Ser Gly Phe Gly Arg Thr Gln
            340                 345                 350
Ser Ile Gly Tyr Thr Ser Asn Ile Leu Lys Val Ile Thr Val Pro Tyr
        355                 360                 365
Val Asp Arg His Thr Cys Met Leu Ser Ser Asn Phe Arg Ile Thr Gln
    370                 375                 380
Asn Met Phe Cys Ala Gly Tyr Asp Thr Leu Pro Gln Asp Ala Cys Gln
385                 390                 395                 400
Gly Asp Ser Gly Gly Pro His Ile Thr Ala Tyr Gly Asp Thr His Phe
                405                 410                 415
Val Thr Gly Ile Ile Ser Trp Gly Glu Gly Cys Ala Arg Lys Gly Lys
            420                 425                 430
Tyr Gly Val Tyr Thr Lys Val Ser Asn Phe Ile Pro Trp Ile Lys Lys
        435                 440                 445
Ile Met Ser Leu Lys
    450

<210> SEQ ID NO 15
<211> LENGTH: 1359
<212> TYPE: DNA
<213> ORGANISM: Notechis scutatus

<400> SEQUENCE: 15
atggctcctc aactactcct ctgtctgatc ctcacttttc tgtggagtct cccagaggct      60
gaaagtaatg tattcttaaa aagcaaagtg gcaaatagat ttttgcaaag aacaaaacga    120
tctaattcac tgtttgagga aattagacct ggaaacattg aagggaatg cattgaggag     180 aaatgttcaa agaagaagc cagggaggta tttgaagata cgagaaaac tgagaccttc      240 tggaatgttt atgtagatgg ggatcagtgt tcatcaaacc cctgtcatta tcgcgggaca    300
tgcaaagatg gcattggtag ctatacctgt acctgcttgc ctaactatga agggaaaaac    360
```

-continued

```
tgtgaaaaag tcttatttaa gtcctgcaga gcattcaatg gtaactgttg gcacttctgc    420
aaacgtgttc aaagtgaaac tcagtgttca gtgctgaaaa gttacctttt gggagttgat    480
gggcactctt gtgttgctga aggtgacttt tcatgtggta gaaatataaa agcaaggaac    540
aagagggaag caagtctgcc tgactttgtg cagtcccaga aggcaactgt gctgaaaaaa    600
tctgataatc caagccctga tatcagaatt gttaatggaa tggactgcaa actgggtgaa    660
tgtccatggc aggcagttct gataaatgaa aaaggagaag tgttttgtgg aggaacaatt    720
ttgagcccca tccatgtgct tactgcagcc cactgcatta accagaccaa gagcgtttca    780
gttattgtag gggaaataga catatcaaga aagaaacca gacgtcttct ttctgtggat     840
aaaatatatg tgcataaaaa atttgttcct cccaactctt actatcaaaa cattgatcgt    900
ttcgcctatg actatgatat agccatcatc cgaatgaaga cccctatcca gttctctgaa    960
aatgtggttc ctgcctgcct tcccactgct gattttgcca aggaagtcct catgaaacaa   1020
gattctggca tcgttagtgg atttgggcgt actcaatcta taggatatac ctctaacata   1080
cttaaagtca ttacggttcc ttatgtggac aggcacacct gcatgctttc cagtaatttt   1140
cgaattactc aaaatatgtt ctgtgctggc tatgatactc tgcctcaaga tgcatgccag   1200
ggagacagtg gggggcccca tcactgca tacggagata cccactttgt tactgggatt    1260
atcagctggg gggaaggatg tgcacggaaa ggcaaatatg gtgtttacac aaaagtgtcc   1320
aatttcatcc cttggataaa aaaaataatg agtctaaag                          1359
```

<210> SEQ ID NO 16
<211> LENGTH: 1401
<212> TYPE: DNA
<213> ORGANISM: Tropidechis carinatus
<220> FEATURE:
<221> NAME/KEY: CDS
<222> LOCATION: (1)..(1365)

<400> SEQUENCE: 16

```
atg gct cct caa cta ctc ctc tgt ctg atc ctc act ttt ctg tgg agt      48
Met Ala Pro Gln Leu Leu Leu Cys Leu Ile Leu Thr Phe Leu Trp Ser
1               5                   10                  15 ctc cca gag gct gaa agt aat gta ttc tta aaa agc aaa gtg gca aat      96
Leu Pro Glu Ala Glu Ser Asn Val Phe Leu Lys Ser Lys Val Ala Asn
                20                  25                  30 aga ttt ttg caa aga aca aaa cga tct aat tca ctg ttt gag gaa att     144
Arg Phe Leu Gln Arg Thr Lys Arg Ser Asn Ser Leu Phe Glu Glu Ile
            35                  40                  45 aga cct gga aac att gaa agg gaa tgc att gag gag aaa tgt tca aaa     192
Arg Pro Gly Asn Ile Glu Arg Glu Cys Ile Glu Glu Lys Cys Ser Lys
        50                  55                  60 gaa gaa gcc agg gag gta ttt gaa gat aac gag aaa act gag acc ttc     240
Glu Glu Ala Arg Glu Val Phe Glu Asp Asn Glu Lys Thr Glu Thr Phe
65                  70                  75                  80 tgg aat gtt tat gta gat ggg gat cag tgt tca tca aac ccc tgt cat     288
Trp Asn Val Tyr Val Asp Gly Asp Gln Cys Ser Ser Asn Pro Cys His
                85                  90                  95 tat cgc ggg aca tgc aaa gat ggc att ggt agc tat acc tgt acc tgc     336
Tyr Arg Gly Thr Cys Lys Asp Gly Ile Gly Ser Tyr Thr Cys Thr Cys
                100                 105                 110 ttg cct aac tat gaa ggg aaa aac tgt gaa aaa gtc tta tat cag tcc     384
Leu Pro Asn Tyr Glu Gly Lys Asn Cys Glu Lys Val Leu Tyr Gln Ser
            115                 120                 125 tgc aga gtg gac aat ggt aac tgt tgg cac ttc tgc aaa cgt gtt caa     432
Cys Arg Val Asp Asn Gly Asn Cys Trp His Phe Cys Lys Arg Val Gln
```

```
              130                 135                 140
agt gaa act cag tgt tca tgt gct gaa agt tac cgt ttg gga gtt gat     480
Ser Glu Thr Gln Cys Ser Cys Ala Glu Ser Tyr Arg Leu Gly Val Asp
145                 150                 155                 160 ggg cac tct tgt gtt gct gaa ggt gac ttt tca tgt ggt aga aat ata     528
Gly His Ser Cys Val Ala Glu Gly Asp Phe Ser Cys Gly Arg Asn Ile
                        165                 170                 175 aaa gca agg aac aag agg gaa gca agt ctg cct gac ttt gtg cag tcc     576
Lys Ala Arg Asn Lys Arg Glu Ala Ser Leu Pro Asp Phe Val Gln Ser
                180                 185                 190 caa aag gca act ttg ctg aaa aaa tct gat aat cca agc cct gat atc     624
Gln Lys Ala Thr Leu Leu Lys Lys Ser Asp Asn Pro Ser Pro Asp Ile
            195                 200                 205 aga att gtt aat gga atg gac tgc aaa ctg ggt gaa tgt cca tgg cag     672
Arg Ile Val Asn Gly Met Asp Cys Lys Leu Gly Glu Cys Pro Trp Gln
        210                 215                 220 gca gtt ctg ata aat gaa aaa gga gaa gtg ttt tgt gga gga aca att     720
Ala Val Leu Ile Asn Glu Lys Gly Glu Val Phe Cys Gly Gly Thr Ile
225                 230                 235                 240 ttg agt ccc atc cat gtg ctt act gca gcc cac tgc att aac cag acc     768
Leu Ser Pro Ile His Val Leu Thr Ala Ala His Cys Ile Asn Gln Thr
                    245                 250                 255 aag agc gtt tca gtt att gta ggg gaa ata gac ata tca aga aaa gaa     816
Lys Ser Val Ser Val Ile Val Gly Glu Ile Asp Ile Ser Arg Lys Glu
                260                 265                 270 acc aga cgt ctt ctt tct gtg gat aaa ata tat gtg cat aca aaa ttt     864
Thr Arg Arg Leu Leu Ser Val Asp Lys Ile Tyr Val His Thr Lys Phe
            275                 280                 285 gtt cct ccc aac tat tac tat gtg cat caa aac ttt gat cgt gtc gcc     912
Val Pro Pro Asn Tyr Tyr Tyr Val His Gln Asn Phe Asp Arg Val Ala
        290                 295                 300 tat gac tat gat ata gcc atc atc cga atg aag acc cct atc cag ttc     960
Tyr Asp Tyr Asp Ile Ala Ile Ile Arg Met Lys Thr Pro Ile Gln Phe
305                 310                 315                 320 tct gaa aat gtg gtt cct gcc tgc ctt ccc act gct gat ttt gcc aac    1008
Ser Glu Asn Val Val Pro Ala Cys Leu Pro Thr Ala Asp Phe Ala Asn
                    325                 330                 335 gaa gtc ctc atg aaa caa gat tct ggc atc gtt agt gga ttt ggg cgt    1056
Glu Val Leu Met Lys Gln Asp Ser Gly Ile Val Ser Gly Phe Gly Arg
                340                 345                 350 att caa ttt aaa caa ccg acc tct aac aca ctt aaa gtc att acg gtt    1104
Ile Gln Phe Lys Gln Pro Thr Ser Asn Thr Leu Lys Val Ile Thr Val
            355                 360                 365 cct tat gtg gac agg cac acc tgc atg ctt tcc agt gat ttt cga att    1152
Pro Tyr Val Asp Arg His Thr Cys Met Leu Ser Ser Asp Phe Arg Ile
        370                 375                 380 act caa aat atg ttc tgt gct ggc tat gat act ctg cct caa gat gca    1200
Thr Gln Asn Met Phe Cys Ala Gly Tyr Asp Thr Leu Pro Gln Asp Ala
385                 390                 395                 400 tgc cag gga gac agt ggg ggc ccc cac atc act gca tac aga gat acc    1248
Cys Gln Gly Asp Ser Gly Gly Pro His Ile Thr Ala Tyr Arg Asp Thr
                    405                 410                 415 cac ttt att act ggg att atc agc tgg ggg gaa gga tgt gca cgg aaa    1296
His Phe Ile Thr Gly Ile Ile Ser Trp Gly Glu Gly Cys Ala Arg Lys
                420                 425                 430 ggc aaa tat ggt gtt tac aca aaa gtg tcc aaa ttc atc cct tgg ata    1344
Gly Lys Tyr Gly Val Tyr Thr Lys Val Ser Lys Phe Ile Pro Trp Ile
            435                 440                 445 aaa aaa ata atg agt cta aag taacccagta cagagtcaag cactggtcgg       1395
Lys Lys Ile Met Ser Leu Lys
```

```
Lys Lys Ile Met Ser Leu Lys
    450             455 ctctaa                                                                      1401

<210> SEQ ID NO 17
<211> LENGTH: 455
<212> TYPE: PRT
<213> ORGANISM: Tropidechis carinatus

<400> SEQUENCE: 17

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
            20                  25                  30

Arg Phe Leu Gln Arg Thr Lys Arg Ser Asn Ser Leu Phe Glu Glu Ile
        35                  40                  45

Arg Pro Gly Asn Ile Glu Arg Glu Cys Ile Glu Glu Lys Cys Ser Lys
    50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Tyr Gln Ser
        115                 120                 125

Cys Arg Val Asp Asn Gly Asn Cys Trp His Phe Cys Lys Arg Val Gln
    130                 135                 140

Ser Glu Thr Gln Cys Ser Cys Ala Glu Ser Tyr Arg Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
    210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
                245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Thr Lys Phe
        275                 280                 285

Val Pro Pro Asn Tyr Tyr Tyr Val His Gln Asn Phe Asp Arg Val Ala
    290                 295                 300

Tyr Asp Tyr Asp Ile Ala Ile Ile Arg Met Lys Thr Pro Ile Gln Phe
305                 310                 315                 320

Ser Glu Asn Val Val Pro Ala Cys Leu Pro Thr Ala Asp Phe Ala Asn
                325                 330                 335

Glu Val Leu Met Lys Gln Asp Ser Gly Ile Val Ser Gly Phe Gly Arg
            340                 345                 350
```

```
Ile Gln Phe Lys Gln Pro Thr Ser Asn Thr Leu Lys Val Ile Thr Val
            355                 360                 365
Pro Tyr Val Asp Arg His Thr Cys Met Leu Ser Ser Asp Phe Arg Ile
        370                 375                 380
Thr Gln Asn Met Phe Cys Ala Gly Tyr Asp Thr Leu Pro Gln Asp Ala
385                 390                 395                 400
Cys Gln Gly Asp Ser Gly Gly Pro His Ile Thr Ala Tyr Arg Asp Thr
                405                 410                 415
His Phe Ile Thr Gly Ile Ile Ser Trp Gly Glu Gly Cys Ala Arg Lys
            420                 425                 430
Gly Lys Tyr Gly Val Tyr Thr Lys Val Ser Lys Phe Ile Pro Trp Ile
        435                 440                 445
Lys Lys Ile Met Ser Leu Lys
    450                 455

<210> SEQ ID NO 18
<211> LENGTH: 1365
<212> TYPE: DNA
<213> ORGANISM: Tropidechis carinatus

<400> SEQUENCE: 18
atggctcctc aactactcct ctgtctgatc ctcactttc tgtggagtct cccagaggct        60
gaaagtaatg tattcttaaa aagcaaagtg gcaaatagat ttttgcaaag aacaaaacga      120
tctaattcac tgtttgagga aattagacct ggaaacattg aaagggaatg cattgaggag      180
aaatgttcaa agaagaagc cagggaggta tttgaagata cgagaaaac tgagaccttc        240 tggaatgttt atgtagatgg ggatcagtgt tcatcaaacc cctgtcatta tcgcgggaca      300
tgcaaagatg gcattggtag ctatacctgt acctgcttgc ctaactatga agggaaaaac      360
tgtgaaaaag tcttatatca gtcctgcaga gtggacaatg gtaactgttg cacttctgc       420 aaacgtgttc aaagtgaaac tcagtgttca tgtgctgaaa gttaccgttt gggagttgat      480
gggcactctt gtgttgctga aggtgacttt tcatgtggta gaaatataaa agcaaggaac      540
aagagggaag caagtctgcc tgactttgtg cagtcccaaa aggcaacttt gctgaaaaaa      600
tctgataatc aagccctga tatcagaatt gttaatggaa tggactgcaa actgggtgaa       660
tgtccatggc aggcagttct gataaatgaa aaaggagaag tgttttgtgg aggaacaatt      720
ttgagtccca tccatgtgct tactgcagcc cactgcatta accagaccaa gagcgtttca      780
gttattgtag gggaaataga catatcaaga aaagaaacca gacgtcttct ttctgtggat      840
aaaatatatg tgcatacaaa atttgttcct cccaactatt actatgtgca tcaaaacttt      900
gatcgtgtcg cctatgacta tgatatagcc atcatccgaa tgaagacccc tatccagttc     960
tctgaaaatg tggttcctgc ctgccttccc actgctgatt tgccaacga agtcctcatg     1020 aaacaagatt ctggcatcgt tagtggattt gggcgtattc aatttaaaca accgacctct     1080
aacacactta agtcattac ggttccttat gtggacaggc acacctgcat gctttccagt      1140
gattttcgaa ttactcaaaa tatgttctgt gctggctatg atactctgcc tcaagatgca     1200
tgccagggag acagtggggg gccccacatc actgcataca gagatacccc ctttattact    1260
gggattatca gctgggggga aggatgtgca cggaaaggca aatatggtgt ttacacaaaa     1320
gtgtccaaat tcatcccttg gataaaaaaa ataatgagtc taaag                     1365

<210> SEQ ID NO 19
<211> LENGTH: 12
<212> TYPE: PRT
```

```
<213> ORGANISM: Artificial Sequence
<220> FEATURE:
<223> OTHER INFORMATION: Synthetic peptide

<400> SEQUENCE: 19

Lys Arg Glu Ala Ser Leu Pro Asp Phe Val Gln Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide

<400> SEQUENCE: 20

Leu Lys Lys Ser Asp Asn Pro Ser Pro Asp Ile Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa = any amino acid, preferably valine or
      isoleucine
<220> FEATURE:
<221> NAME/KEY: VARIANT
<222> LOCATION: (8)..(8)
<223> OTHER INFORMATION: Xaa = any amino acid, preferably asparginine or
      aspartic acid
<220> FEATURE:
<221> NAME/KEY: VARIANT
<222> LOCATION: (9)..(9)
<223> OTHER INFORMATION: Xaa = any amino acid, preferably asparginine,
      lysine or isoleucine

<400> SEQUENCE: 21

Ser Val Xaa Val Gly Glu Ile Xaa Xaa Ser Arg
1               5                   10

<210> SEQ ID NO 22
<211> LENGTH: 29
<212> TYPE: PRT
<213> ORGANISM: Artificial Sequence
<220> FEATURE:
<223> OTHER INFORMATION: Synthetic peptide

<400> SEQUENCE: 22

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys
            20                  25

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Ala Asn Arg Phe Leu Gln Arg Thr Lys Arg
1               5                   10
```

```
<210> SEQ ID NO 24
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 24

Lys Arg Glu Ala Ser Leu Pro Asp Phe Val Gln Ser Xaa Xaa Ala Xaa
1               5                   10                  15

Xaa Leu Lys Lys Ser Asp Asn Pro Ser Pro Asp Ile Arg
            20                  25

<210> SEQ ID NO 25
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(30)
<223> OTHER INFORMATION: Xaa can be any naturally occurring amino acid

<400> SEQUENCE: 25

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Xaa Ala Asn
            20                  25                  30

Arg Phe Leu Gln Arg Thr Lys Arg
        35                  40

<210> SEQ ID NO 26
<211> LENGTH: 1502
<212> TYPE: DNA
<213> ORGANISM: Homo sapiens
<220> FEATURE:
<221> NAME/KEY: CDS
<222> LOCATION: (26)..(1489)

<400> SEQUENCE: 26
cagggacaca gtactcggcc acacc atg ggg cgc cca ctg cac ctc gtc ctg        52
                            Met Gly Arg Pro Leu His Leu Val Leu
                             1               5 ctc agt gcc tcc ctg gct ggc ctc ctg ctc ggg gaa agt ctg ttc           100
Leu Ser Ala Ser Leu Ala Gly Leu Leu Leu Gly Glu Ser Leu Phe
 10              15                  20                  25 atc cgc agg gag cag gcc aac aac atc ctg gcg agg gtc acg agg gcc       148
Ile Arg Arg Glu Gln Ala Asn Asn Ile Leu Ala Arg Val Thr Arg Ala
                30                  35                  40 aat tcc ttt ctt gaa gag atg aag aaa gga cac ctc gaa aga gag tgc       196
Asn Ser Phe Leu Glu Glu Met Lys Lys Gly His Leu Glu Arg Glu Cys
            45                  50                  55 atg gaa gag acc tgc tca tac gaa gag gcc cgc gag gtc ttt gag gac       244
Met Glu Glu Thr Cys Ser Tyr Glu Glu Ala Arg Glu Val Phe Glu Asp
        60                  65                  70 agc gac aag acg aat gaa ttc tgg aat aaa tac aaa gat ggc gac cag       292
```

```
                Ser Asp Lys Thr Asn Glu Phe Trp Asn Lys Tyr Lys Asp Gly Asp Gln
                 75                  80                  85 tgt gag acc agt cct tgc cag aac cag ggc aaa tgt aaa gac ggc ctc        340
Cys Glu Thr Ser Pro Cys Gln Asn Gln Gly Lys Cys Lys Asp Gly Leu
 90                  95                 100                 105 ggg gaa tac acc tgc acc tgt tta gaa gga ttc gaa ggc aaa aac tgt        388
Gly Glu Tyr Thr Cys Thr Cys Leu Glu Gly Phe Glu Gly Lys Asn Cys
                110                 115                 120 gaa tta ttc aca cgg aag ctc tgc agc ctg gac aac ggg gac tgt gac        436
Glu Leu Phe Thr Arg Lys Leu Cys Ser Leu Asp Asn Gly Asp Cys Asp
                125                 130                 135 cag ttc tgc cac gag gaa cag aac tct gtg gtg tgc tcc tgc gcc cgc        484
Gln Phe Cys His Glu Glu Gln Asn Ser Val Val Cys Ser Cys Ala Arg
            140                 145                 150 ggg tac acc ctg gct gac aac ggc aag gcc tgc att ccc aca ggg ccc        532
Gly Tyr Thr Leu Ala Asp Asn Gly Lys Ala Cys Ile Pro Thr Gly Pro
            155                 160                 165 tac ccc tgt ggg aaa cag acc ctg gaa cgg agg aag agg tca gtg gcc        580
Tyr Pro Cys Gly Lys Gln Thr Leu Glu Arg Arg Lys Arg Ser Val Ala
170                 175                 180                 185 cag gcc acc agc agc agc ggg gag gcc cct gac agc atc aca tgg aag        628
Gln Ala Thr Ser Ser Ser Gly Glu Ala Pro Asp Ser Ile Thr Trp Lys
                190                 195                 200 cca tat gat gca gcc gac ctg gac ccc acc gag aac ccc ttc gac ctg        676
Pro Tyr Asp Ala Ala Asp Leu Asp Pro Thr Glu Asn Pro Phe Asp Leu
                205                 210                 215 ctt gac ttc aac cag acg cag cct gag agg ggc gac aac aac ctc acc        724
Leu Asp Phe Asn Gln Thr Gln Pro Glu Arg Gly Asp Asn Asn Leu Thr
                220                 225                 230 agg atc gtg gga ggc cag gaa tgc aag gac ggg gag tgt ccc tgg cag        772
Arg Ile Val Gly Gly Gln Glu Cys Lys Asp Gly Glu Cys Pro Trp Gln
            235                 240                 245 gcc ctg ctc atc aat gag gaa aac gag ggt ttc tgt ggt gga acc att        820
Ala Leu Leu Ile Asn Glu Glu Asn Glu Gly Phe Cys Gly Gly Thr Ile
250                 255                 260                 265 ctg agc gag ttc tac atc cta acg gca gcc cac tgt ctc tac caa gcc        868
Leu Ser Glu Phe Tyr Ile Leu Thr Ala Ala His Cys Leu Tyr Gln Ala
                270                 275                 280 aag aga ttc aag gtg agg gta ggg gac cgg aac acg gag cag gag gag        916
Lys Arg Phe Lys Val Arg Val Gly Asp Arg Asn Thr Glu Gln Glu Glu
                285                 290                 295 ggc ggt gag gcg gtg cac gag gtg gag gtg gtc atc aag cac aac cgg        964
Gly Gly Glu Ala Val His Glu Val Glu Val Val Ile Lys His Asn Arg
            300                 305                 310 ttc aca aag gag acc tat gac ttc gac atc gcc gtg ctc cgg ctc aag        1012
Phe Thr Lys Glu Thr Tyr Asp Phe Asp Ile Ala Val Leu Arg Leu Lys
            315                 320                 325 acc ccc atc acc ttc cgc atg aac gtg gcg cct gcc tgc ctc ccc gag        1060
Thr Pro Ile Thr Phe Arg Met Asn Val Ala Pro Ala Cys Leu Pro Glu
330                 335                 340                 345 cgt gac tgg gcc gag tcc acg ctg atg acg cag aag acg ggg att gtg        1108
Arg Asp Trp Ala Glu Ser Thr Leu Met Thr Gln Lys Thr Gly Ile Val
                350                 355                 360 agc ggc ttc ggg cgc acc cac gag aag ggc cgg cag tcc acc agg ctc        1156
Ser Gly Phe Gly Arg Thr His Glu Lys Gly Arg Gln Ser Thr Arg Leu
                365                 370                 375 aag atg ctg gag gtg ccc tac gtg gac cgc aac agc tgc aag ctg tcc        1204
Lys Met Leu Glu Val Pro Tyr Val Asp Arg Asn Ser Cys Lys Leu Ser
                380                 385                 390
```

-continued

| | | | | | | | | | | | | | |
|---|---|---|---|---|---|---|---|---|---|---|---|---|---|
| agc | agc | ttc | atc | atc | acc | cag | aac | atg | ttc | tgt | gcc | ggc | tac gac acc | 1252 |
| Ser | Ser | Phe | Ile | Ile | Thr | Gln | Asn | Met | Phe | Cys | Ala | Gly | Tyr Asp Thr |
| | 395 | | | | 400 | | | | 405 | | | | |

| aag | cag | gag | gat | gcc | tgc | cag | ggg | gac | agc | ggg | ggc | ccg | cac gtc acc | 1300 |
| Lys | Gln | Glu | Asp | Ala | Cys | Gln | Gly | Asp | Ser | Gly | Gly | Pro | His Val Thr |
| 410 | | | | 415 | | | | | 420 | | | | 425 |

| cgc | ttc | aag | gac | acc | tac | ttc | gtg | aca | ggc | atc | gtc | agc | tgg gga gag | 1348 |
| Arg | Phe | Lys | Asp | Thr | Tyr | Phe | Val | Thr | Gly | Ile | Val | Ser | Trp Gly Glu |
| | | | 430 | | | | | 435 | | | | | 440 |

| ggc | tgt | gcc | cgt | aag | ggg | aag | tac | ggg | atc | tac | acc | aag | gtc acc gcc | 1396 |
| Gly | Cys | Ala | Arg | Lys | Gly | Lys | Tyr | Gly | Ile | Tyr | Thr | Lys | Val Thr Ala |
| | | | 445 | | | | | 450 | | | | | 455 |

| ttc | ctc | aag | tgg | atc | gac | agg | tcc | atg | aaa | acc | agg | ggc | ttg ccc aag | 1444 |
| Phe | Leu | Lys | Trp | Ile | Asp | Arg | Ser | Met | Lys | Thr | Arg | Gly | Leu Pro Lys |
| | | 460 | | | | | 465 | | | | | 470 | |

| gcc | aag | agc | cat | gcc | ccg | gag | gtc | ata | acg | tcc | tct | cca | tta aag | 1489 |
| Ala | Lys | Ser | His | Ala | Pro | Glu | Val | Ile | Thr | Ser | Ser | Pro | Leu Lys |
| | 475 | | | | 480 | | | | | 485 | | | | tgagatccca ctc                                                                          1502

<210> SEQ ID NO 27
<211> LENGTH: 488
<212> TYPE: PRT
<213> ORGANISM: Homo sapiens

<400> SEQUENCE: 27

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

```
Cys Lys Asp Gly Glu Cys Pro Trp Gln Ala Leu Leu Ile Asn Glu Glu
            245                 250                 255

Asn Glu Gly Phe Cys Gly Gly Thr Ile Leu Ser Glu Phe Tyr Ile Leu
        260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
        450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 28
<211> LENGTH: 456
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(456)
<223> OTHER INFORMATION: Any Xaa not specifically identified = any amino
      acid
<220> FEATURE:
<221> NAME/KEY: VARIANT
<222> LOCATION: (41)..(41)
<223> OTHER INFORMATION: Xaa = small amino acid residue
<220> FEATURE:
<221> NAME/KEY: VARIANT
<222> LOCATION: (45)..(45)
<223> OTHER INFORMATION: Xaa = hydrophobic amino acid residue
<220> FEATURE:
<221> NAME/KEY: VARIANT
<222> LOCATION: (48)..(48)
<223> OTHER INFORMATION: Xaa = hydrophobic amino acid residue
<220> FEATURE:
<221> NAME/KEY: VARIANT
<222> LOCATION: (49)..(49)
<223> OTHER INFORMATION: Xaa = basic amino acid residue
<220> FEATURE:
<221> NAME/KEY: VARIANT
<222> LOCATION: (50)..(50)
```

```
<223> OTHER INFORMATION: Xaa = small amino acid residue
<220> FEATURE:
<221> NAME/KEY: VARIANT
<222> LOCATION: (61)..(61)
<223> OTHER INFORMATION: Xaa = basic amino acid residue
<220> FEATURE:
<221> NAME/KEY: VARIANT
<222> LOCATION: (70)..(70)
<223> OTHER INFORMATION: Xaa = hydrophobic amino acid residue
<220> FEATURE:
<221> NAME/KEY: VARIANT
<222> LOCATION: (72)..(72)
<223> OTHER INFORMATION: Xaa = charged amino acid residue
<220> FEATURE:
<221> NAME/KEY: VARIANT
<222> LOCATION: (79)..(79)
<223> OTHER INFORMATION: Xaa = small amino acid residue
<220> FEATURE:
<221> NAME/KEY: VARIANT
<222> LOCATION: (114)..(114)
<223> OTHER INFORMATION: Xaa = small amino acid residue
<220> FEATURE:
<221> NAME/KEY: VARIANT
<222> LOCATION: (124)..(124)
<223> OTHER INFORMATION: Xaa = hydrophobic amino acid residue
<220> FEATURE:
<221> NAME/KEY: VARIANT
<222> LOCATION: (126)..(126)
<223> OTHER INFORMATION: Xaa = hydrophobic amino acid residue
<220> FEATURE:
<221> NAME/KEY: VARIANT
<222> LOCATION: (146)..(146)
<223> OTHER INFORMATION: Xaa = acidic amino acid residue
<220> FEATURE:
<221> NAME/KEY: VARIANT
<222> LOCATION: (154)..(154)
<223> OTHER INFORMATION: Xaa = small amino acid residue
<220> FEATURE:
<221> NAME/KEY: VARIANT
<222> LOCATION: (178)..(178)
<223> OTHER INFORMATION: Xaa = small amino acid residue
<220> FEATURE:
<221> NAME/KEY: VARIANT
<222> LOCATION: (193)..(193)
<223> OTHER INFORMATION: Xaa = neutral/polar amino acid residue
<220> FEATURE:
<221> NAME/KEY: VARIANT
<222> LOCATION: (197)..(197)
<223> OTHER INFORMATION: Xaa = hydrophobic amino acid residue
<220> FEATURE:
<221> NAME/KEY: VARIANT
<222> LOCATION: (210)..(210)
<223> OTHER INFORMATION: Xaa = hydrophobic amino acid residue
<220> FEATURE:
<221> NAME/KEY: VARIANT
<222> LOCATION: (227)..(227)
<223> OTHER INFORMATION: Xaa = hydrophobic amino acid residue
<220> FEATURE:
<221> NAME/KEY: VARIANT
<222> LOCATION: (229)..(230)
<223> OTHER INFORMATION: Xaa = charged amino acid residue
<220> FEATURE:
<221> NAME/KEY: VARIANT
<222> LOCATION: (255)..(255)
<223> OTHER INFORMATION: Xaa = small amino acid residue
<220> FEATURE:
<221> NAME/KEY: VARIANT
<222> LOCATION: (256)..(256)
<223> OTHER INFORMATION: Xaa = charged amino acid residue
<220> FEATURE:
<221> NAME/KEY: VARIANT
<222> LOCATION: (258)..(258)
<223> OTHER INFORMATION: Xaa = hydrophobic amino acid residue
<220> FEATURE:
<221> NAME/KEY: VARIANT
<222> LOCATION: (261)..(261)
<223> OTHER INFORMATION: Xaa = hydrophobic amino acid residue
<220> FEATURE:
<221> NAME/KEY: VARIANT
```

```
-continued

<222> LOCATION: (272)..(272)
<223> OTHER INFORMATION: Xaa = small amino acid residue
<220> FEATURE:
<221> NAME/KEY: VARIANT
<222> LOCATION: (290)..(290)
<223> OTHER INFORMATION: Xaa = small amino acid residue
<220> FEATURE:
<221> NAME/KEY: VARIANT
<222> LOCATION: (292)..(294)
<223> OTHER INFORMATION: Xaa = independently absent or selected from any
      amino acid residues
<220> FEATURE:
<221> NAME/KEY: VARIANT
<222> LOCATION: (295)..(295)
<223> OTHER INFORMATION: Xaa = independently absent or selected from
      acidic amino acid residues
<220> FEATURE:
<221> NAME/KEY: VARIANT
<222> LOCATION: (296)..(296)
<223> OTHER INFORMATION: Xaa = independently absent or selected from
      hydrophobic amino acid residues
<220> FEATURE:
<221> NAME/KEY: VARIANT
<222> LOCATION: (297)..(299)
<223> OTHER INFORMATION: Xaa = independently absent or selected from any
      amino acid residues
<220> FEATURE:
<221> NAME/KEY: VARIANT
<222> LOCATION: (300)..(300)
<223> OTHER INFORMATION: Xaa = independently absent or selected from
      hydrophobic amino acid residues
<220> FEATURE:
<221> NAME/KEY: VARIANT
<222> LOCATION: (301)..(301)
<223> OTHER INFORMATION: Xaa = independently absent or selected from
      acidic amino acid residues
<220> FEATURE:
<221> NAME/KEY: VARIANT
<222> LOCATION: (302)..(302)
<223> OTHER INFORMATION: Xaa = independently absent or selected from any
      amino acid residues
<220> FEATURE:
<221> NAME/KEY: VARIANT
<222> LOCATION: (303)..(303)
<223> OTHER INFORMATION: Xaa = independently absent or selected from
      hydrophobic amino acid residues
<220> FEATURE:
<221> NAME/KEY: VARIANT
<222> LOCATION: (304)..(304)
<223> OTHER INFORMATION: Xaa = independently absent or a small amino
      acid residue
<220> FEATURE:
<221> NAME/KEY: VARIANT
<222> LOCATION: (312)..(312)
<223> OTHER INFORMATION: Xaa = hydrophobic amino acid residue
<220> FEATURE:
<221> NAME/KEY: VARIANT
<222> LOCATION: (314)..(314)
<223> OTHER INFORMATION: Xaa - hydrophobic amino acid residue
<220> FEATURE:
<221> NAME/KEY: VARIANT
<222> LOCATION: (347)..(347)
<223> OTHER INFORMATION: Xaa = hydrophobic amino acid residue
<220> FEATURE:
<221> NAME/KEY: VARIANT
<222> LOCATION: (365)..(365)
<223> OTHER INFORMATION: Xaa = hydrophobic amino acid residue
<220> FEATURE:
<221> NAME/KEY: VARIANT
<222> LOCATION: (378)..(378)
<223> OTHER INFORMATION: Xaa = hydrophobic amino acid residue
<220> FEATURE:
<221> NAME/KEY: VARIANT
<222> LOCATION: (419)..(419)
<223> OTHER INFORMATION: Xaa = hydrophobic amino acid residue
<220> FEATURE:
<221> NAME/KEY: VARIANT
<222> LOCATION: (423)..(423)
<223> OTHER INFORMATION: Xaa = hydrophobic amino acid residue
```

```
<220> FEATURE:
<221> NAME/KEY: VARIANT
<222> LOCATION: (434)..(434)
<223> OTHER INFORMATION: Xaa = basic amino acid residue
<220> FEATURE:
<221> NAME/KEY: VARIANT
<222> LOCATION: (437)..(437)
<223> OTHER INFORMATION: Xaa = hydrophobic amino acid residue
<220> FEATURE:
<221> NAME/KEY: VARIANT
<222> LOCATION: (441)..(441)
<223> OTHER INFORMATION: Xaa = hydrophobic amino acid residue
<220> FEATURE:
<221> NAME/KEY: VARIANT
<222> LOCATION: (451)..(451)
<223> OTHER INFORMATION: Xaa = hydrophobic amino acid residue
<220> FEATURE:
<221> NAME/KEY: VARIANT
<222> LOCATION: (456)..(456)
<223> OTHER INFORMATION: Xaa is either absent or a peptide of from 1-20
      amino acids

<400> SEQUENCE: 28

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Xaa Ala Asn
            20                  25                  30

Arg Phe Leu Gln Arg Thr Lys Arg Xaa Asn Ser Leu Xaa Glu Glu Xaa
        35                  40                  45

Xaa Xaa Gly Asn Ile Glu Arg Glu Cys Ile Glu Glu Xaa Cys Ser Lys
50                  55                  60

Glu Glu Ala Arg Glu Xaa Phe Xaa Asp Xaa Glu Lys Thr Glu Xaa Phe
65                  70                  75                  80

Trp Asn Val Tyr Val Asp Gly Asp Gln Cys Ser Ser Asn Pro Cys His
                85                  90                  95

Tyr Xaa Gly Xaa Cys Lys Asp Gly Ile Gly Ser Tyr Thr Cys Thr Cys
            100                 105                 110

Leu Xaa Xaa Tyr Glu Gly Lys Asn Cys Glu Xaa Xaa Leu Xaa Xaa Ser
        115                 120                 125

Cys Arg Xaa Xaa Asn Gly Asn Cys Trp His Phe Cys Lys Xaa Val Gln
130                 135                 140

Xaa Xaa Xaa Gln Cys Ser Cys Ala Glu Xaa Tyr Xaa Leu Gly Xaa Asp
145                 150                 155                 160

Gly His Ser Cys Val Ala Xaa Gly Xaa Phe Ser Cys Gly Arg Asn Ile
                165                 170                 175

Lys Xaa Arg Asn Lys Arg Glu Ala Ser Leu Pro Asp Phe Val Gln Ser
            180                 185                 190

Xaa Xaa Ala Xaa Xaa Lys Lys Ser Asp Asn Pro Ser Pro Asp Ile Arg
        195                 200                 205

Ile Xaa Asn Gly Met Asp Cys Lys Leu Gly Glu Cys Pro Trp Gln Ala
210                 215                 220

Xaa Leu Xaa Xaa Xaa Xaa Xaa Xaa Phe Cys Gly Gly Thr Ile Leu
225                 230                 235                 240

Ser Pro Ile Xaa Val Leu Thr Ala Ala His Cys Ile Xaa Xaa Xaa Xaa
                245                 250                 255

Xaa Xaa Ser Val Xaa Val Gly Glu Ile Xaa Xaa Ser Arg Xaa Xaa Xaa
            260                 265                 270

Xaa Xaa Leu Leu Ser Val Asp Lys Xaa Tyr Val His Xaa Lys Phe Val
        275                 280                 285

Xaa Xaa Xaa Xaa Xaa Xaa Xaa Xaa Xaa Xaa Xaa Xaa Xaa Xaa Xaa
```

```
                290                 295                 300
Tyr Asp Tyr Asp Ile Ala Ile Xaa Xaa Xaa Lys Thr Pro Ile Gln Phe
305                 310                 315                 320

Ser Glu Asn Val Val Pro Ala Cys Leu Pro Thr Ala Asp Phe Ala Xaa
                325                 330                 335

Xaa Val Leu Met Lys Gln Asp Xaa Gly Ile Xaa Ser Gly Phe Gly Xaa
                340                 345                 350

Xaa Xaa Xaa Xaa Xaa Xaa Ser Xaa Xaa Leu Lys Xaa Xaa Xaa Xaa Val
                355                 360                 365

Pro Tyr Val Asp Arg His Thr Cys Met Xaa Ser Ser Xaa Xaa Xaa Ile
370                 375                 380

Thr Xaa Xaa Met Phe Cys Ala Gly Tyr Asp Thr Leu Pro Xaa Asp Ala
385                 390                 395                 400

Cys Gln Gly Asp Ser Gly Gly Pro His Ile Thr Ala Tyr Xaa Asp Thr
                405                 410                 415

His Phe Xaa Thr Gly Ile Xaa Ser Trp Gly Glu Gly Cys Ala Xaa Xaa
                420                 425                 430

Gly Xaa Tyr Gly Xaa Tyr Thr Lys Xaa Ser Xaa Phe Ile Xaa Trp Ile
                435                 440                 445

Lys Xaa Xaa Met Xaa Xaa Xaa Xaa
                450                 455

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 29

Xaa Pro Ser Thr Glu Ser Ser Thr Gly Arg Leu
1               5                   10

<210> SEQ ID NO 30
<211> LENGTH: 421
<212> TYPE: PRT
<213> ORGANISM: Artificial Sequence
<220> FEATURE:
<223> OTHER INFORMATION: Consensus Sequence

<400> SEQUENCE: 30

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Asn Ser Leu Phe Glu Glu Phe Arg
                35                  40                  45

Gly Asn Ile Glu Arg Glu Cys Ile Glu Glu Cys Ser Lys Glu Glu Ala
                50                  55                  60

Arg Glu Val Phe Glu Asp Glu Lys Thr Glu Thr Phe Trp Asn Val Tyr
65                  70                  75                  80

Val Asp Gly Asp Gln Cys Ser Ser Asn Pro Cys His Tyr Arg Gly Thr
                85                  90                  95

Cys Lys Asp Gly Ile Gly Ser Tyr Thr Cys Thr Cys Leu Tyr Glu Gly
                100                 105                 110
```

```
Lys Asn Cys Glu Val Leu Tyr Lys Ser Cys Arg Val Asp Asn Gly Asn
            115                 120                 125

Cys Trp His Phe Cys Lys Val Gln Asn Asp Gln Cys Ser Cys Ala Glu
        130                 135                 140

Tyr Leu Leu Gly Asp Gly His Ser Cys Val Ala Gly Phe Ser Cys Gly
145                 150                 155                 160

Arg Asn Ile Lys Arg Asn Lys Arg Glu Ala Ser Leu Pro Asp Phe Val
                165                 170                 175

Gln Ser Gln Asn Ala Thr Leu Leu Lys Lys Ser Asp Asn Pro Ser Pro
            180                 185                 190

Asp Ile Arg Ile Val Asn Gly Met Asp Cys Lys Leu Gly Glu Cys Pro
        195                 200                 205

Trp Gln Ala Val Leu Asp Glu Lys Val Phe Cys Gly Gly Thr Ile Leu
209                 215                 220

Ser Pro Ile Tyr Val Leu Thr Ala Ala His Cys Ile Asn Gln Thr Lys
225                 230                 235                 240

Ile Ser Val Val Gly Glu Ile Asp Ile Ser Arg Lys Glu Thr Leu
                245                 250                 255

Leu Ser Val Asp Lys Ile Tyr Val His Lys Phe Val Pro Pro Tyr Phe
            260                 265                 270

Asp Val Tyr Asp Tyr Asp Ile Ala Ile Ile Gln Met Lys Thr Pro Ile
        275                 280                 285

Gln Phe Ser Glu Asn Val Val Pro Ala Cys Leu Pro Thr Ala Asp Phe
    290                 295                 300

Ala Asn Gln Val Leu Met Lys Gln Asp Phe Gly Ile Val Ser Gly Phe
305                 310                 315                 320

Gly Arg Ile Gly Pro Ser Asn Thr Leu Lys Val Pro Tyr Val Asp
                325                 330                 335

Arg His Thr Cys Met Leu Ser Ser Phe Ile Thr Pro Met Phe Cys Ala
            340                 345                 350

Gly Tyr Asp Thr Leu Pro Asp Ala Cys Gln Gly Asp Ser Gly Gly Pro
        355                 360                 365

His Ile Thr Ala Tyr Arg Asp Thr His Phe Ile Thr Gly Ile Ser Trp
    370                 375                 380

Gly Glu Gly Cys Ala Lys Gly Lys Tyr Gly Val Tyr Thr Lys Val Ser
385                 390                 395                 400

Lys Phe Ile Pro Trp Ile Lys Ile Met Arg Lys Pro Ser Thr Glu Ser
                405                 410                 415

Ser Thr Gly Arg Leu
            420

<210> SEQ ID NO 31
<211> LENGTH: 376
<212> TYPE: PRT
<213> ORGANISM: Tropidechis carinatus

<400> SEQUENCE: 31

Ser Asn Ser Leu Phe Glu Glu Ile Arg Pro Gly Asn Ile Glu Arg Glu
1               5                   10                  15

Cys Ile Glu Glu Lys Cys Ser Lys Glu Glu Ala Arg Glu Val Phe Glu
            20                  25                  30

Asp Asn Glu Lys Thr Glu Thr Phe Trp Asn Val Tyr Val Asp Gly Asp
        35                  40                  45

Gln Cys Ser Ser Asn Pro Cys His Tyr Arg Gly Thr Cys Lys Asp Gly
```

```
                50                  55                  60
Ile Gly Ser Tyr Thr Cys Thr Cys Leu Pro Asn Tyr Glu Gly Lys Asn
 65                  70                  75                  80

Cys Glu Lys Val Leu Tyr Gln Ser Cys Arg Val Asp Asn Gly Asn Cys
                 85                  90                  95

Trp His Phe Cys Lys Arg Val Gln Ser Glu Thr Gln Cys Ser Cys Ala
                100                 105                 110

Glu Ser Tyr Arg Leu Gly Val Asp Gly His Ser Cys Val Ala Glu Gly
                115                 120                 125

Asp Phe Ser Cys Gly Arg Asn Ile Lys Ala Arg Asn Lys Ile Val Asn
130                 135                 140

Gly Met Asp Cys Lys Leu Gly Glu Cys Pro Trp Gln Ala Val Leu Ile
145                 150                 155                 160

Asn Glu Lys Gly Glu Val Phe Cys Gly Gly Thr Ile Leu Ser Pro Ile
                165                 170                 175

His Val Leu Thr Ala Ala His Cys Ile Asn Gln Thr Lys Ser Val Lys
                180                 185                 190

Glu Thr Arg Arg Leu Leu Ser Val Asp Lys Ile Tyr Val His Thr Lys
                195                 200                 205

Phe Val Pro Pro Asn Tyr Tyr Tyr Val His Gln Asn Phe Asp Arg Val
                210                 215                 220

Ala Tyr Asp Tyr Asp Ile Ala Ile Ile Arg Met Lys Thr Pro Ile Gln
225                 230                 235                 240

Phe Ser Glu Asn Val Val Pro Ala Cys Leu Pro Thr Ala Asp Phe Ala
                245                 250                 255

Asn Glu Val Leu Met Lys Gln Asp Ser Gly Ile Val Ser Gly Phe Gly
                260                 265                 270

Arg Ile Gln Phe Lys Gln Pro Thr Ser Asn Thr Leu Lys Val Ile Thr
                275                 280                 285

Val Pro Tyr Val Asp Arg His Thr Cys Met Leu Ser Ser Asp Phe Arg
                290                 295                 300

Ile Thr Gln Asn Met Phe Cys Ala Gly Tyr Asp Thr Leu Pro Gln Asp
305                 310                 315                 320

Ala Cys Gln Gly Asp Ser Gly Gly Pro His Ile Thr Ala Tyr Arg Asp
                325                 330                 335

Thr His Phe Ile Thr Gly Ile Ile Ser Trp Gly Glu Gly Cys Ala Arg
                340                 345                 350

Lys Gly Lys Tyr Gly Val Tyr Thr Lys Val Ser Lys Phe Ile Pro Trp
                355                 360                 365

Ile Lys Lys Ile Met Ser Leu Lys
370                 375

<210> SEQ ID NO 32
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(26)
<223> OTHER INFORMATION: n = a, g, or c
<220> FEATURE:
<221> NAME/KEY: misc_feature
<222> LOCATION: (27)..(27)
<223> OTHER INFORMATION: n = a, g, c or t

<400> SEQUENCE: 32
```

-continued ttttttttttt tttttttttt tttttnn        27

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
aagcagtggt atcaacgcag agtacgcggg        30

<210> SEQ ID NO 34
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (56)..(56)
<223> OTHER INFORMATION: n = a, g, or c
<220> FEATURE:
<221> NAME/KEY: misc_feature
<222> LOCATION: (57)..(57)
<223> OTHER INFORMATION: n = a, g, c or t

<400> SEQUENCE: 34
aagcagtggt atcaacgcag agtactttt tttttttttt tttttttttt tttttnn        57

<210> SEQ ID NO 35
<211> LENGTH: 45
<212> TYPE: DNA
<213> ORGANISM: Artificial Sequence
<220> FEATURE:
<223> OTHER INFORMATION: Primer

<400> SEQUENCE: 35
ctaatacgac tcactatagg gcaagcagtg gtatcaacgc agagt        45

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
ctaatacgac tcactatagg gc        22

<210> SEQ ID NO 37
<211> LENGTH: 17
<212> TYPE: DNA
<213> ORGANISM: Artificial Sequence
<220> FEATURE:
<223> OTHER INFORMATION: Primer

<400> SEQUENCE: 37
aayggwatgg aytgyaa        17

<210> SEQ ID NO 38
<211> LENGTH: 17
<212> TYPE: DNA
<213> ORGANISM: Artificial Sequence
<220> FEATURE:
<223> OTHER INFORMATION: Primer

```
<400> SEQUENCE: 38
gttttcccag tcacgac                                                    17

<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39
atcgttagtg gatttgg                                                    17

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gaaatcgtct cggtctcatt a                                               21

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
atggctcctc aactactcct ctg                                             23

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
ttagagccga ccagtgcttg actc                                            24

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide

<400> SEQUENCE: 43

Ile Val Asn Gly Met Asp Cys Lys Leu Gly Glu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)..(7)
<223> OTHER INFORMATION: Xaa = blank or cystine residues or residues
      contained post-translational modifications

<400> SEQUENCE: 44
```

```
Ala Asn Ser Leu Val Xaa Xaa Phe Lys Ser Gly Asn Ile
1               5                   10

<210> SEQ ID NO 45
<211> LENGTH: 7
<212> TYPE: PRT
<213> ORGANISM: Psuedonaja textilis

<400> SEQUENCE: 45

Arg Ile Val Asn Gly Met Asp
1               5

<210> SEQ ID NO 46
<211> LENGTH: 5
<212> TYPE: PRT
<213> ORGANISM: Tropidechis carinatus

<400> SEQUENCE: 46

Lys Ala Arg Asn Lys
1               5

<210> SEQ ID NO 47
<211> LENGTH: 5
<212> TYPE: PRT
<213> ORGANISM: Psuedonaja textilis

<400> SEQUENCE: 47

Lys Thr Arg Asn Lys
1               5

<210> SEQ ID NO 48
<211> LENGTH: 11
<212> TYPE: PRT
<213> ORGANISM: Psuedonaja textilis

<400> SEQUENCE: 48

Lys Arg Ala Asn Ser Glu Glu Glu Arg Glu Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic probe
<220> FEATURE:
<221> NAME/KEY: VARIANT
<222> LOCATION: (2)..(2)
<223> OTHER INFORMATION: Xaa = small amino acid residue, selected from
      Ser or Gly
<220> FEATURE:
<221> NAME/KEY: VARIANT
<222> LOCATION: (3)..(3)
<223> OTHER INFORMATION: Xaa = small amino acid residue, selected from
      Gln or Tyr

<400> SEQUENCE: 49

Lys Xaa Xaa Glu Phe Tyr Glu Lys Phe Asp Leu Val Ser
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 50

Ser Tyr Tyr Gln Asn Ile Asp Arg Phe Ala
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51

Tyr Tyr Tyr Val His Gln Asn Phe Asp Arg Val Ala
1               5                   10

<210> SEQ ID NO 52
<211> LENGTH: 6
<212> TYPE: PRT
<213> ORGANISM: Psudonaja textilis

<400> SEQUENCE: 52

Leu Thr Ala Ala His Cys
1               5

<210> SEQ ID NO 53
<211> LENGTH: 6
<212> TYPE: PRT
<213> ORGANISM: Tropidechis carinatus

<400> SEQUENCE: 53

Leu Thr Ala Ala His Cys
1               5

<210> SEQ ID NO 54
<211> LENGTH: 6
<212> TYPE: PRT
<213> ORGANISM: Homo sapiens

<400> SEQUENCE: 54

Leu Thr Ala Ala His Cys
1               5

<210> SEQ ID NO 55
<211> LENGTH: 11
<212> TYPE: PRT
<213> ORGANISM: Psudonaja textilis

<400> SEQUENCE: 55

Ile Val Asn Gly Met Asp Cys Lys Leu Gly Glu
1               5                   10

<210> SEQ ID NO 56
<211> LENGTH: 11
<212> TYPE: PRT
<213> ORGANISM: Tropidechis carinatus

<400> SEQUENCE: 56

Ile Val Asn Gly Met Asp Cys Lys Leu Gly Glu
1               5                   10

<210> SEQ ID NO 57
<211> LENGTH: 11
<212> TYPE: PRT
<213> ORGANISM: Homo sapiens
```

```
-continued

<400> SEQUENCE: 57

Ile Val Gly Gly Gln Glu Cys Lys Asp Gly Glu
1               5                   10

<210> SEQ ID NO 58
<211> LENGTH: 13
<212> TYPE: PRT
<213> ORGANISM: Psudonaja textilis

<400> SEQUENCE: 58

Ala Asn Ser Leu Val Glu Glu Phe Lys Ser Gly Asn Ile
1               5                   10

<210> SEQ ID NO 59
<211> LENGTH: 13
<212> TYPE: PRT
<213> ORGANISM: Tropidechis carinatus

<400> SEQUENCE: 59

Ser Asn Ser Leu Phe Glu Glu Ile Arg Pro Gly Asn Ile
1               5                   10

<210> SEQ ID NO 60
<211> LENGTH: 12
<212> TYPE: PRT
<213> ORGANISM: Psudonaja textilis

<400> SEQUENCE: 60

Ala Asn Ser Leu Val Glu Glu Phe Lys Ser Gly Asn
1               5                   10

<210> SEQ ID NO 61
<211> LENGTH: 12
<212> TYPE: PRT
<213> ORGANISM: Mus musculus

<400> SEQUENCE: 61

Ala Asn Ser Phe Phe Glu Glu Phe Lys Lys Gly Asn
1               5                   10
```

What is claimed:

1. A composition comprising an isolated snake venom protease (SVP), wherein the SVP comprises one light chain and one heavy chain,
wherein the light chain shares at least 95% sequence identity with the light chain sequence set forth by residues 41-179 of SEQ ID NO: 2 and the heavy chain shares at least 86% sequence identity with the heavy chain sequence set forth by residues 210-467 of SEQ ID NO:2, wherein the SVP comprises at least one amino acid sequence selected from the group consisting of SEQ ID NO: 19-21,
wherein the SVP does not require calcium, factor Va, or phospholipid for activity, and the SVP is an active SVP capable of processing prothrombin to thrombin, and
wherein the composition has less than 30% contaminating protein.

2. The composition of the SVP of claim 1, wherein the SVP includes a propeptide domain.

3. The composition of the SVP of claim 1, wherein the light and heavy chains are on the same polypeptide chain.

4. The composition of the SVP of claim 1, wherein the light and heavy chains are on different polypeptide chains.

5. The composition of claim 1, wherein the SVP comprises one or more of the following domains:
a first or propeptide domain which has at least 95% sequence identity with residues 1-40 of SEQ ID NO: 2;
a light chain cleavage site between residues 40 and 41 of SEQ ID NO: 2;
a domain which shares at least 95% sequence identity with residues 41-85 of SEQ ID NO: 2;
a domain which shares at least 95% sequence identity with residues 86-122 of SEQ ID NO: 2;
a domain which has at least 95% sequence identity with residues 123-165 of SEQ ID NO: 2;
a domain which has at least 95% sequence identity with residues 166-179 of SEQ ID NO: 2;
a domain which consists of residues 180-182 of SEQ ID NO: 2; and
a domain which has at least 90% sequence identity with residues 183-209 of SEQ ID NO: 2.

6. The composition of claim 1 wherein the SVP comprises residues $H^{251}$, $D^{309}$, and $S^{406}$ of SEQ ID NO: 2.

7. The composition of claim 1 wherein the SVP comprises a sequence which is the same as or differs at no more than 5 residues from the sequence of amino acids 292-305 of SEQ ID NO: 2.

8. The composition of claim 1 wherein the SVP comprises a dimeric molecule of the light chain and the heavy chain wherein the light and heavy chains have been cleaved from a propolypeptide, wherein the cleavage is between residues corresponding to 40 and 41 of SEQ ID NO: 2.

9. The composition of claim 1 wherein the SVP comprises a dimeric molecule of the light and the heavy chain having intra-chain Cys-Cys linkages between residues corresponding to 57 and 62, 90 and 101, 95 and 110, 112 and 121, 129 and 140, and 151 and 164 of the light chain and intra-chain Cys-Cys linkages between residues corresponding to 216 and 221, 236 and 252, 377 and 391, and 402 and 430 of the heavy chain, and inter-chain Cys-Cys linkages between the residue corresponding to 172 of the light chain and the residue corresponding to 329 of the heavy chain (all references are to the amino acid numbering of SEQ ID NO: 2).

10. The composition of the SVP of claim 1, wherein the light chain is the light chain of SEQ ID NO:2.

11. The composition of the SVP of claim 1, wherein the SVP heavy chain has at least 95% sequence identity with the heavy chain sequence from SEQ ID NO:2.

12. The composition of the SVP of claim 1, wherein the SVP heavy chain differs at 10 or fewer residues from the heavy chain sequence from SEQ ID NO:2.

13. The composition of the SVP of claim 1, wherein the SVP heavy chain is the heavy chain of SEQ ID NO:2.

14. The composition of the SVP of claim 1, wherein the pH of the composition is between about 5 and 9.

15. The composition of claim 14, wherein the pH of the composition is about 6.5 to 7.

16. The composition of the SVP of claim 1, further comprising a polyol.

17. The composition of claim 16, wherein the polyol is glycerol.

18. The composition of the SVP of claim 1 further comprising a pharmaceutically acceptable carrier.

19. A kit comprising the composition of claim 1 and one or more of: instructions for use; a diluent; devices or other materials for preparing the composition for administration;
pharmaceutically acceptable carriers; and devices or other materials for administration to a subject.

20. The kit of claim 19, wherein the kit comprises one or more reagents selected from the group consisting of: one or more cofactors, an anti-microbial, an antibiotic, an antiviral, an antifungal, an antiparasitic agent, an anti-inflammatory agent, an antihistamine, an anti-fibrolytic agent, an analgesic, and a growth factor.

21. The kit of claim 20, wherein the one or more cofactors is selected from the group consisting of: calcium, a phospholipid, and factor Va.

22. A device upon which is disposed an amount of the composition of claim 1 wherein the amount is sufficient to inhibit bleeding when the device is brought in contact with a subject.

23. The device of claim 22, wherein said device is any of a bandage, compress, wound dressing, suture, or an article of clothing.

24. The composition of the SVP of claim 1, wherein the SVP comprises the light chain of SEQ ID NO:2 and the heavy chain of SEQ ID NO:2.

25. The composition of claim 1 wherein the SVP further comprises the propeptide domain set forth by residues 1-40 of SEQ ID NO: 2.

26. The composition of the SVP of claim 1, wherein the SVP comprises the amino acid sequence of SEQ ID NO:2.

27. The composition of the SVP of claim 1, wherein the SVP has at least 90% sequence identity with SEQ ID NO:2.

* * * * *